(12) United States Patent
Horlitz et al.

(10) Patent No.: US 10,184,145 B2
(45) Date of Patent: Jan. 22, 2019

(54) RAPID METHOD FOR ISOLATING EXTRACELLULAR NUCLEIC ACIDS

(71) Applicant: Qiagen GmbH, Hilden (DE)

(72) Inventors: Martin Horlitz, Hilden (DE); Annette Nocon, Hilden (DE); Markus Sprenger-Haussels, Hilden (DE); Peter Grünefeld, Hilden (DE); Christoph Erbacher, Hilden (DE)

(73) Assignee: QIAGEN GmbH, Hilden (DE)

( * ) Notice: Subject to any disclaimer, the term of this patent is extended or adjusted under 35 U.S.C. 154(b) by 872 days.

(21) Appl. No.: 14/347,452

(22) PCT Filed: Sep. 25, 2012

(86) PCT No.: PCT/EP2012/068847
§ 371 (c)(1),
(2) Date: Mar. 26, 2014

(87) PCT Pub. No.: WO2013/045432
PCT Pub. Date: Apr. 4, 2013

(65) Prior Publication Data
US 2014/0227712 A1 Aug. 14, 2014

(30) Foreign Application Priority Data
Sep. 26, 2011 (EP) ..................... 11007824

(51) Int. Cl.
*C12N 15/10* (2006.01)
*C12Q 1/6806* (2018.01)

(52) U.S. Cl.
CPC ......... *C12Q 1/6806* (2013.01); *C12N 15/101* (2013.01); *C12N 15/1006* (2013.01)

(58) Field of Classification Search
CPC ............................. C12Q 1/6806; C12N 15/101
USPC .......................................... 536/25.4; 435/6.1
See application file for complete search history.

(56) References Cited

U.S. PATENT DOCUMENTS

| | | |
|---|---|---|
| 7,332,277 B2 | 2/2008 | Dhallan |
| 7,442,506 B2 | 10/2008 | Dhallan |
| 2005/0106602 A1 | 5/2005 | Akhavan-Tafti |
| 2007/0185322 A1* | 8/2007 | Akhavan-Tafti ............ C12N 15/1006 536/25.4 |
| 2010/0184069 A1 | 7/2010 | Fernando et al. |
| 2010/0209930 A1 | 8/2010 | Fernando |
| 2011/0319506 A1 | 12/2011 | Erbacher et al. |
| 2012/0245337 A1 | 9/2012 | Fabis et al. |

FOREIGN PATENT DOCUMENTS

| | | |
|---|---|---|
| DE | 10 2008 063 001 A1 | 6/2010 |
| DE | 10 2008 063 003 A1 | 6/2010 |
| EP | 11182819.0 | 9/2011 |
| WO | 97/34015 A1 | 9/1997 |
| WO | 97/35589 A1 | 10/1997 |
| WO | 02/48164 A2 | 6/2002 |
| WO | 2006/036243 A2 | 4/2006 |
| WO | 2010/072821 A1 | 7/2010 |

OTHER PUBLICATIONS

Ivancic-Jelecki et al., "Isolation of cell-free DNA from plasma by chromatography on short monolithic columns and quantification of non-apoptotic fragments by real-time polymerase chain reaction," *Journal of Chromatography A* 1216:2717-2724 (2009).
Fan et al., "Analysis of the Size Distributions of Fetal and Maternal Cell-Free DNA by Paired-End Sequencing," *Clinical Chemistry* 56:8 (2010).
Fleischhacker, "Biology of Circulating mRNA—Still More Questions Than Answers?" *Ann. N. Y. Acad. Sci.* 1075:40-49 (2006).
Fleischhacker et al., "Circulating nucleic acids (CNAs) and cancer—A survey," *Biochimica et Biophysica Acta* 1775:181-232 (2007).
Hromadnikova et al., "Quantification of Fetal and Total Circulatory DNA in Maternal Plasma Samples Before and After Size Fractionation by Agarose Gel Electrophoresis," *DNA and Cell Biology* 25(11):635-640 (2006).
Kirsch et al., "An Improved Method for the Isolation of Free-Circulating Plasma DNA and Cell-Free DNA from Other Body Fluids," *Ann. N. Y. Acad. Sci.* 1137:135-139 (2008).
Melkonyan et al., "Transrenal Nucleic Acids: From Proof of Principle to Clinical Tests," *Ann. N. Y. Acad. Sci.* 1137:73-81 (2008).
Swarup et al., "Circulating (cell-free) nucleic acids—A promising, non-invasive tool for early detection of several human diseases," *FEBS Letters* 581:795-799 (2007).

* cited by examiner

*Primary Examiner* — Jezia Riley
(74) *Attorney, Agent, or Firm* — Seed IP Law Group LLP

(57) ABSTRACT

The present invention pertains to a method for isolating extracellular nucleic acids from a sample, wherein said sample is optionally stabilized, by binding the extracellular nucleic acids to a solid phase which carries anion exchange groups, comprising the following steps: binding the extracellular nucleic acids to the solid phase in a binding mixture having a first pH which allows binding the extracellular nucleic acids to the anion exchange groups of the solid phase; wherein the sample makes up at least 85% of the volume of the binding mixture; separating the solid phase with the bound extracellular nucleic acids; optionally washing the extracellular nucleic acids; optionally eluting extracellular nucleic acids from the solid phase. The method has the advantage that large sample volumes can be processed and that extracellular nucleic acids can be isolated rapidly with a high yield. The method is particularly suitable for automatable processes.

24 Claims, 23 Drawing Sheets

RAPID METHOD FOR ISOLATING EXTRACELLULAR NUCLEIC ACIDS

The work leading to this invention has received funding from the European Community's Seventh Framework Programme (FP7/2007-2013) under grant agreement no. 222916.

FIELD OF THE INVENTION

The invention disclosed herein relates to methods for isolating extracellular nucleic acids from a sample, in particular a blood sample or a sample derived from blood such as e.g. plasma or serum, and associated technologies.

BACKGROUND

Extracellular nucleic acids have been identified in plasma, serum and other body fluids. Extracellular nucleic acids that are found in respective samples are to a certain extent degradation resistant due to the fact that they are protected from nucleases (e.g. because they are secreted in form of a proteolipid complex, are associated with proteins or are contained in vesicles). The presence of elevated levels of extracellular nucleic acids such as DNA and/or RNA in many medical conditions, malignancies, and infectious processes is of interest inter alia for screening, diagnosis, prognosis, surveillance for disease progression, for identifying potential therapeutic targets, and for monitoring treatment response. Additionally, elevated fetal DNA/RNA in maternal blood is being used to determine e.g. gender identity, assess chromosomal abnormalities, and monitor pregnancy-associated complications. Besides mammalian extracellular nucleic acids that derive e.g. from tumor cells or the fetus, samples comprising extracellular nucleic acids may also comprise other nucleic acids of interest that are not comprised in cells. An important, non-limiting example are pathogen nucleic acids such as viral nucleic acids. The efficient isolation of viral nucleic acids from samples such as in particular blood samples or samples derived from blood is also important for many diagnostic applications. Thus, extracellular nucleic acids are in particular useful in non-invasive diagnosis and prognosis and can be used e.g. as diagnostic markers in many fields of application, such as non-invasive prenatal genetic testing, oncology, transplantation medicine or many other diseases and, hence, are of diagnostic relevance (e.g. fetal- or tumor-derived nucleic acids). However, extracellular nucleic acids are also found in healthy human beings. Common applications and analysis methods of extracellular nucleic acids are e.g. described in WO97/035589, WO97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8.

Thus, the efficient isolation of extracellular nucleic acids is of great importance in order to allow a reliable analysis. However, extracellular nucleic acids are often only comprised in a low concentration in the samples. E.g. free circulating nucleic acids are present in plasma in a concentration of 1-100 ng/ml plasma. Furthermore, extracellular nucleic acids often circulate as fragments of a size of 500 nt, 300 nt (when indicating the size and hence the chain length the term "nt" also includes "bp" in case of DNA) or even less (circulating nucleosomes). Additionally, the actual target extracellular nucleic acid that is supposed to be identified for diagnostic purposes usually also represents only a small fraction among the total extracellular nucleic acids. E.g. tumor specific DNA fragments are very rare and often are comprised in a concentration that is 1000-fold less than the "normal" extracellular nucleic acid background. Thus, it is desirous to process large sample volumes in order to obtain sufficient amounts of extracellular nucleic acids and in particular sufficient amounts of the rare target molecules contained therein for the downstream assays.

Several methods are known in the prior art for isolating extracellular nucleic acids from samples, such as in particular plasma samples. Here, also several kits are commercially available. However, even though these kits provide useful results, they have drawbacks which need improvement.

For example, the QIAamp circulating nucleic acid kit allows to process a sample size of up to 5 ml for isolating the extracellular nucleic acids. However, it requires a manual nucleic acids extraction. Automating a respective large volume sample preparation is difficult to implement because the respective kit needs to handle an overall process volume of up to 25 ml due to the used chemistry (lysis and binding buffers). Standard robotic systems can, however, only process a volume of up to 3 ml. Furthermore, the respective kit also requires several method steps. Therefore, a method would be advantageous which also allows the processing of large sample volumes but at the same time allows to automate the isolation process. Other commercially available kits which aim at the isolation of for example viral nucleic acids from cell-free samples such as plasma, can only process rather small sample volumes (see for example the ChargeSwitch® EasyPlex™ viral kit). Here, the processing of larger sample volumes would be advantageous, because this would allow to increase the nucleic acid yield.

Hence, the prior art methods have several drawbacks. To overcome the drawbacks of the prior art, it is desirous to provide a method for isolating extracellular nucleic acids from large sample volumes. This would ensure that sufficient extracellular nucleic acids are isolated for the downstream applications. If this requirement is not met, there is a risk that e.g. even sensitive methods are not capable of detecting the target molecules contained in the isolated extracellular nucleic acid population. Furthermore, the prior art methods are often time-consuming and thus require several handling steps and thus hands-on-time. Here, it is desirous to provide a simple, rapid method that requires only a few steps for isolating the extracellular nucleic acids. This would also reduce potential errors due to mistakes in the handling during the preparation. Furthermore, it is desirous to provide a method that is suitable for automation. Once a diagnostic target has been established for routine testing, customers require automation to manage higher throughputs e.g. in laboratories. An automated isolation protocol would have significant advantages in the diagnostic field because it would reduce the risks of erroneous results due to errors that occur during the manual nucleic acid isolation. However, robots which are designed to perform such automated nucleic acid isolation processes are limited by the maximum sample volume which they can handle (see above). Increasing the volume by addition of reagents necessary for performing the isolation process therefore directly reduces the amount of sample that can be processed and hence the amount of nucleic acid which can be obtained by a single run of the automated isolation process. Finally, the prior art kits usually require steps for lysing the sample. Respective lysis steps—which are commonly performed in the prior art—are not only required to e.g. release the nucleic acids from the cells. Respective lysis steps are also usually performed when isolation nucleic acids from so-called cell free samples such as plasma in order to denature and/or digest protein contaminations or other contaminating substances that could interfere e.g. with the binding of the nucleic acid to the solid phase and/or could lead to an improper purification. For performing the respective lysis step, often large volumes of lysis reagents such as e.g. chaotropic agents are added. The necessity to perform a respective volume increasing lysis step is a drawback, because the volume of the actual sample that can be processed e.g. in an automated system is reduced.

US 2005/0106602 describes methods of isolating nucleic acids from samples of cellular material. No chemical lysis is performed. Instead, nucleic acid binding groups are used, which serve a dual purpose, namely to bind the nucleic acids and to support the lysis of the cells. WO2006/036243 describes a similar method.

Melkonyan et al. Transrenal nucleic acids: "From proof of principle to clinical tests", 2008, describes the isolation of extracellular nucleic acids from urine. The sample is contacted with a Q-Sepharose anion exchange matrix to bind the nucleic acids which are afterwards washed and eluted. The details of the used isolation protocol is described in Shekhtman et al. "Optimization of transrenal DNA analysis: Detection of fetal DNA in maternal urine" (Clinical Chemistry 55:4 page 723-729 (2009). Shekhtman et al. teaches to massively dilute the urine prior to binding the nucleic acids to the solid phase. 10 ml urine is diluted with 10 ml water and the resulting diluted sample is contacted with the Q-Sepharose. A similar method is described in WO2008/45505 which also describes a column based method for isolating cell-free nucleic acids from urine or blood plasma.

WO02/48164 describes a method of isolating nucleic acids using an anion exchange matrix and a charge-switch-procedure. At a first pH, the sample is brought into contact with a material which comprises an ionisable group, wherein the material has a positive charge at its first pH, such that nucleic acids are bound in the material. The nucleic acids are released at a second, higher pH at which the charge on the material is negative, neutral or less positive. The isolation of circulating nucleic acids, such as tumor derived extra cellular nucleic acid is not described.

DE 10 2008 063 003 describes a method for isolating nucleic acids using anion exchange surfaces. The isolation of extracellular nucleic acids using a large sample volume is not described. DE 10 2008 063 001 also discloses a method for isolating nucleic acids using anion exchange groups and specifically designed solid phases for binding nucleic acids.

Kirsch et al.: An improved method for the isolation of free-circulating plasma DNA and cell-free DNA from other body fluids, 2008, describes a method for isolating cell-free nucleic acids by using the NucleoSpin Plasma XS Kit (Macherey-Nagel). No anion exchange surface is used for binding the nucleic acids.

It is the object of the present invention to provide a method for isolating extracellular nucleic acids from a sample containing extracellular nucleic acids, which avoids at least one of the prior art drawbacks discussed above. In a specific embodiment it is an object of the present invention, to provide a simple, rapid method for isolating extracellular nucleic acids which is suitable for automation and allows to process large sample volumes.

SUMMARY OF THE INVENTION

The present invention is based on the finding that extracellular nucleic acids can be efficiently isolated from various different samples by using a special protocol which involves the use of an anion exchange material which binds the extracellular nucleic acids.

According to a first aspect, a method is provided for isolating extracellular nucleic acids from a sample, wherein said sample is optionally stabilized, by binding the extracellular nucleic acids to a solid phase which carries anion exchange groups, wherein said method comprises the following steps:
 a. binding the extracellular nucleic acids to the solid phase at a first pH which allows binding the extracellular nucleic acids to the anion exchange groups of the solid phase; wherein preferably the sample makes up at least 85% of the volume of the binding mixture;
 b. separating the solid phase with the bound extracellular nucleic acids;
 c. optionally washing the extracellular nucleic acids;
 d. optionally eluting extracellular nucleic acids from the solid phase.

The isolation method according to the present invention has remarkable advantages over the methods used in the prior art in that it is rapid, allows the processing of large sample volumes, requires minimum handling steps, provides a high recovery rate of extracellular nucleic acids and is automatable. All that is required for the efficient isolation of the extracellular nucleic acids is the acidification of the sample to establish the binding conditions, to bind the extracellular nucleic acids to the solid phase and to separate the solid phase with the bound extracellular nucleic acids from the remaining sample. Surprisingly, no lysis steps are mandatory to prepare the sample for nucleic acid isolation. Furthermore, there is also no necessity to add large volumes of reagents or diluting agents to prepare the sample for nucleic acid isolation and e.g. to establish the binding conditions. Therefore, the method has the advantage that the binding mixture may consist predominantly of the sample material. This is an important advantage over conventional purification methods, such as e.g. methods that are based on the use of a polysilicic acid and polysilicic acid solid phase and chaotropic agents, wherein almost 50% of the binding mixture consists of the chemistry that has to be added to lyse and/or prepare the sample for binding. The acidification that is performed according to the present invention to establish the binding conditions only contributes little to the volume of the binding mixture (usually less than 10% or even less than 5%). Thus, as there is no necessity to add large volumes of reagents to establish the binding conditions, the amount of sample that can be processed e.g. in an automated system is increased to a maximum. This is an important advantage when using automated systems which are restricted with respect to the sample volume they can handle. By enabling the processing of large sample volumes when using automated processes, the amount of isolated extracellular nucleic acids can be increased by the method according to the present invention. This in turn enables the sensitive detection and/or analysis of low abundance target molecules comprised in the extracellular nucleic acid population.

According to a second aspect, a method is provided for isolating extracellular nucleic acids from a sample which is or is derived from a body fluid, preferably selected from blood, plasma, serum, or urine, and wherein said sample is optionally stabilized, wherein for isolation extracellular nucleic acids are bound to a solid phase carrying anion exchange groups, wherein said method comprises the following steps:

a. binding extracellular nucleic acids to the solid phase in a binding mixture at a first pH≤6 which allows binding the extracellular nucleic acids to the anion exchange groups of the solid phase;
b. separating the solid phase with the bound extracellular nucleic acids;
c. optionally washing the extracellular nucleic acids;
d. eluting the extracellular nucleic acids from the solid phase preferably at a second pH which is higher than the first pH that was used for binding the extracellular nucleic acid to the solid phase;
e. isolating the extracellular nucleic acids from the eluate.

The respective method allows to concentrate extracellular nucleic acids from a large sample volume to a smaller sample volume that can be, e.g. easily handled by conventional automated systems. The isolated extracellular nucleic acids are in step e. further purified using suitable isolation methods, e.g. established isolation methods that run on automated systems. Including the concept of the present invention as preceding step in order to concentrate the extracellular nucleic acids from a large sample volume into a small sample volume has the advantage that the overall yield of extracellular nucleic acids can be increased as considerably larger sample volumes can be more conveniently processed than with conventional systems.

Furthermore, the inventors found a method to improve the recovery of small nucleic acids when using a nucleic acid binding solid phase. When isolating nucleic acids, in particular smaller nucleic acids such as e.g. extracellular nucleic acids, smaller nucleic acids are often not recovered efficiently, even though they were initially bound to the nucleic acid solid phase in the binding step. The inventors found that pretreating the nucleic acid binding solid phase with a polymer, preferably polyacrylic acid prior to binding the nucleic acids to the solid phase surprisingly improves the recovery rate of smaller nucleic acids. Thus, the present invention in a further aspect provides a nucleic acid binding solid phase that has been pretreated with a polymer, such as e.g. polyacrylic acid. Furthermore, the present invention provides a method for producing a respective nucleic acid binding solid phase, comprising contacting the nucleic acid binding solid phase with a polymer, thereby binding the polymer to the solid phase. Furthermore, the present invention pertains to a method for isolating nucleic acids, preferably extracellular nucleic acids, wherein a nucleic acid binding solid phase is used that has been pretreated with a polymer. Pretreating the solid phase with a polymer such as polyacrylic acid results in that the nucleic acid binding characteristics of the nucleic acid solid phase are improved because the recovery of small nucleic acids can be increased.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
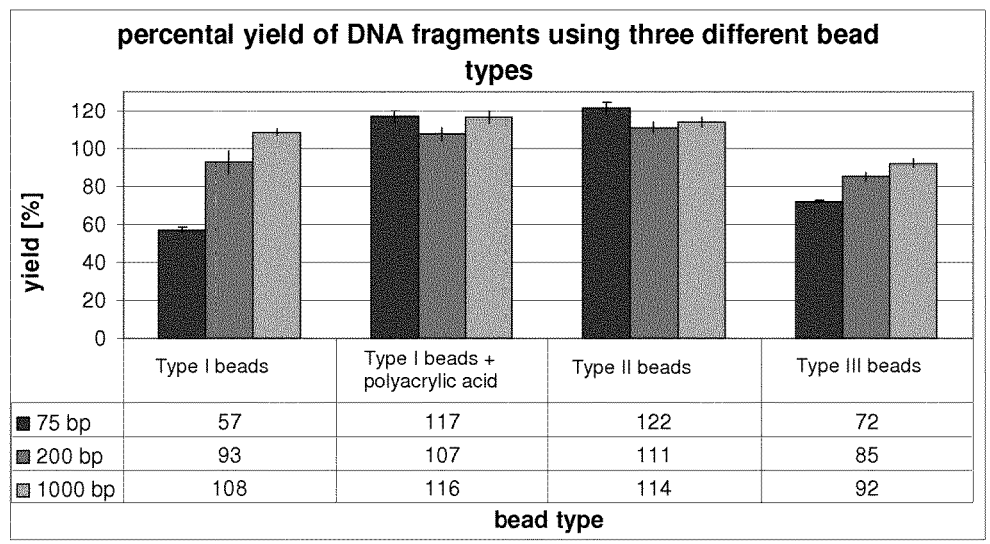
FIG. 1: Percental yield of DNA fragments using three different bead types

The present invention provides a method for isolating extracellular nucleic acids from a sample, wherein said sample is optionally stabilized, by binding the extracellular nucleic acids to a solid phase carrying anion exchange groups, wherein said method comprises the following steps:
   a. binding the extracellular nucleic acids to the solid phase at a first pH which allows binding the extracellular nucleic acids to the anion exchange groups of the solid phase; wherein, preferably, the sample makes up at least 85% of the volume of the binding mixture;
   b. separating the solid phase with the bound extracellular nucleic acids;
   c. optionally washing the extracellular nucleic acids;
   d. optionally eluting extracellular nucleic acids from the solid phase.

The key advantages associated with said method were described above in the summary of the invention. The present inventors have found that extracellular nucleic acids can be rapidly isolated from various samples with high yield using a solid phase carrying anion exchange groups that unspecifically (i.e. sequence independently) bind the extracellular nucleic acids. The method allows to process high sample volumes, because basically all that is required for establishing the binding conditions is the acidification of the sample. The acidification only adds little to the sample volume and hence the volume of the binding mixture, thereby allowing to process larger sample volumes compared to conventional methods which must add large amounts of lysis and/or binding reagents in order to enable the isolation of the nucleic acids. As is shown in the examples, the method according to the present invention can achieve, depending on the solid phase used, recovery rates of up to 100%. Thus, the processing of larger sample volumes that is possible with the method according to the present invention results in an increase of yield of extracellular nucleic acids which is an important advantage because extracellular nucleic acids are usually comprised in the samples in low concentrations such as e.g. <100 ng/ml sample. The possibility to process large sample volumes using such a simple method also allows to perform the present invention in automated systems which are restricted with respect to the maximum volume of the solution they can handle. Since only very low volumes of reagents are added to the initial sample to establish the binding conditions of the nucleic acids, the maximum handling volume of automated systems can be effectively used for as much of the initial sample as possible. The method according to the present invention allows to maximize the nucleic acid yield by allowing to process larger volumes and by achieving a high recovery rate and thus, a high yield of extracted extracellular nucleic acids. Hence, the method according to the present invention is especially suitable for isolating extracellular nucleic acids from biological samples such as body fluids which comprise extracellular nucleic acids in low amounts such as e.g. <100 ng/ml sample. The method according to the present invention can be used to isolate extracellular nucleic acids so that they are directly available for downstream applications such as e.g. subsequent analysis methods, e.g. in order to amplify, identify, quantify and/or detect the presence or absence of a certain target nucleic acid within the extracted extracellular target nucleic acid population. Thus, despite the fact that the method according to the present invention is very simple and rapid, the isolated nucleic acids are sufficiently pure to be used in standard downstream applications such as e.g. analysis and detection assays as is shown in the examples.

Furthermore, the isolation method according to present invention can also be used as a pretreatment protocol for isolating and thus concentrating extracellular nucleic acids from large sample volumes. The respectively concentrated extracellular nucleic acids can then optionally be further purified using a standard nucleic acid isolation protocol. Performing the method according to the present invention as a concentration protocol to reduce the sample volume for a subsequent purification step has the advantage that time and costs can be saved and the yield of extracellular nucleic acids can be increased because larger initial sample volumes can be processed. Thus, the present method can also be used as a pre-treatment protocol in order to concentrate extracellular nucleic acids from a large sample volume to a smaller sample volume that allows the use of standard nucleic acid isolation, respectively purification protocols that can be run e.g. on established automated systems which have limitations with respect to the sample volume they can handle. The incorporation of a respective pre-extraction, respectively concentration step also allows to establish, respectively improve the routine testing for extracellular nucleic acids using automated systems because the isolation result, in particular with respect to the yield, is improved.

The method according to the present invention can be performed manually, or by using automated systems. Manual methods have the advantage that usually larger sample volumes can be processed (automated systems usually have due to their design a certain limit with respect to the volume they can process). Automated systems have the advantage that many samples can be processed at the same time and that automated systems are less error prone, because handling errors are avoided. The limitations with respect to the sample volume can be overcome to a certain extent by splitting the original sample, processing the sample portions in parallel and reunifying either the eluates or the anion exchange material prior to elution. According to one embodiment, extracellular nucleic acids comprised in a first sample are bound to the solid phase according to the method of the present invention, in particular the method as defined in claim 1. Preferably, particles, in particular magnetic particles are used as solid phase. Said solid phase with the bound extracellular nucleic acids is then contacted with the binding mixture of a second sample, wherein said second sample preferably is a split portion of the same original sample, i.e. the original sample was split into the first and second sample. Thereby, the solid phase of the first sample is unified with the solid phase of the second sample and the unified solid phases are then further processed. This sample splitting and reunifying of either eluates and/or solid phases allows to easily process larger sample volumes using an automated system which can only process a limited sample volume.

A further advantage when using the present method is that the recovery rate remains substantially the same, irrespective of the dilution of the extracellular nucleic acids in the sample. Thus, the present method allows to isolate the extracellular nucleic acids with basically the same yield, respectively recovery rate (see examples), irrespective of whether the same amount of nucleic acids is found in 1 ml, 5 ml, 10 ml or 25 ml sample. This is a particular advantage when isolating low abundance extracellular nucleic acids from large sample volumes as a low concentration does not hamper the efficient nucleic acid isolation when using the method according to the present invention.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA and mixtures thereof. Examples of typical extracellular nucleic acids that are found in the cell-free fraction (respectively portion) of a biological sample such as a body fluid or a sample derived from a body fluid such as e.g. blood plasma include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogenic nucleic acids released into the extracellular nucleic acid population e.g. from prokaryotes (e.g. bacteria), viruses or fungi. According to one embodiment, the extracellular nucleic acids are obtained from a body fluid or a sample derived from a body fluid as biological sample such as e.g. blood, plasma, serum, saliva, urine, liquor, cerebrospinal fluid, sputum, lachrymal fluid, sweat, amniotic or lymphatic fluid; preferably the extracellular nucleic acids are obtained from the cell-free or cell-depleted portion of the foregoing samples. Herein, we refer to extracellular nucleic acids that are obtained from a circulating body fluid or a sample derived from a circulating body fluid, in particular from the cell-free or cell-depleted portion of a circulating body fluid as circulating extracellular or circulating cell-free (ccf) nucleic acids. According to one embodiment, the term extracellular nucleic acid in particular refers to mammalian extracellular nucleic acids, preferably disease-associated or disease-derived extracellular nucleic acids such as tumor-associated or tumor-derived extracellular nucleic acids, extracellular nucleic acids released due to inflammations or injuries, in particular traumata, extracellular nucleic acids related to and/or released due to other diseases, or extracellular nucleic acids derived from a fetus. The term "extracellular nucleic acids" or "extracellular nucleic acid" as described herein also refers to extracellular nucleic acids obtained from other samples, in particular biological samples other than body fluids.

As discussed above, the method according to the present invention is also useful for isolating viral nucleic acids as one embodiment of extracellular nucleic acids. The efficiency of the present method results in a higher sensitivity of the subsequent downstream detection methods, so that diagnostically important viruses such as HIV or HCV can be detected more reliably e.g. in blood donations. Furthermore, the monitoring of anti-viral therapy can be improved due to a lower limit of virus detection. When aiming at isolating viral nucleic acids, it is preferred to use the present method as pre-treatment protocol for concentrating the contained viral nucleic acids prior to performing an additional nucleic acid isolation protocol such as e.g. a standard viral nucleic acid isolation protocol.

The term "binding mixture" as used herein refers to the composition that is prepared for the binding step and which allows to bind the extracellular nucleic acids comprised in the sample to the anion exchange groups of the solid phase. Hence, the binding mixture provides appropriate conditions for binding the extracellular nucleic acids to the solid phase. The binding mixture comprises the sample and the reagents and/or compounds that were added to the sample in order to prepare the sample for the binding step. E.g. acidifying reagents and/or compounds may be added to the sample to establish the first pH value. According to the present invention, preferably at least 85% of the volume of the binding mixture is provided by the sample, respectively the stabilized sample if a stabilized sample, e.g. a stabilized blood plasma or serum sample is processed. Preferably, at least 90%, at least 92%, at least 94%, at least 95% and most preferably at least 97% of the volume of the binding mixture is provided by the sample, respectively the optionally stabilized sample. This ensures that the binding mixture consists predominantly of the extracellular nucleic acid containing sample (which is optionally stabilized). This allows to process large sample volumes (see above). The term "binding mixture" as used herein does not include the solid phase. Hence, the potential volume contribution of the solid phase is not considered in the above volume specifications. Whether the solid phase contributes at all to the volume of the binding mixture also depends on the solid phase that is used for binding the extracellular nucleic acids. Suitable examples of solid phases are described below.

According to one embodiment, the binding mixture is prepared by adjusting the pH of the sample to the first pH. This can be achieved by adding acidifying compounds and/or reagents. Suitable examples of acidifying reagents include but are not limited to acids, acidic buffering agents such as carboxylic acids, e.g. acetic acid, sodium acetate/acetic acid buffers, citric acid/citrate buffers, maleic acid, malonic acid, tartaric acid, HCl, $HClO_4$, $HClO_3$, formic acid, boric acid, $H_2SO_4$, $H_2SO_3$, acidic phosphoric acid/phosphate buffer systems, MES or other water-soluble inorganic or organic acids. In a preferred embodiment, an acidifying solution, preferably an acidifying buffer is added to the sample as acidifying compound and/or reagent to establish the binding conditions in the binding mixture. The acidifying solution may contain a buffering substance capable of adjusting the pH of the resulting binding mixture to the first pH. It may additionally comprise a salt, preferably in solution, in particular in an aqueous solution. Preferably, the acidifying solution comprises a buffering substance or a combination of different buffering substances, preferably solved in water. A particularly preferred example of an acidifying solution is an aqueous solution of a sodium acetate/acetic acid buffer, preferably in a concentration of from 0.5 to 5 M, more preferably 0.5 to 4 M, 0.5 to 3 M and more preferably about 1 to 2 M, preferably having a pH value in the range of about 2 to about 5, more preferably about 4. The acidifying solution preferably is added to the sample in a ratio (volume (acidifying solution): volume (sample, respectively optionally stabilized sample)) of from about 1:10 to about 1:1000 by volume, preferably in a ratio of from about 1:100 to about 1:20 by volume, more preferably in a ratio of about 1:30, most preferably in a ratio of about 1:40 by volume. Other suitable buffers systems include e.g. potassium acetate/acetic acid, sodium (or potassium) citrate/citric acid and sodium (or potassium) phosphate/phosphoric acid. The respective ratios are in particular useful when processing body fluids (or samples derived from body fluids) as samples, such as e.g. blood, plasma or serum.

According to one embodiment, the first pH is below the pKa value of a protonatable group of the anion exchange groups that are provided on the surface of the solid phase. The first pH used for binding of the nucleic acids to the solid phase is preferably below the pKa value of the protonatable group of the anion exchange group. If the anion exchange group comprises more than one protonatable group, the first pH preferably is below the pKa of at least one protonatable group. Preferably, the first pH is at least 0.5 units below the pKa value, more preferably at least 1 unit, at least 1.5 units, at least 2 units, at least 2.5 units, and most preferably at least 3 units below said pKa value. Preferably, the pH is above 4.

The first pH value that is used respectively is suitable for binding the extracellular nucleic acids to the anion exchange groups of the solid phase also depends on the nature of the anion exchange groups and/or their density of the anion exchange groups on the surface of the solid phase. Also the used salt concentration may influence the binding. Suitable pH values for the first pH value can be determined by the skilled person. According to one embodiment, the first pH lies in the range of from about 4 to about 7, more preferably in a range selected from 4 to 6.5; 4.5 to 6.5; 5 to 6.5 and 5 to 6. The respective pH values are in particular optimized for binding nucleic acids such as DNA and/or RNA when using the anion exchange particles described in the examples. Preferably, the pH of the binding mixture is ≤6.5 and preferably ≤6. When aiming at isolating extracellular RNA, it is preferred to use a stronger acidic first pH value of ≤5.5 or ≤5 as this might increase the RNA yield. The acidification of the sample establishes the first pH for binding the extracellular nucleic acids to the anion exchange groups of the solid phase. The acidification furthermore processes the sample and thus may improve binding, e.g. by releasing extracellular nucleic acids such as e.g. DNA that may be trapped e.g. in histone complexes.

Binding occurs for a time sufficient to allow substantial binding of the extracellular nucleic acids to the solid phase. The suitable, respectively necessary incubation time depends on the type and amount of solid phase and anion exchange groups used, the sample volume and the concentration of extracellular nucleic acids in the sample. E.g. shorter incubation times can be sufficient, if a solid phase is used which has a high density of anion exchange groups and hence, tightly binds the extracellular nucleic acids. Longer incubation times ensure that the nucleic acids bind highly efficient to the solid phase, thereby allowing to maximize the extracellular nucleic acid recovery from the sample. According to some embodiments, the incubation time is selected from at least 1 min., at least 2 min., at least 5 min., at least 10 min, at least 15 min and more preferably at least about 20 min.

In step (b) of the method according to the present invention the extracellular nucleic acids that are bound to the solid phase are separated from the remaining sample. For this purpose, any means known in the art can be used. Suitable means also depend on the type of the solid phase that is used for binding and include but are not limited to magnetic separation if a magnetic solid phase is used, centrifugation e.g. if non-magnetic particles or a membrane is used, sedimentation, the application of a vacuum, filtration or chromatography. Suitable solid phases are described below and the skilled person is familiar with the handling of the respective solid phases.

In preferred embodiments, the entire method for isolating nucleic acids is performed at room temperature.

The sample, the solid phase and the acidifying compound(s) and/or reagent(s) can be contacted in any order. In a preferred embodiment, at least one acidifying compound and/or reagent is added to the sample in order to establish the first pH and hence the binding conditions. The resulting binding mixture is then contacted with the solid phase to bind the extracellular nucleic acids to the solid phase. Optionally, further pH adjustments can be made after contacting to optimize the binding conditions or to establish the desired first pH. However, it is also within the scope of the present invention, also depending on the type of solid phase used, to provide the solid phase first and then add the sample and at least one acidifying compound and/or reagent in any order. Any suitable contacting order can be used that allows to bind the extracellular nucleic acids to the solid phase. After step (b), one or more washing steps may optionally be performed as step (c). According to one embodiment, at least one washing solution is contacted with the solid phase that carries the bound extracellular nucleic acids. In order to ensure maximum recovery of the bound nucleic acids, the washing conditions preferably are chosen such that no significant amount of nucleic acid bound to the nucleic acid binding matrix is removed therefrom during washing. The washing buffer preferably is an aqueous solution and may contain a surfactant. Suitable surfactants include but are not limited to polyoxyethylene-based non-ionic surfactants, preferably selected from the group consisting of polyoxyethylene fatty alcohol ethers, polyoxyethylene alkylphenyl ethers, and polyoxyethylene-polyoxypropylene block copolymers. Preferred examples are TritonX-100 or Brij58, for example at a concentration of about 0.01%-1%. Suitable washing solutions are also known in the prior art and thus, do not need any further description here. Washing is particularly recommended, if the isolated extracellular nucleic acids are e.g. supposed to be directly analysed and/or detected e.g. in a diagnostic assay without further purification. If the isolated extracellular nucleic acids are supposed to be directly analysed using methods that are e.g. sensitive to potential impurities (such as e.g. PCR methods), it is recommended to perform at least two washing steps. According to one embodiment, preferably two different volumes of wash solutions are used. Here, the volume of the first washing solution is preferably larger than the volume of the second washing solution. Washing is, however, not necessary if subsequently a detection and/or analysis method is used that is rather insensitive to impurities. Furthermore, if the isolation method according to the present invention is used to enrich and thus concentrate the extracellular nucleic acids in a small sample volume as preparation for a subsequent nucleic acid isolation method, respectively purification protocol, washing is also not mandatory. Performing a respective subsequent isolation protocol is particularly recommended if e.g. viral nucleic acids are the main target within the population of extracellular nucleic acids.

According to one embodiment, the method for isolating extracellular nucleic acids further comprises a step (d) of eluting extracellular nucleic acids from the solid phase. Generally any suitable elution method can be used. Preferably, elution is achieved by changing the pH value. Thus, according to one embodiment, elution occurs at a second pH which is higher than the first pH that was used for binding the extracellular nucleic acid to the solid phase. The choice of the second pH value that is suitable for eluting the extracellular nucleic acids from the anion exchange groups inter alia depends on the nature of the anion exchange groups present on the solid phase, the density of the anion exchange groups on the surface of the solid phase and the ionic strength of the elution solution. Suitable pH values for the second pH can be determined by the skilled person. The second pH preferably is at least 0.5 units higher than the first pH, at least 1 unit higher than the first pH, more preferably at least 1.5 units higher or at least 2 units higher than the first pH. The second pH may be below, at or above the pKa of a protonatable group of the anion exchange group. However, preferably, it is at least 1 unit below the pKa, more preferably at least 1.5 units below the pKa or at least 2 unit below said pKa. Preferably, the elution is performed at a second pH≥8. Preferably, elution occurs at a pH range selected from the group consisting of pH≥8 and ≤14; pH≥8 and ≤12.6; pH≥8 and ≤12; ≥8 and ≤11; pH≥8 and ≤10 and 8 and ≤9. The pH value that is used for elution may also depend on the intended further application of the eluate. Lower elution pH values can be advantageous because a respective lower pH value is more compatible with many common downstream reactions (e.g. PCR). E.g. stronger alkaline pH values, such as a pH value of at least 12, can be used and are advantageous, e.g. if single-stranded DNA is needed or RNA contaminations have to be reduced. According to one embodiment, elution is achieved by using a ≤1 mol/l sodium hydroxide solution. For certain applications, e.g., the subsequent treatment of the eluted DNA with bisulfite reagents in order to analyze DNA methylation patters, it may also be beneficial to elute the nucleic acids at pH≥12 and ≤14 in order to denature the eluted DNA. If elution occurs at a higher pH value (e.g. 10 or higher), the eluate comprising the nucleic acids can be neutralized e.g. if a respective neutral pH value is beneficial for the intended downstream applications. Furthermore, it was found that RNA can be eluted at lower pH values. E.g. when using a solid phase carrying polyethylenimine groups (see examples), RNA could be efficiently eluted at a pH value of 8, wherein for DNA a higher pH value of above 12 was more suitable. If intending to recover RNA in the elution step it is preferred not to use high pH values because the RNA could be damaged. High pH values above pH 9 can be e.g. avoided by increasing the salt concentration in the elution solution if the elution strength provided by the second pH is not sufficient for an efficient elution.

Elution preferably is achieved by contacting the extracellular nucleic acids that are bound to the solid phase with an elution solution. The elution solution preferably comprises a buffering substance which is capable of adjusting the second pH. In particular, biological buffers can be used. A suitable example is tris(hydroxymethyl)aminomethane (Tris) in a concentration of about 1 mM to 1M, preferably 10 mM to 500 mM, more preferred 50 mM to about 250 mM, most preferred 75 mM to 150 mM, adjusted to the desired pH using e.g. HCl. However, according to one embodiment, the free base of the buffering substance, e.g. Tris as free base, is used. It can be used in the aforementioned concentration ranges. According to one embodiment, an elution solution comprising Tris as free base is used. The pH value of said elution solution containing the free base may be e.g. in a range of 10 to 10.5. According to one embodiment, said elution solution does not comprise salts, in particular does not comprise alkali salts or earth alkaline salts. As is shown by the examples, using a respective elution solution comprising Tris as free base without additional salts allows to selectively elute predominantly small nucleic acids having a length of 300 nt or less, preferably 250 nt or less, more preferred 200 nt or less, 150 nt or less or even 100 nt or less as will also be explained subsequently and as is shown in the examples. Therefore, these elution conditions can be used to enrich respective short nucleic acids in the eluate versus longer nucleic acids. By adding salt to the elution solution comprising Tris as free base it is also possible to elute longer nucleic acids. The salt concentration can be adjusted if longer nucleic acids are of interest, the concentration would depend on the desired cut-off value. The elution solution preferably is an aqueous solution comprising the buffering substance and optionally further components such as a salt, in particular an alkali salt such as sodium chloride or potassium chloride, for example in a concentration of about 0.05 to about 0.5 M, preferably about 0.1 to about 0.2 M, more preferably about 0.16 M. The used salt concentration has an influence on the elution efficiency, in particular the elution efficiency of longer nucleic acids. The higher the salt concentration, the more efficient is the elution of longer nucleic acids. Therefore, increasing the salt concentration increases the elution efficiency for longer nucleic acids. Therefore, by controlling the salt concentration in the solution buffer it is possible to control the size of the nucleic acids to be eluted. E.g. increasing the concentration of the salt, in particular of an alkali salt such as sodium chloride or potassium chloride, in the elution solution to 75 mM or above, results in that nucleic acids having a size of at least 500 nt become eluted with a recovery rate above 40%. Other possible buffers include but are not limited to HEPES, Tris-Borate and MOPS. Hence, preferably elution takes place at a low salt condition. Using a low salt concentration has the advantage that the eluate can be directly used in a downstream assay such as e.g. a PCR reaction. According to one embodiment, an elution solution is used which comprises 100 mM Tris-HCL (containing 0.5-1.5%, preferably 0.9% sodium chloride, pH 9). However, it is also within the scope of the present invention to use higher salt concentrations, in particular in order to increase the ionic strength to avoid high pH values e.g. above 10 or above 12 (see above) e.g. if such a high pH value is not compatible with the intended downstream reactions. According to one embodiment, an elution solution is used which comprises an alkali hydroxide such as sodium hydroxide or potassium hydroxide. As is shown by the examples, by varying the concentration of alkali hydroxide in the elution solution it is also possible to influence the size of the nucleic acids that are predominantly eluted. Increasing the concentration of alkali hydroxide in the elution solution increases the size of the nucleic acids that are eluted. Preferably, at least 50%, more preferably at least 70%, at least 80%, at least 85%, at least 90%, at least 95%, at least 97% or at least 98% of the extracellular nucleic acid bound to the solid phase or of the extracellular nucleic acids having a desired size range is eluted therefrom in step (d). Elution can also be assisted by heating and/or shaking.

Furthermore, the elution efficiency can be increased in particular for eluting longer nucleic acids by including in the elution solution an anionic compound which comprises at least two anionic groups. A respective anionic compound supports the disruption of the nucleic acid/anion exchange complex and therefore supports the elution. As anionic compound comprising at least two anionic groups, for example carboxylic acids such as oxalic acid, mellitic acid, pyromellitic acid and citric acid can be used. Furthermore, also polymeric anionic compounds can be used such as for example polyacrylic acid (PAA), polymethacrylic acid (PMA), polyglutamic acid (PGA) and dextran sulfate. Respective anionic compounds are also described in WO 2011/037692. As is shown by the examples, the elution efficiency can be enhanced when adding a respective anionic compound.

According to one embodiment, the present invention provides a method for separating nucleic acids by size. Surprisingly, the present inventors have found that when using an anion exchange matrix for binding nucleic acids, the bound nucleic acids can be eluted from the matrix depending on their size simply by adjusting respectively varying the elution pH. At a lower elution pH, only small nucleic acid molecules will elute from the anion exchange matrix. When the elution pH is elevated, also larger nucleic acids can be eluted. This allows to separate the bound extracellular nucleic acids by size. In particular, it was found that only small changes in the elution pH are necessary to obtain this size fractionating effect.

According to one embodiment, only a part, respectively portion of the extracellular nucleic acids is eluted from the solid phase at a second pH which is higher than the first pH, wherein the average length of the extracellular nucleic acids eluted from the solid phase is shorter than the average length of the extracellular nucleic acids which remain bound to the solid phase. According to one embodiment, the second pH is in the range of from about 7.5 to 10.5, preferably from about 8 to 10, 8.2 to 9.5, preferably about 8.5 to 9. As is shown by the examples, using an elution solution having a respective pH value allows to achieve a size selective elution, wherein the average length of the extracellular nucleic acids eluted from the solid phase is shorter than the average length of the extracellular nucleic acids which remain bound to the solid phase. The cut-off value can be adjusted by adjusting the elution conditions. In particular the pH value and the salt concentration of the elution solution are decisive features that have an influence on the cut-off value and thus on the length of the nucleic acids that are predominantly eluted.

Depending on the size distribution of nucleic acids in a nucleic acid population, such as e.g. the bound or the eluted nucleic acids, the average nucleic acid length in a population of nucleic acid molecules may refer to that nucleic acid length at which half of the nucleic acid molecules in the population have a shorter length and the other half of the nucleic acid molecules have a greater length than the average nucleic acid length. However, the average nucleic acid length in a population of nucleic acid molecules may also refer to that nucleic acid length that occurs most frequently in the respective nucleic acid population. The latter option to determine the average nucleic acid length will usually be more appropriate and thus preferred for skewed nucleic acid populations wherein a certain nucleic acid size or a certain nucleic acid size range prevails. The length of the nucleic acids that are eluted and the length of the nucleic acids that remain bound to the anion exchange matrix can be controlled and thus varied by adjusting the elution conditions. Thus, it is possible to adjust the size, respectively the size range of the eluted and bound nucleic acids thereby allowing to obtain nucleic acids of a preselected target size, respectively preselected target size range. Preferably, the difference between the average length of the nucleic acids eluted from the solid phase with said second pH and the average length of the nucleic acids remaining bound to the solid phase is at least about 50 nt, at least about 75 nt, at least about 100 nt, at least about 150 nt, at least about 200 nt, at least about 250 nt, at least about 300 nt, at least about 350 nt or at least about 400 nt. According to one embodiment, the average length of the extracellular nucleic acids eluted from the solid phase in the first elution step at the second pH value is in the range of from up to about 700 nt, up to about 600 nt, from about 10 nt to about 500 nt, 10 nt to about 400 nt, 15 nt to about 300 nt, preferably from about 20 nt to about 250 nt, from 20 nt to 200 nt or from about 50 nt to about 150 nt. Furthermore, the average length of the nucleic acids remaining bound to the solid phase in this first elution step is at least about 200 nt, preferably at least about 250 nt, at least about 300 nt, at least about 400 nt, at least about 500 nt, at least about 600 nt, at least about 700 nt, at least about 1000 nt or at least about 1500 nt. In preferred embodiments, extracellular nucleic acids having a length of up to about 1000 nt, up to about 700 nt, up to about 600 nt, up to about 500 nt, preferably up to about 400 nt, up to about 300 nt, up to about 250 nt or up to about 200 nt are predominantly eluted from the solid phase in the first elution step at the second pH and/or nucleic acids having a length of about 200 nt or more, 300 nt or more, 350 nt or more, 400 nt or more, 500 nt or more, preferably about 700 nt or more, about 800 nt or more or about 1000 nt or more predominantly remain bound to the solid phase in said first elution step. As described above, the length of the nucleic acids is indicated.

Hence, if the extracellular nucleic acid is a double stranded molecule (e.g. DNA) the above indications with respect to the nt length refers to bp. The term "predominantly eluted" in this respect in particular refers to an elution of at least 50%, preferably at least 60%, at least 70%, at least 80%, at least 90% or at least 95% of the designated group of nucleic acid molecules from the nucleic acid binding matrix. Likewise, the term "predominantly remain bound" in this respect in particular refers to an elution of less than 50%, preferably less than 40%, less than 30%, less than 20%, less than 10% or less than 5% of the designated group of nucleic acid molecules from the nucleic acid binding matrix.

Selective elution of the short nucleic acids can be achieved in step (d) by adjusting the concentration of positive charges on the surface of the solid phase so that only the longer nucleic acid molecules remain bound to the matrix during step (d) while the smaller nucleic acids are eluted. The cut-off value can be controlled by the choice of the pH value that is used during elution. The adjustment of the positive charges can be controlled by the pH used during the elution step. In particular, elution is performed by addition of an elution solution comprising a buffering substance which is capable of providing the second pH during the elution step. In preferred embodiments, the elution is performed under low salt conditions. In particular, the elution solution does not comprise more than 0.5M salt, not more than 0.3 M salt, preferably not more than 0.27 M salt, more preferably not more than 0.25 M salt.

In specifically preferred embodiments, a solid phase comprising anion exchange groups is used which comprise diethylamino groups, preferably diethylaminopropyl groups. As is shown in the examples, a solid phase comprising respective anion exchange groups has significant advantages. First, excellent recovery rates are achieved which are also superior to other anion exchange surfaces. Second, mild elution conditions can be used in particular for eluting small nucleic acids what is advantageous for many downstream applications of the isolated extracellular nucleic acids. Third, respectively functionalized solid phases are particularly well suitable for enriching short extracellular nucleic acids by performing a size selective elution. A solid phase comprising anion exchange groups which comprise diethylamino groups, preferably diethylaminopropyl groups, advantageously allows to regulate the size of the eluted nucleic acids by varying the pH value and/or the salt concentration. As is shown by the examples, the cut-off values can be adjusted in a narrow range, which results in a reliable, size selective elution. According to one embodiment, the second pH in the embodiment wherein a solid phase comprising anion exchange groups is used which comprise diethylamino groups, preferably diethylaminopropyl groups, is in the range of from about 7.5 to 10.5, preferably from about 7.5 to 9.5, from about 7.5 to about 9.0, preferably about 8.0-8.5. In particular, an elution solution can be used which comprises a buffering substance for adjusting said pH value and optionally a salt such as sodium chloride, preferably in a concentration of from about 0.1 to about 0.2 M, more preferably about 0.16 M. Furthermore, as is shown by the examples, the size of the eluted nucleic acids can also be varied and thus controlled by the amount of salt comprised in the elution solution. A higher amount of salt results in an elution of larger nucleic acids.

Performing a size selective elution has several advantages. First, it is possible to selectively elute extracellular nucleic acids, as extracellular nucleic acids predominantly have a small size as is described in the introduction. Thus, elution conditions can be used, wherein high molecular weight nucleic acids such as for example genomic DNA or other longer intracellular nucleic acids, are not recovered by a respective size selective elution procedure. This is an important advantage, as it reduces or can even avoid a contamination of the isolated extracellular nucleic acids by residual amounts of intracellular nucleic acids such as genomic DNA which may be present even in cell-depleted or cell-free samples, because intracellular nucleic acids can be released e.g. by decaying or disrupted cells what can happen during storage and/or during the cell depletion process. The method according to the present invention allows to eliminate respective intracellular nucleic acid contaminations such as e.g. genomic DNA in the isolated nucleic acids when adjusting the elution condition as described herein such that predominantly nucleic acids having a size a 1,500 nt or less, preferably 1,000 nt or less, are eluted and thus recovered. The possibility to eliminate genomic DNA by adjusting the elution conditions is an important advantage as this allows to skip the ultracentrifugation step that is usually performed at 16 000 g to further clear the plasma in order to remove respective genomic DNA contaminations that might still be associated with comprised cell debris. This saves hands-on time and equipment. Furthermore, as is shown by the examples, by adjusting the pH value and/or the salt concentration of the elution buffer it is even possible to fractionate extracellular nucleic acids having a size of 1,000 nt or less by size. Thereby, it can be determined which population of small extracellular nucleic acids having a size of 1000 nt or less is eluted and e.g. it is possible to predominantly elute and thus recover nucleic acids having a size of 500 nt or less, 400 nt or less, 300 nt or less, 200 nt or less or even 150 nt or less. Furthermore, as described herein, a second elution step can also be performed, if, for example, also longer nucleic acids should be of interest but are supposed to be eluted and thus recovered as separate fraction. In this second elution step conditions are used which allow to elute longer nucleic acids. Suitable conditions are described herein. Therefore, because the method according to the present invention provides the possibility to control the size of the eluted nucleic acids by varying the elution conditions, it is very flexible. Particularly suitable elution conditions for isolating small nucleic acids having a size of 1,000 nt or less, 700 nt or less, 600 nt or less, 500 nt or less, 400 nt or less, 300 nt or less, 200 nt or less or even 100 nt or less are also described in the examples. In particular, using an elution solution which comprises a buffering substance such as Tris at a pH value that lies in a range of 8 to 10.5 allows to selectively elute nucleic acids which have a size of 1,000 nt or less, preferably 700 nt or less or even 500 nt or less. For example, using an elution solution comprising Tris as free base and a pH of approximately 10 to 10.5 allows to selectively elute nucleic acids having a size of less than 500 nt, and even less than 300 nt. Furthermore, using an elution solution comprising alkali hydroxide, for example sodium hydroxide or potassium hydroxide, allows to selectively elute small nucleic acids having a size of less than 500 nt, preferably less than 300 nt. As is shown by the examples, the cut-off value that is achieved depends on the amount of alkali hydroxide used. The higher the concentration of alkali hydroxide in the elution solution, the larger is the size of the eluted extracellular nucleic acids. Therefore, by adjusting the hydroxide concentration it is possible to adjust the size of the eluted nucleic acids. When using Tris in form of a buffer, it is preferred to use a pH value that lies in a range of 8 to 9.5, preferably 8.5 to 9. As is shown by the examples, using a respective elution solution allows to selectively elute small nucleic acids. The cut-off value can also be influenced by incorporating a salt into the elution solution, preferably an alkali metal salt such as sodium chloride or potassium chloride. As is shown by the examples, adjusting the concentration of the salt in the elution buffer has a strong influence on the size of the nucleic acids that are eluted. The higher the salt concentration, the longer are the extracellular nucleic acids that are eluted from the solid phase. Therefore, as described herein, a size selective elution is possible by adjusting the pH value, the salt concentration and/or the incorporation of further additives that influence the elution efficiency. Here, the skilled person is able to provide elution solution having a desired cut-off value following the teachings and guidance given in the present application and in particular the examples.

When performing a size selective elution it is preferred that the solid phase carries anion exchange groups, which comprise protonatable groups, and the pKa value of the protonatable groups is in the range of from 8 to 12, more preferably from 9 to 11. The anion exchange groups may comprise nitrogen atoms, preferably the anion exchange groups are derived from amines. In particular, the anion exchange groups are tertiary amino groups, preferably dialkylamino groups, more preferably diethylamino groups and especially preferably diethylaminopropyl groups. As is shown in the examples, respective tertiary amines show particular good recovery rates and furthermore, allow a reliable size selective elution with well defined cut-off values. Therefore, it is preferred to use tertiary amino groups, preferably dialkylamino groups, more preferably diethylamino groups and especially preferably diethylaminopropyl groups when intending to perform a size selection, respectively size fractionation, during elution. In certain embodiments, the solid phase material has a silicon containing surface such as a polysilicic acid surface and the anion exchange groups are coupled to said surface using a silane group, i.e. via silanization. E.g. the solid phase may comprise a silicon containing surface, preferably a polysilicic acid surface and may be derivatized with a silane compound comprising the anion exchange groups, preferably with diethylaminopropyl trimethoxysilane. Preferably, the surface of the solid phase is not derivatized with another silane compound. Most preferred, magnetic particles are used as solid phase.

According to one embodiment, the size fractionating elution step comprises the following steps:
aa) at least a portion of the extracellular nucleic acids bound to the solid phase is eluted from the solid phase at a second pH which is higher than the first pH, wherein the average length of the nucleic acids eluted from the solid phase in this step is shorter than the average length of the nucleic acids which remain bound to the solid phase;
bb) optionally eluting nucleic acids which remain bound to the solid phase in step aa) from the solid phase. Here, any elution method can be used.

Preferably, elution is achieved in step bb) using a third pH which is higher than the second pH. The third pH preferably may be chosen such that essentially all of the nucleic acids which remained bound to the solid phase in step aa) are eluted therefrom in step bb). The term "essentially all" in this respect in particular refers to at least 70%, preferably at least 80%, at least 85%, at least 90%, at least 95%, at least 97% or at least 98% of the bound nucleic acids. The third pH preferably is at least 0.1 units, at least 0.2 units, at least 0.3 units, at least 0.5 units, at least 0.75 units, at least 1 unit, at least 1.25 units, at least 1.5 units, at least 1.75 units or at least 2 units higher than the second pH. Furthermore, the difference between the second pH and the third pH preferably is 3 units or less, more preferably 2 units or less, 1.5 units or less, 1 unit or less, 0.7 units or less or 0.5 units or less. It was found that small differences such as e.g. a difference in 0.5 pH units is already sufficient for a size selective elution.

According to one embodiment, the salt concentration and/or the temperature during the elution of step (bb) according to one embodiment does not significantly differ and in particular is not significantly higher than during the elution of step (aa). Preferably, the salt concentration does not differ by more than 100 mM, more preferably not more than 50 mM and most preferably not more than 25 mM. Furthermore, the temperature used for elution according to one embodiment does not differ by more than 10° C., more preferably not more than 5° C. or not more than 2.5° C. Moreover, preferably also the other elution conditions except for the pH value preferably are similar in the first and second elution step.

Further processing steps can be performed in the method according to the present invention prior to step (a) and/or between steps (a) and (b) and any subsequent steps (c) and (d), (if respective optional steps (c) and (d) are performed). According to one embodiment, no sample digestion step is performed prior to step (a), wherein reagents are used that increase the volume of the sample (which is optionally a stabilized sample) by more than 15%. Preferably, no sample digestion step is performed prior to step (a), wherein reagents are used that increase the volume of the sample by more than 10%, more preferred by more than 5%, most preferred no reagents are used for digesting the sample that increase the volume by more than 2.5%. Thereby it is ensured that the binding mixture predominantly consists of the sample material which comprises the extracellular nucleic acids (which is optionally stabilized) thereby ensuring maximum yield of the extracellular nucleic acids as is explained above.

Depending on the sample type to be processed it was found that the isolation results can vary due to variations in the composition of the sample. The homogeneity of the isolation results can be improved by pretreating the sample (which optionally is a stabilized sample) with appropriate means. Therefore, it is within the scope of the present invention to perform a sample pretreatment step prior to step (a). However, said pretreatment step should not considerably add to the volume of the sample and hence, to the volume of the binding mixture. Preferably, the contribution of the reagents used during a respective sample pretreatment step to the volume of the binding mixture is less than 5%, preferably less than 2.5%, more preferably less than 2%, less than 1.5% or less than 1%, if volume increasing reagents are at all used (see above). Suitable pretreatment steps include but are not limited to mechanical, chemical, physical or enzymatic actions on the sample. Examples of pretreatment steps include but are not limited to grinding the sample in a bead mill, the application of ultrasound, heating, freezing and thawing, the addition of detergents and/or the addition of protein degrading compounds such as e.g. protein degrading enzymes, e.g. hydrolases or proteases. According to one embodiment, a pretreatment step is performed prior to step a), wherein at least one protein degrading compound, preferably a proteolytic enzyme, preferably a protease such as a proteinase, and/or an detergent is added to the sample prior to step a).

According to one embodiment, up to step c) no chaotropic salts are used for processing the sample.

Preferably, the sample is a biological sample which comprises extracellular nucleic acids. The sample may be e.g. selected from the group consisting of whole blood, plasma, serum, sputum, lachrymal fluid, lymphatic fluid, urine, sweat, liquor, cerebrospinal fluid, ascites, milk, stool, bronchial lavage, saliva, amniotic fluid, nasal secretions, vaginal secretions, semen/seminal fluid, wound secretions and excretions, and cell culture supernatants and supernatants obtained from other swab samples. According to one embodiment, the sample is a body fluid, a body secretion or body excretion, preferably a body fluid or a sample that is derived from a body fluid that comprises extracellular nucleic acids, most preferably whole blood, plasma or serum. The sample comprises extracellular nucleic acids. According to another embodiment, the sample is a non-fluid sample derived from a human or animal, such as e.g. stool, tissue or a biopsy sample. Other examples of samples that can be processed with the method according to the present invention include but are not limited to biological samples cell suspensions, cell cultures, supernatant of cell cultures and the like, which comprise extracellular nucleic acids.

According to one embodiment, the sample comprising the extracellular nucleic acids is a cell-free or cell-depleted sample. A respective cell-free or cell-depleted sample can be obtained e.g. from a cell-containing sample by using appropriate technologies to remove cells. A typical example is blood plasma or blood serum which can be obtained from whole blood. If the sample comprises large amounts of cells as is e.g. the case with whole blood, the cells are separated from the remaining sample in order to obtain a cell-free, respectively cell-reduced fraction of the sample which comprises the extracellular nucleic acids. Thus, according to one embodiment, cells are removed from the cell-containing sample to provide the cell-free or cell-depleted sample which comprises the extracellular nucleic acids and from which the extracellular nucleic acids are isolated using the method according to the present invention. This cell removal step is only optional and e.g. may be obsolete if samples are processed (respectively are obtained for processing) which merely comprise minor amounts of residual cells such as e.g. plasma or serum. However, in order to improve the results it is preferred that also respective remaining cells (or potentially remaining cells) are removed as they might contaminate the extracellular nucleic acid population during the isolation. Depending on the sample type, cells, including residual cells, can be separated and removed e.g. by centrifugation, preferably high speed centrifugation, or by using means other than centrifugation, such as e.g. filtration, sedimentation or binding to surfaces on (optionally magnetic) particles if a centrifugation step is to be avoided. Respective cell removal steps can also be easily included into an automated sample preparation protocol. Respectively removed cells may also be processed further e.g. in order to analyse the intracellular nucleic acids. The cells can e.g. be stored and/or biomolecules such as e.g. nucleic acids or proteins can be isolated from the removed cells.

According to one embodiment, the sample from which the extracellular nucleic acids are isolated is a stabilized sample. Many samples such as blood samples or samples derived from blood such as plasma or serum are stabilised upon collection using appropriate stabilizers. E.g. blood or samples derived from blood such as plasma or serum are usually stabilised at least by adding an anticoagulant, preferably a chelating agent such as EDTA or sodium citrate. The used stabilization may add to preserve the extracellular nucleic acid population in the sample. Several methods are known in the prior art that achieve a stabilization of the sample including a stabilization of the extracellular nucleic acid population comprised in the sample. The stabilization prevents the degradation of the extracellular nucleic acids and/or prevents the contamination of the extracellular nucleic acids by intracellular nucleic acids, in particular genomic DNA that is released from cells that are contained in the sample. One common stabilization method employs the use of formaldehyde to stabilize the cell membranes, thereby reducing the cell lysis and furthermore, formaldehyde inhibits nucleases. Respective methods are e.g. described in U.S. Pat. No. 7,332,277 and U.S. Pat. No. 7,442,506. Alternative methods to stabilize blood samples are described e.g. in US 2010/0184069 and US 2010/0209930. A preferred method for stabilizing the sample is disclosed in European patent application EP11182819.0, filed Sep. 26, 2011 and U.S. patent application 61/539,245 filed Sep. 26, 2011, and in the corresponding PCT application which was filed today and which claims the priorities of the aforementioned EP and US applications.

According to one embodiment, the sample is a stabilized sample that was stabilized by contacting the sample with
 a) at least one apoptosis inhibitor,
 b) at least one hypertonic agent, which stabilizes the cells comprised in the sample, and/or
 c) at least one compound according to formula 1

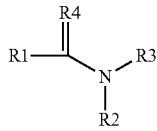

formula 1 wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue.

The term "apoptosis inhibitor" as used herein in particular refers to a compound whose presence in a cell-containing biological sample provides a reduction, prevention and/or inhibition of apoptotic processes in the cells and/or makes the cells more resistant to apoptotic stimuli. Preferably, the at least one apoptosis inhibitor that is used for stabilizing the sample is selected from the group consisting of metabolic inhibitors, caspase inhibitors and calpain inhibitors. Preferably, the apoptosis inhibitor is cell-permeable. Preferably, the apoptosis inhibitor is a caspase inhibitor having one or more of the following characteristics: a) it is a pancaspase inhibitor and thus is a broad spectrum caspase inhibitor; b) it comprises a modified caspase-specific peptide, wherein, preferably, said caspase-specific peptide is modified by an aldehyde, nitrile or ketone compound; c) it comprises a modified caspase-specific peptide that is modified preferably at the carboxyl terminus with an O-Phenoxy or a fluoromethyl ketone (FMK) group; and/or d) it is selected from the group consisting of Q-VD-OPh and Z-VAD(OMe)-FMK. Suitable concentration ranges for the apoptosis inhibitor(s) in the stabilized sample, include but are not limited to 0.01 µM to 100 µM, 0.05 µM to 100 µM, 0.1 µM to 50 µM, 0.5 µM to 50 µM, 1 µM to 40 µM, more preferably 1 µM to 30 µM or 2.5 µM to 25 µM. According to one embodiment, a caspase inhibitor is used in combination with an anticoagulant in order to stabilize a blood sample.

The at least one hypertonic agent that can be comprised in the stabilized sample is preferably used in combination with the apoptosis inhibitor, which preferably is a caspase inhibitor. The hypertonic agent induces cell shrinking by mild hypertonic effects (osmosis), thereby increasing the cell stability. The hypertonic agent present in the stabilized sample in particular stabilizes cells contained in the sample, thereby reducing the amount of intracellular nucleic acids, in particular genomic DNA that can be released from damaged cells. Thereby, the extracellular nucleic acid population is substantially preserved and the risk of contaminating respectively diluting the extracellular nucleic acids with intracellular nucleic acids, in particular genomic DNA, is reduced. Preferably, the hypertonic agent has one or more of the following characteristics:
 a) it is uncharged;
 b) is a hydroxylated organic compound and accordingly, carries at least one, preferably at least two hydroxyl groups;
 c) it is a polyol, preferably comprising 2 to 10 hydroxyl groups, preferably 3 to 8 hydroxyl groups;
 d) it is a hydroxy-carbonyl compound and hence a compound possessing one or more hydroxy (OH) groups and one or more carbonyl groups;
 e) it is selected from the group of hydroxylated ketone compounds, carbohydrates or compounds derived therefrom;
 f) it is selected from the group consisting of polyalcohols, sugar alcohols, carbohydrates, glucose, raffinose, sucrose, fructose, alpha-d-lactose monohydrate, dihydroxyacetone, alcohols, glycerol, erythritol, mannitol, sorbitol, volemitol;
 g) it is water-soluble and non-toxic to cells; and/or
 h) it does not induce or support the lysis of the cells contained in the biological sample and accordingly, preferably does not function as a detergent or as cell membrane dissolving agent.

The stabilized sample may comprise the at least one hypertonic agent or mixture of hypertonic agents in a concentration range selected from 0.05M to 2M, 0.1M to 1.5M, 0.15M to 0.8M, 0.2M to 0.7M or 0.1M to 0.6M. Respective concentrations are particularly suitable when using a hydroxylated organic compound, e.g. a carbohydrate such as dihydroxyacetone as hypertonic agent for stabilization.

As discussed above, the stabilized sample may comprise a compound according to formula 1 which is effective in achieving a remarkable stabilizing effect and in substantially preserving the composition of the extracellular nucleic acid population in the stabilized sample. Also a mixture of one or more compounds according to formula 1 can be used for stabilization. Said compound may also be used in combination with the apoptosis inhibitor and/or the hypertonic agent described above. The hydrocarbon residues R2 and/or R3 can be selected independently of one another from the group comprising alkyl, including short chain alkyl and long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. The chain length n of R2 and/or R3 can in particular have the values 1, 2, 3, 4, 5, 6, 7, 8, 9, 10, 11, 12, 13, 14, 15, 16, 17, 18, 19 and 20. Preferably R2 and R3 have a length of the carbon chain of 1-10. Preferably, R2 and R3 have a length of the carbon chain of 1-5. Particularly preferred is a chain length of 1 or 2 for R2 and R3. The chain length n of R1 preferably has the value 1, 2, 3, 4 or 5. Particularly preferred is a chain length of 1 or 2 for R1. R4 preferably is oxygen. According to a preferred embodiment, the compound according to formula 1 is a N,N-dialkyl-carboxylic acid amide. According to one embodiment, the compound is selected from the group consisting of N,N-dimethylacetamide; N,N-diethylacetamide; N,N-dimethylformamide and N,N-diethylformamide. Preferably, the substance according to formula 1 is N,N-dimethlylacetamide (DMAA). The stabilized sample may comprise said compound according to formula 1 or mixture of respective compounds in a concentration range of 0.1% up to 50%. Preferred concentration ranges can be selected from the group consisting of 0.1% to 30%, 1% to 20%, 1.25% to 15%, 1.5% to 10%, 1.5% to 7.5% and 1.5% to 5%. Respective concentrations are particularly suitable when using a N,N-dialkyl-carboxylic acid amide, e.g. N,N-dimethylacetamide, N,N-diethylacetamide, N,N-diethylformamide or N,N-diemethylformamide as stabilizing agent. Also N,N-dimethylpropanamide can be used.

An anticoagulant, preferably a chelating agent can also be used in addition to the above mentioned stabilizers.

The term "sample" preferably refers to a natural sample, e.g. as obtained from a human or animal, which may have been, however, optionally stabilized by appropriate agents. Stabilized samples are also encompassed be the term "sample" and also by the term "natural sample". Furthermore, cells may have been removed from the original sample. Respective cell-depleted or cell-free samples are also encompassed by the term "sample" and also by the term "natural sample". Typical examples of respective natural samples are body fluids such as blood and samples derived from a body fluid, in particular samples that derive from a body fluid by removing cells from the body fluid. Blood is obtained from the human or animal and usually is immediately stabilized e.g. in EDTA or other suitable stabilisation compositions (see above). Furthermore, cells may have been removed from the blood sample to obtain blood plasma and/or blood serum. Respective samples which may have been optionally stabilized and from which cells may have been optionally be removed are also encompassed by the term "sample" as well as by the term "natural sample". Suitable samples are also described above. The term "natural sample" preferably does not refer to and hence includes processed samples to which binding reagents, lysis reagents or chaotropic salts have been added which increase the volume of the natural sample by more than 10%, more than 5%, more than 2.5%, more than 2% or more than 1%. According to one embodiment, no respective reagents were added. As discussed above, the natural sample may comprise stabilizing agents. For the avoidance of doubt, respective stabilizing agents and/or stabilizing compositions that were added when obtaining the sample, e.g. the body fluid, are not encompassed in the determination of the volume contribution of reagents that were added to process the sample. This in particular applies if said stabilising agents do not induce and/or promote cell lysis. If stabilizing agents are used that induce and/or promote lysis, they are according to one embodiment encompassed in the determination of the volume contribution of reagents that were added to process the sample. However, usually respective agents are not used as stabilizers for stabilizing cell free nucleic acids, because if they induce lysis of the cells, they do not stabilize the extracellular nucleic acid population but promote their contamination with intracellular nucleic acids.

The solid phase that is used in the methods according to the present invention carries anion exchange groups. The anion exchange groups preferably comprise at least one protonatable group. Any solid phase suitable for anion exchange chromatography may be used, including but not limited to silicon containing materials such as silica and polysilicic acid materials, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, titanium oxide and zirconium oxide, metals such as gold or platinum, sephadex, sepharose, polyacrylamide, divinylbenzene polymers, styrene divinylbenzene polymers, dextrans, and derivatives thereof; glass or silica surfaces. Preferred formats of the solid phase include but are not limited to particles, beads, membranes, filters, plates, and capillary tubes. In some embodiments, the anion exchange groups can be linked to the surfaces of processing vessels such as micro-tubes, wells of micro-plates, or capillaries, and using these surfaces nucleic acids can be isolated also on a micro scale. The solid phase preferably is made of or contains mineral or polymeric material such as silica, glass, quartz, polyethylene, polypropylene, polyvinylidene fluoride, polyacrylonitrile, polyvinylchloride, polyacrylade, methacrylate or methyl methacrylate. Preferably, at least the surface carrying the anion exchange groups is composed of one of these materials or a mixture thereof, preferably silica materials and/or glass.

Furthermore, the solid phase may comprise magnetic material, the use of magnetic particles is particularly preferred. Examples include but are not limited to magnetic (e.g. paramagnetic, superparamagnetic, ferromagnetic or ferrimagnetic) particles, including but not limited to polystyrene, agarose, polyacrylamide, dextran, and/or silica and polysilicic acid materials having a magnetic material incorporated therein or associated therewith. The magnetic material may be ferrimagnetic, ferromagnetic, paramagnetic or superparamagnetic and preferably is superparamagnetic or ferromagnetic. Preferably the magnetic material is completely encapsulated e.g. by the silica, polysilicic acid, glass or polymeric material. In certain preferred embodiments, the nucleic acid binding matrix is a silicon containing particle, preferably a polysilicic acid particle, preferably a magnetic polysilicic acid particle which carries anion exchange groups. When using magnetic particles, preferably, the separation is achieved by the aid of a magnet. According to one embodiment, the nucleic acid binding matrix carrying the nucleic acid is magnetically attracted to the bottom or to a wall of the reaction vessel containing the reaction mixture and then the remaining reaction mixture is removed from the reaction vessel, for example by suction or decanting, or the magnetic particles are removed from the reaction vessel by plunging a magnet into the reaction vessel and removing the magnetic particles from the remaining sample.

For functionalizing a surface with anion exchange groups, several methods are feasible. The anion exchange groups may be bound directly to the surface, either covalently or non-covalently, electrostatically and/or may form part of a polymer or other composition which forms a surface coating or which is provided at the surface of the solid phase. The anion exchange groups may also be precipitated on the solid phase. According to one embodiment, the anion exchange groups are applied in form on a coating on the solid phase.

The anion exchange groups preferably are attached to the surface of a solid phase material as described above, in particular by covalent coupling. Hence, the solid phase may be functionalized for attachment of the anion exchange groups, for example with functionalities such as Si—O—Si, Si—OH, alcohol, diol or polyol, carboxylate, amine, phosphate or phosphonate. The anion exchange groups may be attached to the solid phase, for example, by using epoxides, (activated) carboxylic acids, silanes, acid anhydrides, acid chlorides, formyl groups, tresyl groups or pentafluorophenyl groups. The functional groups may be attached directly to the solid phase or via (linear or branched) spacer groups, e.g. hydrocarbons such as —$(CH_2)_n$— groups, carbohydrates, polyethylenglycols and polypropylenglycols. Alternatively, also a polymer composed of monomers comprising the anion exchange group such as an amino functional group can be used as anion exchange material. In certain embodiments, the solid phase material has a silicon containing surface such as a polysilicic acid surface and the anion exchange groups are coupled to said surface using a silane group.

Anion exchange materials that can be used in the context of the present invention include, but are not limited to, materials modified with anion exchange groups. Examples of such anion exchange groups are monoamines, diamines, polyamines, and nitrogen-containing aromatic or aliphatic heterocyclic groups. Preferably, the anion exchange group comprises at least one primary, secondary or tertiary amino group. In preferred embodiments, the anion exchange group comprises a group selected from the group consisting of primary, secondary and tertiary amines of the formula

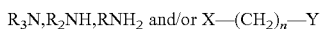

$R_3N, R_2NH, RNH_2$ and/or X—$(CH_2)_n$—Y wherein
X is $R_2N$, RNH or $NH_2$,
Y is $R_2N$, RNH or $NH_2$,
R is independently of each other a linear, branched or cyclic alkyl, alkenyl, alkynyl or aryl substituent which may comprise one or more heteroatoms, preferably selected from O, N, S and P, and
n is an integer in the range of from 0 to 20, preferably 0 to 18.

Hence, the anion exchange groups may have a protonatable group and optionally may have more than one protonatable group which may be the same or different from each other. A protonatable group preferably is a chemical group which is neutral or uncharged at a high pH value and is protonated at a low pH value, thereby having a positive charge. In particular, the protonatable group is positively charged at the first pH in the methods according to the present invention at which binding of the nucleic acid to the solid phase occurs. Preferably, the pKa value of the (protonated) protonatable group is in the range of from about 8 to about 13, more preferably from about 8.5 to about 12 or from about 9 to about 11.

Hence, examples of suitable anion exchange groups are in particular amino groups such as primary, secondary and tertiary amino groups as well as cyclic amines, aromatic amines and heterocyclic amines, preferably tertiary amino groups. The amino groups preferably bear alkyl, alkenyl, alkynyl and/or aromatic substituents, including cyclic substituents and substituents which together with the nitrogen atom form a heterocyclic or heteroaromatic ring. The substituents preferably comprise 1 to 20 carbon atoms, more preferably 1 to 12, 1 to 8, 1 to 6, 1 to 5, 1 to 4, 1 to 3 or 1 or 2 carbon atoms. They may be linear or branched and may comprise heteroatoms such as oxygen, nitrogen, sulfur, silicon and halogen (e.g. fluorine, chlorine, bromine) atoms. Preferably, the substituents comprise not more than 4, more preferably not more than 3, not more than 2 or not more than 1 heteroatom.

In one embodiment the anion exchange group preferably carries 1 to 10 amino groups. More preferably the anion exchange groups carries 2 to 8, and particularly the anion exchange group carries 2 to 6 amino groups.

Particular examples of amine functions are primary amines such as aminomethyl (AM), aminoethyl (AE), aminoalkyl, alkylaminoalkyl, dialkylaminoalkyl such as diethylaminoethyl (DEAE), ethylendiamine, diethylenetriamine, triethylentetraamine, tetraethylenepentaamine, pentaethylenhexaamine, trimethylamino (TMA), triethylaminoethyl (TEAE), linear or branched polyethylenimine (PEI), carboxylated or hydroxyalkylated polyethylenimine, jeffamine, spermine, spermidine, 3-(propylamino)propylamine, polyamidoamine (PAMAM) dendrimers, polyallylamine, polyvinylamine, N-morpholinoethyl, polylysine, and tetraazacycloalkanes. Preferred protonatable groups attached to the nucleic acid binding ligands are dialkylamino groups, especially diethylamino groups. As is shown by the examples, these groups are favourable with respect to their binding efficiency and their advantages when performing a size selective elution.

The anion exchange group is preferably attached to the solid phase via a linker group. Thus, the anion exchange group in particular comprises a protonatable group attached to a linker group. The linker group preferably is a linear, branched or cyclic alkylen, alkenylen or alkynylen group which preferably comprises 1 to 20 carbon atoms, more preferably 1 to 12, 1 to 8, 1 to 6, 1 to 5, 1 to 4, 1 to 3 or 1 or 2 carbon atoms. It may further comprise heteroatoms such as oxygen, nitrogen, sulfur, silicon and halogen (e.g. fluorine, chlorine, bromine) atoms, preferably not more than 4, more preferably not more than 3, not more than 2 or not more than 1 heteroatom. In preferred embodiments, the linker group is an alkylene group, in particular a propylene group.

In certain embodiments, the solid phase further comprises inert ligands. Preferably, the inert ligands are not significantly involved in nucleic acid binding and/or do not strongly bind to nucleic acids. In particular, the inert ligands are neutral or uncharged and preferably are hydrophilic. The inert ligands may be attached to the nucleic acid binding matrix as described herein for the nucleic acid binding ligands. Preferably, the inert ligands are organic moieties, in particular alkyl, alkenyl, alkynyl or aromatic moieties which may be linear, branched or cyclic and which preferably comprise at least one heteroatom such as oxygen, nitrogen, sulfur, silicon and halogen (e.g. fluorine, chlorine, bromine) atoms. The inert ligand preferably comprises 1 to 20 carbon atoms, more preferably 1 to 12, 1 to 8, 1 to 6, 1 to 5, 1 to 4, 1 to 3 or 1 or 2 carbon atoms, and up to 4, more preferably up to 3, up to 2, or up to 1 heteroatom. Particularly preferred are inert ligands comprising at least one hydroxyl group, in particular at least 2 hydroxyl groups, such as ligands comprising a 2,3-dihydroxypropyl group. A specific example of the inert ligands is a (2,3-dihydroxypropyl)oxypropyl group.

The inert ligands can be used to reduce the amount of nucleic acid binding anion exchange groups which will attach to the solid phase during coupling of the anion exchange groups. Hence, the density of the anion exchange groups on the surface of the solid phase can be controlled and adjusted to the subsequent application of the solid phase. In particular, the solid phase may comprise anion exchange groups and inert ligands in a ratio in the range of from about 1:1 to about 1:10, preferably from about 1:2 to about 1:5, more preferably about 1:3. Using a solid phase such as magnetic particles which additionally comprises inert ligands as described has the advantage that very mild elution conditions can be used which is advantageous for many downstream applications.

In another embodiment, the solid phase does not comprise such inert ligands. Preferably, the solid phase only comprises the anion exchange groups and does not comprise any other ligands. According to one embodiment, the solid phase comprises a silicon containing surface, preferably a polysilicic acid surface and is derivatized with a silane compound comprising the anion exchange groups and is not derivatized with another silane compound.

Examples of suitable nucleic acid binding solid phases, anion exchange groups, protonatable groups and inert ligands are described in WO 2010/072834 A1, DE10 2008 063 001A1, WO002010072821A1 and DE 10 2008 063 003 and the respective disclosure is incorporated herein by reference.

According to one embodiment, total nucleic acids are isolated from the sample and the extracellular nucleic acids are comprised as a portion therein. If the sample is a cell-free or cell-depleted sample, the total nucleic acids isolated therefrom will predominantly comprise or even consist of extracellular nucleic acids. It is also within the scope of the present invention to isolate at least predominantly a specific target nucleic acid. A target nucleic acid can be e.g. a certain type of nucleic acid, e.g. RNA or DNA, including mRNA, microRNA, other non-coding nucleic acids, epigenetically modified nucleic acids, and other nucleic acids that are contained in the extracellular nucleic acid population. It is also within the scope of the present invention to e.g. digest the non-target nucleic acid using nucleases after isolation. The term target nucleic acid can also refer to a specific kind of nucleic acid, e.g. an extracellular nucleic acid that is known to be a certain disease marker or a viral nucleic acid. As discussed above, the isolation of extracellular nucleic acids may also comprise the specific isolation of a respective target nucleic acid e.g. by using appropriate capture probes. The term "a target nucleic acid" also refers to a nucleic acid having a certain length, e.g. a nucleic acid having a length of 2000 nt or less, 1000 nt or less or 500 nt or less (as discussed above, the chain length indicated by "nt" refers to by in case of double-stranded DNA). Isolating respective smaller target nucleic acids can be advantageous because it is known that extracellular nucleic acids usually have a smaller size of less than 2000 nt, usually less than 1000 nt and often even less than 500 nt. Focusing the isolation, respectively purification, on respective small nucleic acids can increase the portion of extracellular nucleic acids obtained in the isolated nucleic acids. Suitable means such as a selective elution are disclosed above.

The isolated nucleic acids can be directly analysed and/or further processed using suitable assay and/or analytical methods. If a respective direct use is intended, it is preferred that one or more of the above described washing steps is performed in the method according to the present invention in particular if downstream assays are used that are sensitive to impurities.

The isolated extracellular nucleic acids and/or a specific target extracellular nucleic acid comprised or suspected of being comprised therein can be identified, quantified, modified, contacted with at least one enzyme, amplified, reverse transcribed, cloned, sequenced, contacted with a probe and/or be detected. Respective methods are well-known in the prior art and are commonly applied in the medical, diagnostic and/or prognostic field in order to analyse extracellular nucleic acids (see also the detailed description in the background of the present invention). Thus, after extracellular nucleic acids were isolated, optionally as part of total nucleic acid, total RNA and/or total DNA (see above), they can be analysed to identify the presence, absence or severity of a disease state including but not being limited to a multitude of neoplastic diseases, in particular premalignancies and malignancies such as different forms of cancers. E.g. the isolated extracellular nucleic acids can be analysed in order to detect diagnostic and/or prognostic markers (e.g., fetal- or tumor-derived extracellular nucleic acids) in many fields of application, including but not limited to non-invasive prenatal genetic testing respectively screening, disease screening, oncology, cancer screening, early stage cancer screening, cancer therapy monitoring, genetic testing (genotyping), infectious disease testing, pathogen testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease infection or a fetal characteristic. Thus, as discussed above, the isolation method described herein may further comprise a step c) of nucleic acid analysis and/or processing. The analysis/further processing of the nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

According to one embodiment, the isolated extracellular nucleic acids are analysed to identify, detect, screen for, monitor or exclude a disease, an infection and/or at least one fetal characteristic.

Furthermore, as discussed above, the isolation method according to the present invention can also be used as a pre-treatment protocol in order to concentrate the extracellular nucleic acids from a sample for a subsequent nucleic acid purification protocol. This embodiment has the advantage that the extracellular nucleic acids may be concentrated from a large sample volume to a small sample volume. Basically any standard nucleic acid purification protocol can be used subsequent to the method according to the present invention to further purify the extracellular nucleic acids that were concentrated using the method according to the present invention. Examples for respective purification methods include but are not limited to extraction, solid-phase extraction, polysilicic acid-based purification, magnetic particle-based purification, phenol-chloroform extraction, anion-exchange chromatography (using anion-exchange surfaces), electrophoresis, precipitation and combinations thereof. It is also within the scope of the present invention to specifically isolate specific target extracellular nucleic acids from the enriched extracellular nucleic acid population, e.g. by using appropriate probes that enable a sequence specific binding and are coupled to a solid support. Also any other nucleic acid isolating technique known by the skilled person can be used. According to one embodiment, the nucleic acids are isolated and hence further purified from the enriched extracellular nucleic acids using at least one chaotropic agent and/or at least one alcohol. Preferably, the nucleic acids are isolated by binding them to a solid phase, preferably a solid phase comprising silicon, preferably polysilicic acid. Suitable methods and kits are also commercially available such as the QIAamp® Circulating Nucleic Acid Kit (QIAGEN), the QIAamp MinElute Virus Spin or Vacuum Kit (QIAGEN), the Chemagic Circulating NA Kit (Chemagen), the NucleoSpin Plasma XS Kit (Macherey-Nagel), the Plasma/Serum Circulating DNA Purification Kit (Norgen Biotek), the Plasma/Serum Circulating RNA Purification Kit (Norgen Biotek), the High Pure Viral Nucleic Acid Large Volume Kit (Roche) and other commercially available kits suitable for purifying circulating nucleic acids. Here also automated protocols such as those running on the QIAsymphony system, the EZ1 instruments, the QIAcube (QIAGEN) or MagNApure system (Roche), m2000 sample prep systems (Abbott), EasyMag systems (bioMerieux) are available. Also any other commercially available automated liquid-handling sample prep system suitable for isolating nucleic acids from biological cell-free samples can be used. If a respective further purification step is performed subsequent to the isolation method according to the present invention it is not necessary to perform the above described washing steps.

The enrichment of the extracellular nucleic acids from a large volume (e.g. 5 ml or more) of starting material allows the subsequent purification of nucleic acids using conventional commercially available nucleic acid extraction methods. In particular, performing an upfront enrichment step by reversible binding the extracellular nucleic acids to a solid phase carrying anion exchange groups, allows for purifying these nucleic acids using currently available automated systems, which typically limit the original sample input volume to 1 ml or less due to the increase in volume that occurs by the addition of further reagents that are added to lyse the sample and/or to establish the binding conditions.

The isolation protocol according to the present invention, as is illustrated in the example section below, can be performed manually but was also tested on robotic systems such as the QIAsymphony SP, a commercially available nucleic acid extraction robot capable of fully automated execution of nucleic acid enrichment and purification protocols. Because only low volumes of a simple chemistry have to be added according to the present invention, almost 3 ml sample can be automatically processed and the nucleic acids can be extracted from approx. 3 ml sample (the volume that can be handled by said robotic systems is limited to 3 ml). When performing the method according to the present invention manually (or when adapting the automated system accordingly), even larger sample volumes of 5 ml, 10 ml, 15 ml or more can be processed. Due to the simplicity of the method according to the present invention, the risk of handling errors is low. Furthermore, the method is very rapid and thus, can easily be integrated as a pretreatment procedure into existing operations in order to concentrate the extracellular nucleic acids from large sample volumes prior to performing a standard nucleic acid isolation protocol. Thereby, a maximum yield and purity of the isolated extracellular nucleic acids is ensured.

The methods according to the present invention are particularly suitable for processing samples which comprise low amounts of extracellular nucleic acids. The inventors surprisingly could demonstrate that the methods according to the present invention provide good nucleic acid yields even if the nucleic acid concentration in the sample is very low. As discussed in the introduction, extracellular nucleic acids are usually comprised in the samples (such as e.g. a plasma or serum sample) in rather low amounts of 1 to 100 ng/ml sample. Therefore, according to one embodiment, the sample containing the nucleic acid comprises only low amounts of nucleic acid in a concentration selected from less than 1 µg/ml sample, less than 500 ng/ml sample, less than 300 ng/ml sample, less than 200 ng/ml sample, less than 150 ng/ml sample, less than 100 ng/ml sample, less than 50 ng/ml sample or less than 30 ng/ml sample.

The advantage that it is possible to process large sample volumes with the method according to the present invention and concentrate the isolated nucleic acids in a low elution volume compensates for the low concentration of the extracellular nucleic acids in the starting material. Furthermore, as it is shown in the examples, the performance of the method according to the present invention is not hampered by low a concentration of the extracellular nucleic acids in the sample. Thus, the recovery rates are substantially the same, irrespective of whether the nucleic acids are comprised in high or in low concentrations dilutions in the sample.

Also provided is a method for isolating extracellular nucleic acids from a sample which is or is derived from a body fluid, preferably selected from blood, plasma or serum, and wherein said sample is optionally stabilized, wherein for isolation extracellular nucleic acids are bound to a solid phase carrying anion exchange groups, wherein said method comprises the following steps:

a. binding the extracellular nucleic acids to the solid phase in a binding mixture at a first pH≤6 which allows binding the extracellular nucleic acids to the anion exchange groups of the solid phase;
b. separating the solid phase with the bound extracellular nucleic acids;
c. optionally washing the extracellular nucleic acids;
d. eluting the extracellular nucleic acids from the solid phase at a second pH which is higher than the first pH that was used for binding the extracellular nucleic acid to the solid phase;
e. isolating the extracellular nucleic acids from the eluate.

This method describes an embodiment of the concept of the present invention, wherein the steps a. to d. are used to concentrate the extracellular nucleic acids preferably from a large sample volume into a small sample volume that can then be further processed in step e. to isolate the extracellular nucleic acids therefrom e.g. using standard nucleic acid isolation method. The advantages were explained above. Details with respect to the individual steps a. to e. were also described above and also apply here. It is referred to the above disclosure.

Furthermore, the inventors found a method to improve the recovery of small nucleic acids when using a nucleic acid binding solid phase. When isolating nucleic acids, in particular smaller nucleic acids such as e.g. extracellular nucleic acids, smaller nucleic acids are not recovered efficiently, even though they were initially bound to the nucleic acid solid phase in the binding step. It is assumed that this loss in recovery results from the tight, potentially irreversible binding of the smaller nucleic acids to the nucleic acid binding solid phase. Therefore, these nucleic acids mainly remain bound to the nucleic acid binding solid phase at common elution conditions. Thereby, the yield of smaller nucleic acids is reduced what poses a problem if the small nucleic acids are only represented in the nucleic acid population in a low amount of e.g. less than 100 ng/ml sample as is the case with extracellular nucleic acids. Furthermore, within the population of extracellular nucleic acids, a potential target nucleic acid such as e.g. a certain diagnostic marker is usually comprised in an even lower amount.

Therefore, there was a need to improve the recovery rate of smaller nucleic acids when using a nucleic acid binding solid phase.

The inventors found that pretreating the nucleic acid binding solid phase with a polymer, preferably polyacrylic acid prior to binding the nucleic acids to the solid phase surprisingly improves the recovery rate of smaller nucleic acids.

Thus, the present invention in a further aspect provides a nucleic acid binding solid phase that has been pretreated with a polymer. Furthermore, the present invention in a further aspect provides a method for producing a respective nucleic acid binding solid phase, comprising contacting the nucleic acid binding solid phase with a polymer, thereby binding the polymer to the solid phase. Furthermore, the present invention pertains to a method for isolating nucleic acids, preferably extracellular nucleic acids, wherein a nucleic acid binding solid phase is used that has been pretreated with a polymer. As discussed above, pretreating the solid phase with a polymer, preferably a synthetic polymer such as polyacrylic acid, results in that the nucleic acid binding characteristics of the nucleic acid solid phase are improved because the recovery of small nucleic acids can be increased.

The polymer may be any polymer or polymeric compound as long as it is capable of binding to the nucleic acid binding solid phase and provides the effect described herein, namely to improve the recovery of small nucleic acids. Binding of the polymer to the nucleic acid binding solid phase preferably is non-covalent and preferably involves ionic interaction. The polymer preferably is a polyacid which comprises multiple acidic groups and/or a polyanion which comprises multiple negatively charged groups. According to one embodiment, the polymer possess at least one deprotonatable oxygen function and preferably, the negative charge of the deprotonated form can be delocalised between geminal oxygen atoms.

Examples of respective polymers include polymers containing carboxyl functions, e.g. polyacrylic acid or maleic acid copolymers, as well as to such containing phosphor or sulphur including organic acid functions, e.g. polyphosphate, poly-dT resp. polysulfonate. Respective polymers are particularly suitable when using a nucleic acid binding solid phase comprising anion exchange groups as is described above. In these embodiments, the polymer preferably attaches to the nucleic acid binding solid phase via ionic interactions. According to one embodiment, the polymer is a polypeptide (this term includes proteins) such as e.g. a milk protein or BSA. In preferred embodiments, the polymer is not a nucleic acid and/or a polypeptide and/or a polysaccharide. The polymer preferably is at least partially deprotonated when attached to the nucleic acid binding matrix.

Preferably, polyacrylic acid is used in order to pretreat the nucleic acid binding solid phase. Preferably, a short polyacrylic acid is used which have a molecular weight below 2500, preferably below 2000. According to one embodiment, the molecular weight of the polyacrylic acid lies in a range between 1500 and 1950. As is shown in the examples, the pretreating the nucleic acid binding solid phase with a respective polyacrylic acid results in that the recovery of smaller nucleic acids, e.g. having a length of less than 500 nt, 300 nt, 250 nt, 200 nt, 150 nt, 100 nt or 75 nt (as discussed above the chain length indicated by "nt" refers to "bp" in case of double-stranded DNA) is significantly increased.

Examples of nucleic acid binding solid phases include but are not limited to silicon containing materials such as silica and polysilicic acid materials, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, silicon dioxide, titanium oxide and zirconium oxide, metals such as gold or platinum, sephadex, sepharose, polyacrylamide, divinylbenzene polymers, styrene divinylbenzene polymers, dextrans, and derivatives thereof; glass or silica surfaces. Preferred formats of the solid phase include but are not limited to particles, beads, membranes, filters, plates, and capillary tubes. Preferably, the nucleic acid binding solid phase is a solid phase as is described above which comprises anion exchange groups. Preferably, the solid phase comprises silane groups on its surface and e.g. has been silanized. Preferably, magnetic particles preferably comprising a silica material such as polysilic acid are used as solid phase. According to one embodiment, the solid phase is a porous material.

For producing the pretreated nucleic acid binding solid phase, the solid phase may be immersed in the polymer. Thereby, at least a portion of the binding sites of the solid phase which tightly bind small nucleic acids reduce become blocked. Blocking may be reversible or irreversible. According to one embodiment, the nucleic acid binding solid phase is incubated for several hours with the polymer. During the incubation process, the polymer can be used in a concentration of at least 1 mg/ml, preferably at least 5 mg/ml, at least 7.5 mg/ml, more preferred at least 10 mg/ml. Suitable ranges include but are not limited to 2.5 mg/ml to 25 mg/ml, preferably 5 mg/ml to 20 mg/ml. These amounts are particularly suitable when using polyacrylic acid.

Also provided is a kit comprising a nucleic acid binding solid phase that has been pretreated with a polymer as described above. The kit may comprise further reagents such as e.g. a binding, washing and/or elution solution. The kit preferably is designed for use in any of the methods according to the present invention. Furthermore, the nucleic acid binding solid phase that has been pretreated with the polymer as described above can be used in the methods according to the present invention.

Also provided is a method for producing a nucleic acid binding solid phase having improved characteristics, comprising contacting a nucleic acid binding solid phase with a polymer as described above, preferably selected from polyacrylic acid, maleic acid co-polymers, polysulfonates, polyphosphates and poly (dT) and binding the polymer to the nucleic acid binding solid phase, wherein the nucleic acid binding solid phase that has been treated with the polymer provides a higher yield of nucleic acids having a length of less than 500 nt, e.g. less than 400 nt, less than 350 nt, less than 300 nt, less than 250 nt, less than 200 nt, less than 150 nt or less than 100 nt (as discussed above the chain length indicated by "nt" refers to "bp" in case of double-stranded DNA), compared to the untreated nucleic acid binding solid phase when being used in a nucleic acid isolation method according to the present invention. Of course, the pretreated nucleic acid binding solid phase may also be used in a different nucleic acid isolation procedure. Details with respect to the polymer, the nucleic acid binding solid phase and the pretreatment process were described above. It is referred to the above disclosure which also applies here.

In a further aspect, the present invention provides a method for increasing the recovery of small nucleic acids (e.g. having a length of less than 500 nt, 350 nt, 250 nt, 200 nt, 150 nt or 100 nt) in a method for isolating nucleic acids using a nucleic acid binding solid phase, comprising the step of contacting the nucleic acid binding solid phase with a polymer.

Preferably, said contacting occurs by immersing the nucleic acid binding solid phase in the polymer, which preferably is a polyacid, during the production process of the solid phase. Details are described above.

Preferably, the method further comprises a washing step after the step of contacting the nucleic acid binding matrix with a polymer and prior to contacting the nucleic acid binding matrix with a nucleic acid. The washing conditions preferably are chosen so that polymer compounds bound inside and/or to the surface opening of the small pores of the nucleic acid binding matrix predominantly remain bound while the remaining polymer compounds are predominantly removed from the nucleic acid binding matrix. "Predominantly" in this respect in particular refers to at least 50% of the polymer compounds of the designated population of polymer compounds, preferably to at least 70%, at least 80%, at least 90% or at least 95%.

Unless defined otherwise herein, all technical and scientific terms used herein have the same meaning as commonly understood by one of ordinary skill in the art to which this invention belongs. This invention is not limited by the exemplary methods and materials disclosed herein, and any methods and materials similar or equivalent to those described herein can be used in the practice or testing of embodiments of this invention. Numeric ranges are inclusive of the numbers defining the range. Numeric ranges include a tolerance range of +/−10%, +/−5%, preferably +/−3% and most preferred +/−1%. According to one embodiment, the indicated numeric ranges include no tolerance range.

The term "solution" as used herein, e.g. in form of an acidifying solution, washing solution or elution solution, in particular refers to a liquid composition, preferably an aqueous composition. It may be a homogenous mixture of only one phase but it is also within the scope of the present invention that a solution that is used according to the present invention comprises solid components such as e.g. precipitates.

EXAMPLES

As nucleic acid binding solid phase, the following three magnetic ion exchange particles were used in the examples. These magnetic particles ("beads") allow for direct and specific binding of nucleic acids present at low concentrations in a complex sample material:

1. magnetic Beads (Type I)
2. magnetic Beads (Type II)
3. magnetic Beads (Type III)

All three bead types have a magnetic core and an anion exchange surface.

The magnetic Beads (Type I) and magnetic Beads (Type II) beads have a magnetic core of magnetite ($Fe_3O_4$). These magnetic particles are covered with polysilicic acid and together they form the so-called bead. Both types of magnetic particles are stored in water but can also be stored in other solutions such as e.g. SN-C solution (0.5M MES and Triton X-100, pH 6.1). The magnetic Beads (Type I) beads have a mixed surface of positively charged amines and neutral alcohols (details of the respective bead technology are also described in WO 2010/072834). Hence, positive electrical charge is "diluted" on the bead surface by neutral groups. This low positive charge leads to a weaker binding of the target nucleic acids, thereby allowing the elution at low pH-value (e.g. 8.5). In contrast, the magnetic Beads (Type II) have a consistent and intense positive charge, containing only positively charged tertiary amines on their surface. So binding of negative charged nucleic acids happens quick and easy. For efficient elution, higher pH values are preferably used.

The magnetic Beads (Type III) carry polyethylene imine groups on the surface of the magnetic core. These beads are stored in a SN-C suspension. For magnetic Beads (Type I) and (Type II), tertiary amines are present on the surface. For an alkaline reaction of the amine, a free electron pair is attached on the nitrogen atom. The protonation of the nitrogen moiety can be induced by acid addition. The tertiary amine group causes the positive charge for binding of polyanions (nucleic acids). The polyethylene imine groups, which are coupled on the surface of the Magnetic Beads (Type III), function in a similar way. The free electron pair, attached to the nitrogen atom, is protonated after acid addition.

In the subsequent examples, the QIAamp Circulating Nucleic Acid Kit was used as a cleanup protocol after the upfront concentration/enrichment of the extracellular nucleic acids using the method according to the present invention. Thereby, a very high purity was achieved. However, as is demonstrated below, the method according to the present invention also allows to directly use the isolated extracellular nucleic acids e.g. in PCR detection assays.

The QIAamp Circulating Nucleic Acid Kit was also used, in the examples shown below, as a reference method to determine the total amount of circulating and viral nucleic acids in a given sample and, hence, to be able to monitor the concentration success obtained with different anion exchange bead-based enrichment protocol according to the present invention.

The QIAamp Circulating Nucleic Acid Kit was identified as a suitable reference method, because it allows for extracting circulating, cell-free and viral nucleic acids from up to 5 ml plasma, serum and other body fluids. This manual kit works based on a silica-chaotrope technology, which leads, compared to other methods, to a high recovery of all fragment sizes among the ccf NA.

For quantification of the isolated nucleic acid, different assays were used:

The DNA assays were prepared according to the QuantiTect Multiplex PCR Handbook with the following exceptions:

For the 18S duplex assay another primer concentration is used (16 µM instead of 8 µM).

For the 18S DNA assay the time for annealing/extension is changed from 1 to 2 minutes.

The GAPDH RNA assay was carried out according to the QuantiTect Multiplex RT-PCR handbook with these modifications:

The cycling conditions were changed: The denaturation takes place for 1 min. at 95° C. and the annealing/extension for 1:30 min. at 60° C.

The CMV and HIV assay are commercially available as artus PCR Kits from QIAGEN. The PhHV assay was developed inhouse.

Example 1: Yields of the Nucleic Acid Extraction Depending on the Used Beads

For nucleic acid isolation, the following protocol was performed.

4 ml of pooled plasma is centrifuged at 16,000 g at 4° C. for 10 min. to remove residual cells and the cell-depleted plasma is transferred into a 15 ml falcon tube 100 µl of 1 M sodium acetate/acetic acid buffer (pH 4) is added to adjust the pH to a value between 5 and 6 (~25 mM NaOAc/HOAc in 4 ml sample)

8 mg each of both magnetic Beads (Type I) types, 4 mg of the magnetic Beads (Type II) beads or 4 mg of Magnetic Beads (Type III) are then used for binding Binding is performed for 20 min. at room temperature on an overhead rotational shaker (20 rpm)

Then the beads are separated for 10 min. in a magnetic falcon tube rack and the supernatant is discarded 1 ml of 100 mM Tris-HCl (with 0.9% sodium chloride and at pH 8.5) is added The solution is transferred into a 1.5 ml Eppendorf tube and the nucleic acids are eluted from beads for 20 min. on a thermomixer The beads are separated for 10 min. on a magnetic tube rack The eluate is purified using the QIAamp Circulating Nucleic Acid Kit according to the handbook, but without adding Carrier RNA The nucleic acids are eluted in 100 µl AVE, which is used as template for quantitative real-time PCR (10% template volume in the qPCR reaction mixture)

FIG. 1 shows the percentage yield of DNA fragments, whereas the results using three different bead types are compared. The fragments of three different sizes (75, 200 and 1000 bp) were spiked into the plasma sample as internal control and detected after extraction. 200,000 copies of each of the three fragments were added to 4 ml sample. To determine the reference yield of added DNA, the plasma was processed with the QIAamp Circulating Nucleic Acid Kit and the measured DNA yield was used as reference to be able to determine the yield achieved with the anion exchange bead-based enrichment protocols (see FIG. 1).

The use of magnetic Beads (Type II) beads led to a ~100% recovery. To ensure maximum recovery of the nucleic acids, it was found advantageous to modify the magnetic Beads (Type I) to especially improve the recovery of the smaller DNA fragments (here the 75 bp fragments of the internal control were tested). Therefore, according to one embodiment, the magnetic Beads (Type I) beads were incubated with polyacrylic acid before the concentration process to avoid the diffusion of the small DNA fragments into the bead pores, where they could be bound, respectively trapped irreversibly. The short polyacrylic acid polyanions saturated the binding sites and, hence, improved their recovery (~100% recovery of all fragment sizes). The Magnetic Beads (Type III) beads also led to a DNA recovery between 70 and 90%. Due to the used anion exchange groups, it was advantageous to use an elution buffer (40 mM sodium hydroxide) at a pH-value of approx. 12.6. For the other bead types, more moderate elution conditions could be used, and the extracellular nucleic acids were eluted with 100 mM Tris-HCl, pH 8.5 containing 0.9% sodium chloride.

Example 2: Enrichment of ccfDNA

Then the magnetic Beads (Type II) were used for the enrichment of ccf DNA. Therefore, the same protocol as described in Example 1 was used with the following changes:

The nucleic acid were not only extracted from the eluate, but also from the plasma supernatant after the binding step. This allows to assess the binding and elution efficiency.

After purifying the eluate using the QIAamp Circulating Nucleic Acid Kit, the nucleic acids were now eluted in a smaller volume (60 µl AVE).

Figure 2:
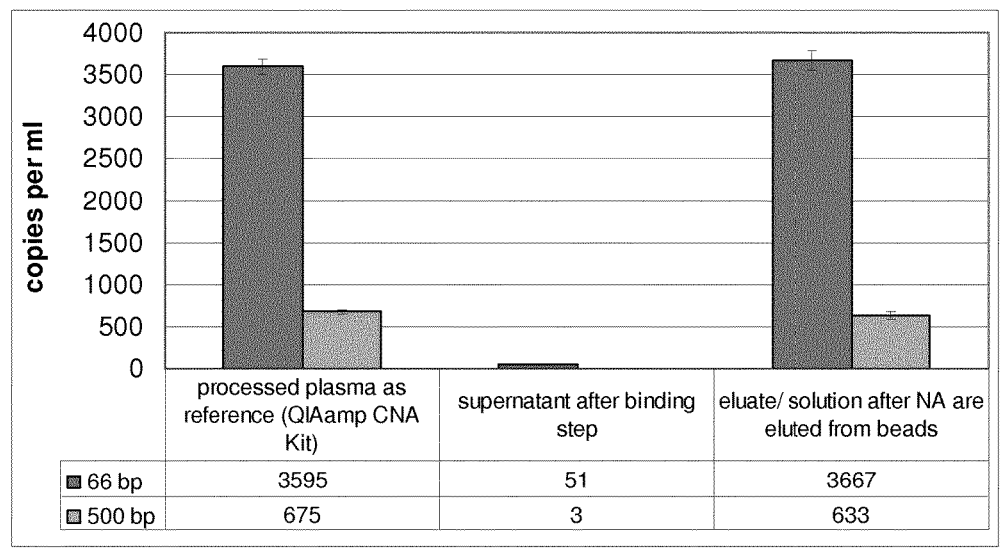
FIG. 2: Enrichment of ccfDNA (18S DNA duplex PCR assay): Control of the binding success by analyzing the supernatant after binding step and the eluate

With this experiment, the results of the internal control (75, 200 and 1000 bp fragments) were confirmed by the analysis of ccfDNA. Thereby, not only a ~100% DNA recovery was affirmed, it was also shown, that there was no loss of beads during the binding step. In FIG. 2, a DNA assay was used to detect circulating cell-free DNA. Two different DNA amplicons (66 and 500 bp) of the 18S rRNA coding sequence were quantified. The reference was used to determine the total amount of ccfDNA.

While only less than 2 or even 1% of unbound DNA could be found among the supernatant after the binding step, close to 100% recovery was achieved for both 18S rDNA targets. This indicates that the DNA fragments could be efficiently bound and recovered from 4 ml plasma using the magnetic Beads (Type II).

Example 3: Size-Selective Elution of DNA

Figure 3:
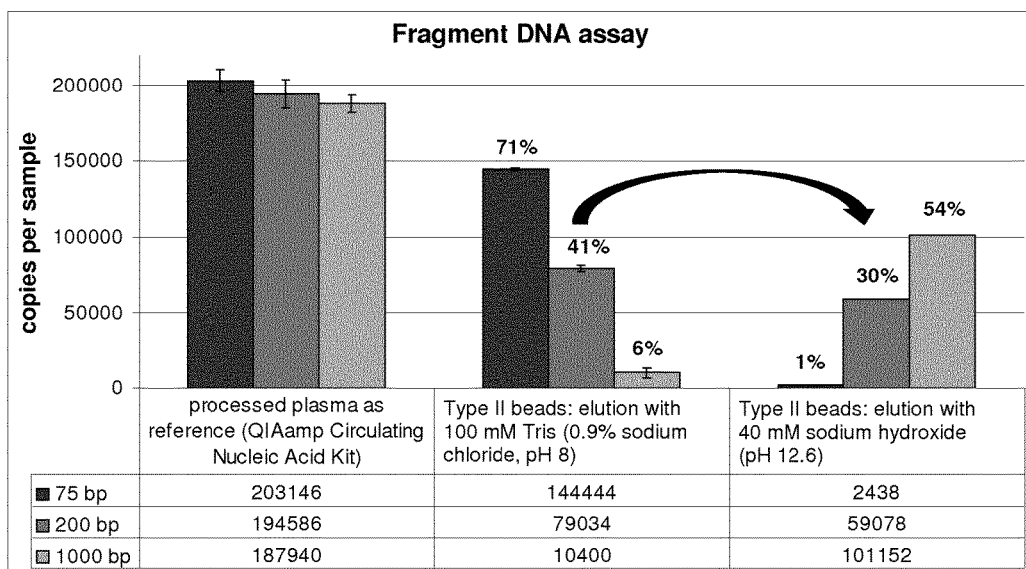
FIG. 3: Size-selective behavior of the magnetic Beads (Type II)-beads using two elution steps with two different elution buffers

An unexpected size selective behavior of the magnetic Beads (Type II) was discovered using almost the same protocol as for the enrichment of ccfDNA. The only difference was that the nucleic acids were eluted in two steps from the beads using two different elution buffers. FIG. 3 shows the results of the DNA fragment assay.

In a first step it was possible to achieve a preferred elution of shorter DNA fragments using the already mentioned elution buffer (100 mM Tris-HCl, containing 0.9% sodium chloride), but at pH 8. The remaining and especially longer DNA fragments were finally eluted at an alkaline pH (12.6) using 40 mM sodium hydroxide. However, as is shown in the other examples, also lower pH values of e.g. 8.5 can be used for an efficient elution. The use of lower pH values below 10 and preferably below 9 is favourable for downstream reactions.

400 µl Magnetic Beads (Type III) neutralisation-buffer (pH 8.5) was added to the 600 µl eluate containing the 40 mM sodium hydroxide before cleaning up the sample using the QIAamp Circulating Nucleic Acid Kit. For the neutralization of the eluate, a buffer containing 30 mM sodium hydroxide, 170 mM Tris, 0.31% HCl and 6 mM sodium azide was used.

Example 4: Enrichment of ccfRNA

The binding and elution conditions were especially optimized for ccfDNA. But, as FIG. 4 shows, also ccfRNA can be enriched from plasma using the method according to the present invention.

Figure 4:
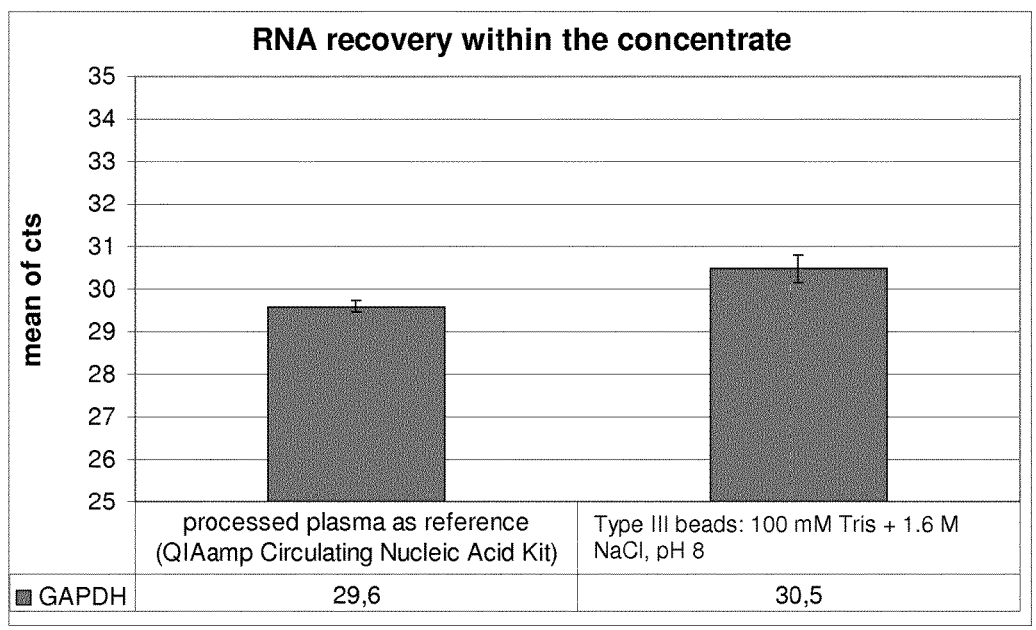
FIG. 4: Enrichment of ccfRNA, measured using a GAPDH assay

FIG. 4 shows the mean of Cts. The Ct value of 29.6, obtained with the reference extraction, stands for the total amount of circulating GAPDH mRNA within the 4 ml plasma sample, whereas the ct value of 30.5 indicates that GAPDH mRNA can be recovered at the end after a direct enrichment from plasma using the Magnetic Beads (Type III) beads.

Protocol which LED to the Best RNA Recovery in the Tested Embodiments:
4 ml of pooled plasma is centrifuged at 16,000 g at 4° C. for 10 min. and put into a falcon tube 1000 µl of 0.12 M sodium acetate/acetic acid buffer (pH 4) is added to adjust a pH value ≤5 (~25 mM in 4 ml sample)

400 µl Magnetic Beads (Type III) beads are then used for binding

Binding is performed for 20 min. @ room temperature on an overhead rotational shaker (20 rpm)

Then the beads are separated for 10 min. in a magnetic falcon tube rack and the supernatant is discarded 1 ml of 100 mM Tris-HCl (0.9% sodium chloride and at pH 8) is added The solution is transferred into a 1.5 ml eppendorf tube and the nucleic acids are eluted from beads for 20 min. on a thermomixer The beads are separated for 10 min. on a magnetic eppendorf tube rack The eluate is purified using the QIAamp Circulating Nucleic Acid Kit according to the handbook protocol for the purification of circulating DNA from 4 or 5 ml plasma or serum, but without using Carrier RNA The nucleic acids are eluted in 60 µl AVE, which is used as template for the quantitative real-time PCR (10% template volume)

Example 5: Direct Use of Eluate as PCR Template

FIG. 2 already showed that almost 100% DNA recovery could be achieved using the magnetic Beads (Type II). But for these experiments the protocol version with additional cleanup was used. Therefore, it was tested if the eluate could also be used directly as template in methods that are sensitive to impurities such as quantitative real-time PCR. The protocol is designed as follows:

"Direct" Isolation Protocol without Additional Cleanup to Demonstrate PCR Compatibility 4 ml of pooled plasma is centrifuged at 16,000 g at 4° C. for 10 min. and put into a falcon tube 100 µl of 1M sodium acetate/acetic acid buffer (pH 4) is added to adjust a pH between 5 and 6 (~25 mM in 4 ml sample)

4 mg of the magnetic Beads (Type II) are then used for binding

Binding is performed for 20 min. @ room temperature on an overhead rotational shaker (20 rpm)

Then the beads are separated for 10 min. in a magnetic falcon tube rack and the supernatant is discarded The beads are washed twice using $H_2O$+0.05% TritonX-100 (first with 1000, then with 300 µl); during the first wash step the bead solution is transferred into a 1.5 ml falcon tube After the addition of the wash buffer the beads are incubated for 5 min. using the thermomixer and separated for 10 min.

After the second wash step, 150 µl of 100 mM Tris-HCl (0.9% sodium chloride and at pH 8.5) is added The nucleic acids are eluted from beads for 20 min. on a thermomixer Then they are separated for 10 min. on a magnetic eppendorf tube rack The eluate/concentrate is used as template for the quantitative real-time PCR directly (10% template volume)

For the isolation protocol with additional cleanup, the eluate is processed using the QIAamp Circulating Nucleic Acid Kit according to the available protocol for the purification of circulating DNA from 4 or 5 ml plasma or serum, but without Carrier RNA. The nucleic acids are eluted in 100 µl AVE, which is used as template for the quantitative real-time PCR.

To test, if the eluate (here of pooled plasma samples) could be used as template for the qPCR directly, a PCR inhibition test was performed:

The ccf DNA recovery was compared with or without performing a cleanup protocol before qPCR. Three different template volumes per PCR were compared. If there was a PCR inhibition problem, the recovery after the performance of a cleanup protocol should be higher than using the eluate directly as template for the qPCR directly. Furthermore, the recovery would decrease using a higher template volume because of the increased concentration of PCR-inhibiting substances in the reaction mix.

Figure 5:
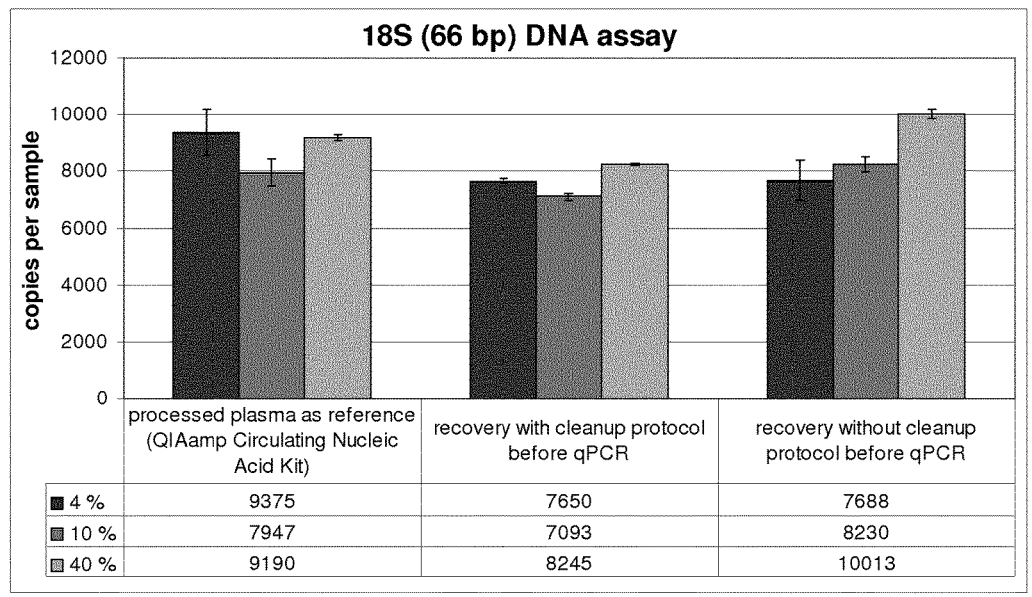
FIG. 5: Inhibition test to analyze, if the concentrate is PCR compatible or if a cleanup protocol has to be performed

FIG. 5 shows that the DNA recovery with or without the performance of a cleanup protocol is almost the same and the results are similar between the three different template volumes. So, surprisingly, the eluate that is obtained when using the simple, rapid method according to the present invention is PCR compatible without any further purification.

For the quantification of circulating cell-free DNA the already described 18S assay was used (66 bp amplicon). As reference method, the QIAamp Circulating Nucleic Acid Kit was used.

Examples 1-5 demonstrate that extracellular nucleic acids such as circulating cell-free DNA and RNA can be successfully enriched using magnetic anion exchange beads after acidifying the sample by adding sodium acetate/acetic acid. Elution of DNA/RNA is achieved by applying a neutral to alkaline elution buffer.

Example 6: Virus Enrichment from Plasma

Protocol 4 ml of pooled plasma is centrifuged at 16,000 g at 4° C. for 10 min. and put into a falcon tube The viruses CMV, HIV and PhHV (in form of particles) are spiked in 100 µl of 1M sodium acetate/acetic acid buffer (pH 4) is added to adjust a pH between 5 and 6 (~25 mM in 4 ml sample)

8 mg of both magnetic Beads (Type I) types (with and without polyacrylic acid) or 4 mg of the magnetic Beads (Type II) beads are then used for binding Binding is performed for 20 min. at room temperature on an overhead rotational shaker (20 rpm)

Figure 6:
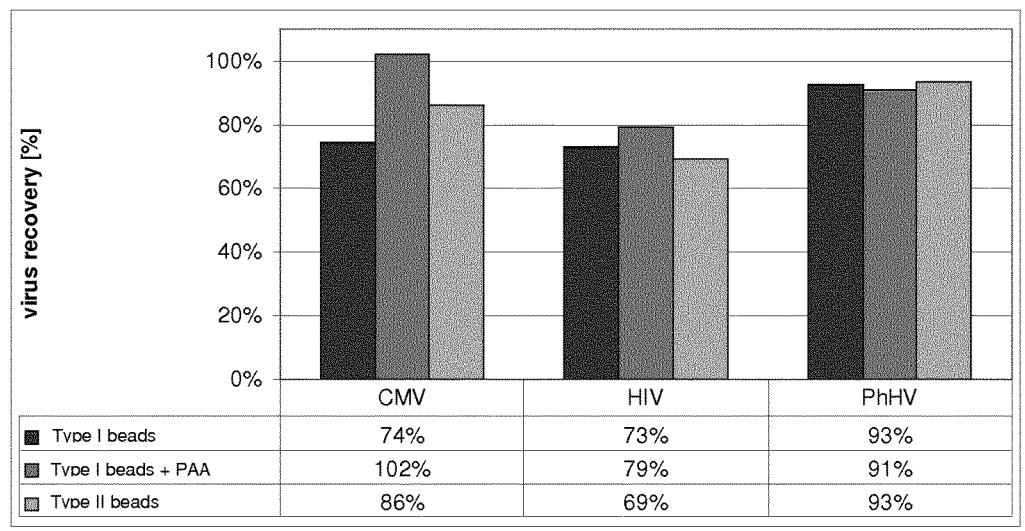
FIG. 6: Virus enrichment using three different types of magnetic anion exchange beads

The beads are separated for 10 min. in a magnetic falcon tube rack and the supernatant is discarded 1 ml of 100 mM Tris-HCl (0.9% sodium chloride, pH 8.5) is added The solution is transferred into a 1.5 ml eppendorf tube and the nucleic acids are eluted from beads for 20 min. on a thermomixer The beads are separated for 10 min. on a magnetic eppendorf tube rack The eluate is cleaned up using the QIAamp Circulating Nucleic Acid Kit according to the available protocol for the purification of circulating DNA from 4 or 5 ml plasma or serum, but without Carrier RNA The nucleic acids are eluted in 100 µl AVE, which is used as template for the quantitative real-time PCR Various viruses were tested and three different bead types were compared (magnetic Beads (Type I), magnetic Beads (Type I) after the incubation with polyacrylic acid, as well as magnetic Beads (Type II) beads). For CMV, HIV and PhHV, recoveries were achieved which correspond to 70-100% of the respective recoveries achieved with the reference protocol (see FIG. 6).

Example 7: Automated Nucleic Acid Enrichment

The anion exchange bead-based protocol for the isolation of circulating cell-free nucleic acids and viruses was automated on the QIAsymphony SP instrument (QIAGEN) and compared to the manual execution of the same protocol. In contrast to previous experiments, plasma samples from individual donors were used.

Protocol 2.9 ml plasma samples from twelve individual donors were (a) processed with the QIAamp Circulating Nucleic Acid Kit as reference, (b) manually isolated using magnetic Beads (Type II) (direct protocol version) or (c) isolated on the QIAsymphony SP. The QIAamp Circulating Nucleic Acid Kit was performed according to the handbook protocol for the purification of circulating DNA from 1 ml, 2 ml or 3 ml plasma or serum, but without Carrier RNA (elution in 150 µl AVE).

Manual version of the "direct" protocol according to the present invention
- 2.9 ml of plasma is centrifuged at 16,000 g at 4° C. for 10 min. and put into a tube
- The viruses CMV, HIV and PhHV (in form of particles) are spiked in
- 75 µl of 1M sodium acetate/acetic acid buffer (pH 4) is added to adjust a pH between 5 and 6
- 4 mg of the magnetic Beads (Type II) beads are then used for binding
- Binding is performed for 20 min. at room temperature on an overhead rotational shaker (20 rpm)
- Then the beads are separated for 10 min. in a magnetic falcon tube rack and the supernatant is discarded
- The beads are washed twice using $H_2O$+0.01% TritonX-100 (first with 1000 µl, then with 300 µl) and already during the first wash step the bead solution is transferred into a 1.5 ml falcon tube
- After the addition of the wash buffer the beads are incubated for 5 min. using the thermomixer and separated for 10 min.
- After the second wash step 150 µl of 100 mM Tris-HCl (0.9% sodium chloride, pH 8.5) are added
- The nucleic acids are eluted from beads for 20 min. on a thermomixer
- Then the beads are separated for 10 min. on a magnetic eppendorf tube rack
- The eluate is used as template for the quantitative real-time PCR directly (10% template volume)

Automated Version of the Direct Protocol According to the Present Invention
- 2.9 ml of plasma is centrifuged at 16,000 g at 4° C. for 10 min. and put into, e.g., a 14 ml polystyrene round bottom test tube (17*100 mm, BD)
- The viruses CMV, HIV and PhHV (in form of particles) are spiked in
- The tubes are inserted into the tube carrier and then loaded onto the QIAsymphony SP instrument for the automated processing
- The same incubation times and reagents are used as for the manual concentration version
- The elution volume is also the same (150 µl)

Figure 7:
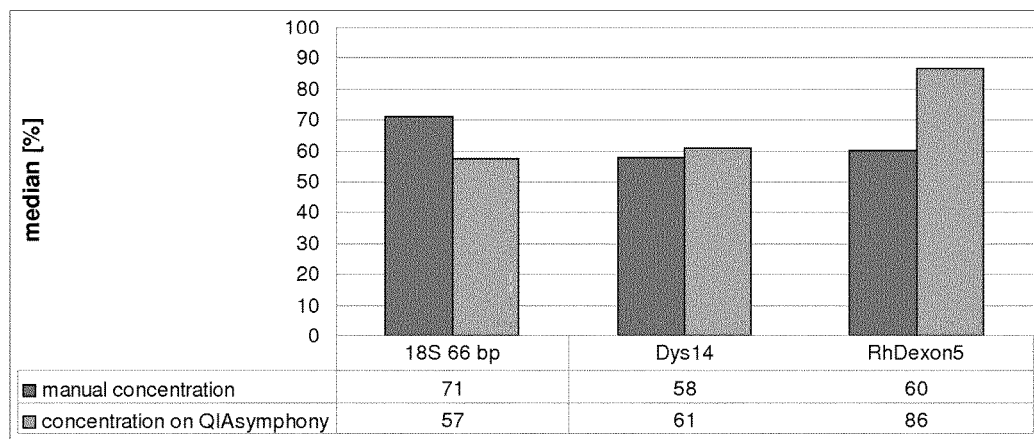
FIG. 7: The median from the percental yield compared to the reference of all individual donors (here results for three different DNA assays are shown)

The total amount of circulating cell-free nucleic acids varied among the individual plasma samples. In most cases the manual and automated protocol versions were comparable. The recovery of circulating DNA was measured by qPCR assays targeting 18S rDNA (66 bp amplicon), DYS14, and RhD (Exon #5). The median recoveries shown in FIG. 7 show that there is actually no significant difference between the manual and automated protocol version and that the ccfDNA recovery achieved with the anion exchange bead-based protocol corresponds to 60-80% of the total amount of circulating cell-free DNA (as determined after extraction using the QIAamp Circulating Nucleid Acid Kit reference method). The recovery rate can be further improved by optimizing the binding and elution conditions.

Figure 8:
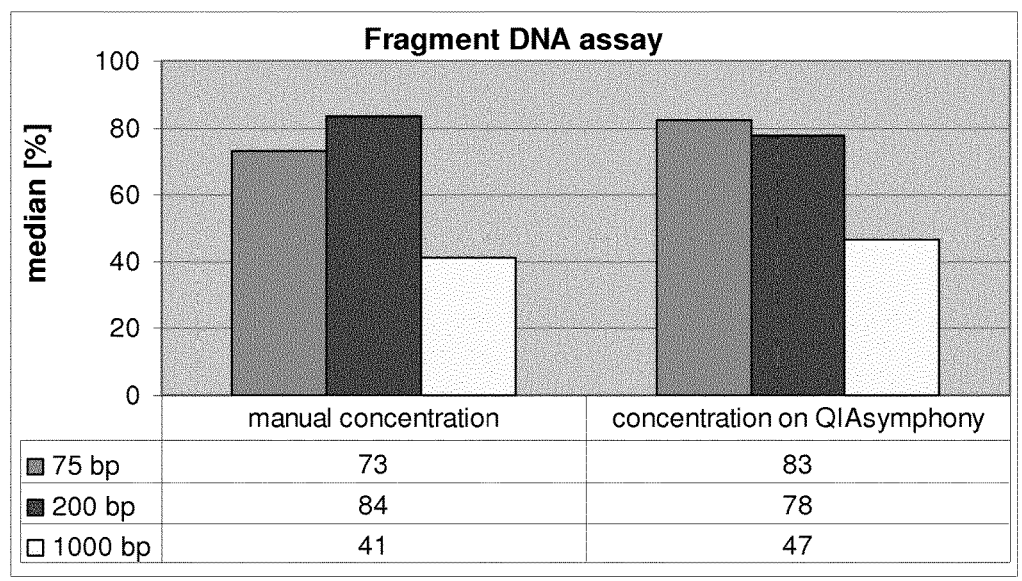
FIG. 8: The median recovery after using the fragment DNA assay (internal control)

FIG. 8 shows the median recovery of the three different fragment sizes of the internal control (75, 200 and 1000 bp). But while 70 to 80% of the 75 and 200 bp DNA fragments were detected within the concentrate, the recovery of the long 1000 bp DNA fragments was <50%. This surprising results points to a size-selective property of the anion exchange bead based protocol: Here, shorter DNA fragments (75-200 bp) are preferentially recovered compared to longer (1000 bp) DNA. This behavior is useful for, e.g., enrichment of extracellular nucleic acids such as fetal circulating DNA in maternal plasma and also circulating DNA fragments derived from tumors. The preferential binding of the smaller nucleic acids over longer nucleic acids reduces the amount of longer nucleic acids in the isolated nucleic acid population. This is with respect to the isolation of extracellular nucleic acids an advantage because in samples comprising extracellular nucleic acids such as e.g. urine, blood or blood products such as plasma or serum, comprised longer nucleic acids usually represent intracellular nucleic acids, that were released from cells (e.g. from damaged cells). Such intracellular nucleic acids represent a contamination of the extracellular nucleic acid population. The described nucleic acid isolation method advantageously depletes respective contaminating longer nucleic acids in the isolated extracellular nucleic acids.

Example 8: Binding of Lowly Concentrated Nucleic Acids

The analyze the binding capacity of the magnetic Beads (Type I) and their binding performance with samples containing only low nucleic acid concentrations, the following assay was performed:
- Pipet 50 mg beads into a 2 mL reaction vessel, magnetic separation (3 min.), discard supernatant from bead suspension
- Add the indicated volume of binding buffer (50 mM MOPS, pH 7.0) containing the 40 µg of plasmid-DNA (pCMV-b, 7164 bp)
- Incubate 10 min. on end-over-end rotational shaker
- Magnetic separation (3 min.), discard supernatant, wash twice with 500 µL binding buffer (5 min. end-over-end)
- Elute twice with 500 µL (each) 50 mM Tris, 20 mM KCl, pH 8.5

Figure 9:
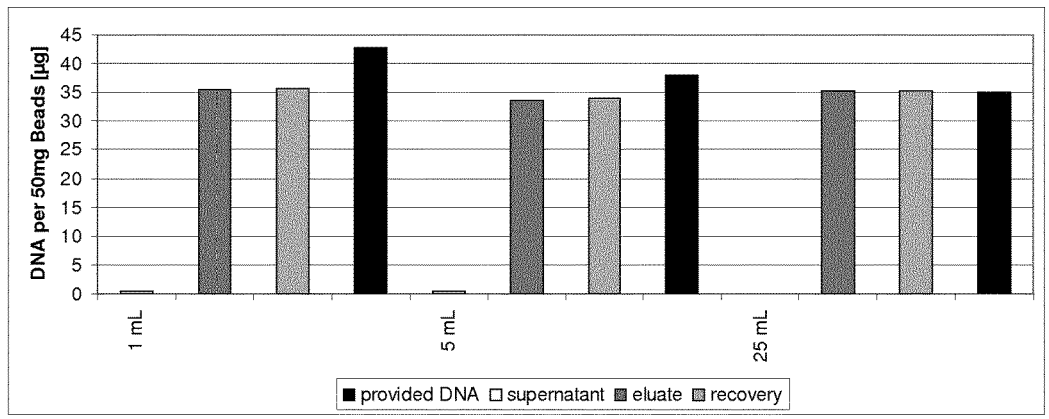
FIG. 9: The isolation efficacy using different nucleic acid concentrations.

In the assays, the entire added DNA was bound to the magnetic Beads (Type I) and eluted therefrom, regardless of the sample volume used (see FIG. 9). Thus, dilution of the sample does not decrease the performance and yield of the method. The results of these assays demonstrate that the magnetic Beads (Type I) are capable of effectively binding all nucleic acids even in samples containing the nucleic acid only in low concentration.

So, the following conclusions can be drawn from the above described experiments:
1. The optimal binding conditions of extracellular nucleic acids from blood samples (plasma and serum) or other body fluids can be adjusted using ¹⁄₄₀ sample volume of acidic sodium acetate/acetic acid buffer to set the pH value of the sample between 5 and 6, in particular when intending to isolate extracellular DNA.

2. The complete and direct binding of extracellular nucleic acids from the biological fluid is achieved after the addition of, e.g., magnetic particles with an anion exchange surface chemistry (e.g., tertiary amines or polyethylene imines of magnetic Beads (Type I), or Magnetic Beads (Type III)). Preferably, magnetic Beads (Type I) are incubated with polyacrylic acid prior to use to improve the DNA recovery of, especially, shorter fragments.

3. The remaining supernatant after the binding step can be removed and the bound extracellular nucleic acids can be eluted from the magnetic particles by adding an alkaline buffer (e.g. 100 mM Tris or MOPS) at an pH of 8 or higher (optional: addition of salt such as sodium chloride for recovery improvement).

4. After the removal of the magnetic particles the eluate can be further purified or directly used as template for analysis/detection methods such as quantitative real-time PCR (in the latter case, two additional wash steps are recommended before the nucleic acids are eluted).

5. Nucleic acids can be quantitatively isolated from samples comprising only low nucleic acid concentrations and dilution of the sample does not decrease the performance of the method according to the present invention.

Figure 10:
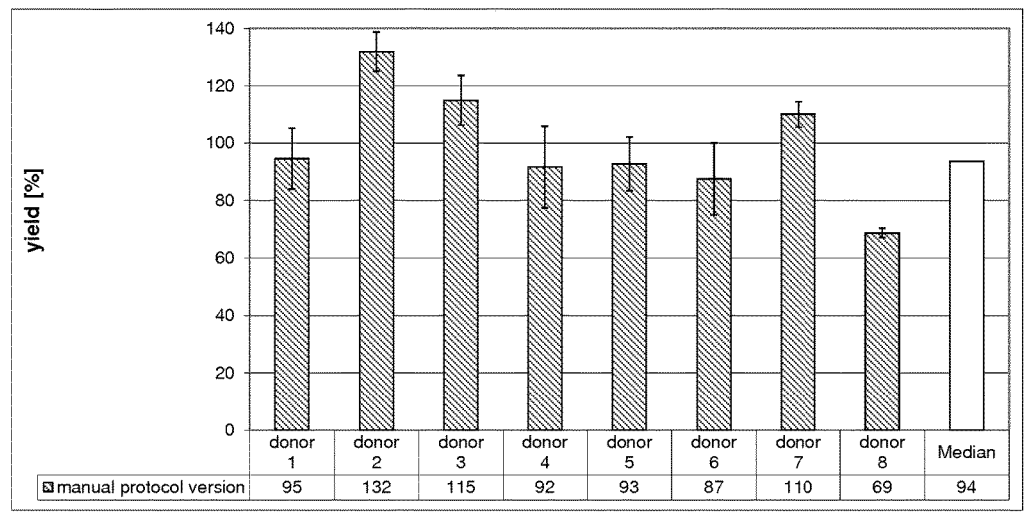
FIG. 10: Recovery of ccfDNA (18S)-manual enrichment protocol

Example 9: Recovery of ccfDNA (18S) Using a Manual Enrichment Protocol According to the Invention EDTA plasma from healthy donors was used for ccfDNA enrichment using a manual protocol according to the teachings of the present invention. Circulating cell-free DNA was purified from 3 ml plasma from 8 individual donors using the manual version of the enrichment protocol according to the present invention. DNA yield was quantified by real-time PCR targeting a 66 bp amplicon within the 18S ribosomal RNA coding sequence using the QIAGEN QuantiTect® Multiplex PCR Kit. The QIAamp® Circulating Nucleic Acid Kit (QIAGEN) served as reference (=100%). The results are shown in FIG. 10. On the right, the median percental recovery of all donors is shown. To indicate the upper and lower deviation the 10th and 90th percentiles are indicated by error bars.

Example 10: Spiked DNA Recovery-Manual Enrichment Protocol

In order to track a possible size-selectivity of the procedure and as internal control, DNA fragments (75 bp, 200 bp, 1000 bp) were added to EDTA stabilized plasma samples at 200,000 copies/sample. Circulating cell-free DNA was purified from 3 ml plasma of 8 individual donors using a manual version of the protocol according to the present invention.

Figure 11:
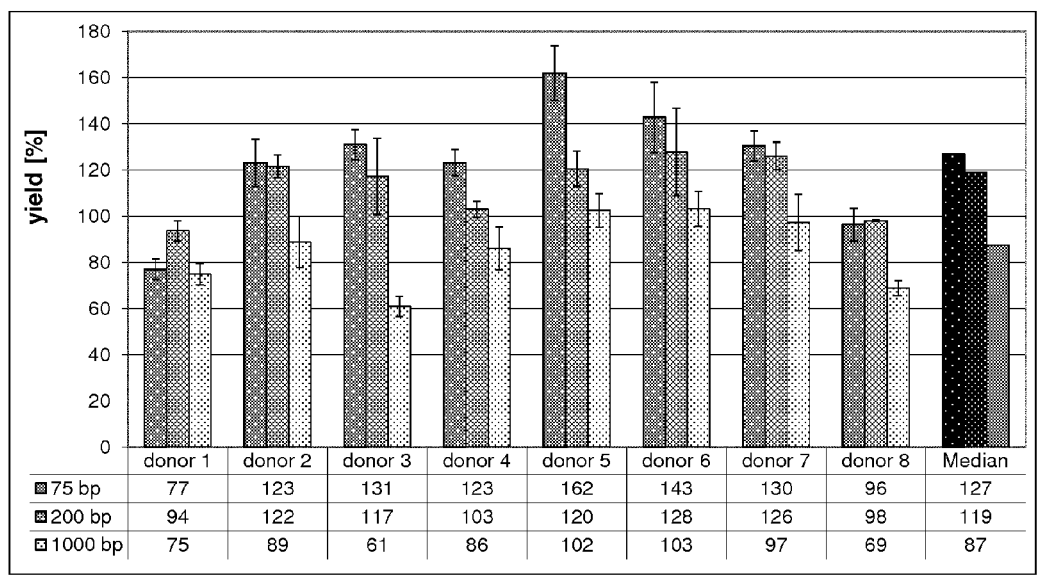
FIG. 11: Spiked DNA recovery—manual enrichment protocol

DNA yield was quantified by triplex, real-time PCR targeting regions within the 75 bp, 200 bp and 1000 bp fragment using the QIAGEN QuantiTect® Multiplex PCR Kit. The QIAamp® Circulating Nucleic Acid Kit (QIAGEN) served as reference (=100%). The results are shown in FIG. 11.

Example 11: Prenatal Diagnostics

Circulating cell-free nucleic acid was isolated from maternal blood samples using the method of the invention and ccf DNA was detected using a triplex qPCR assay. 5.8 ml plasma was processed from twelve individual donors. The samples were processed on the QIAsymphony SP instrument which however, can only process a maximum volume of 3 ml. Thus, the samples were split into two portions (2.9 ml plasma each) and loaded on the QIAsymphony SP instrument for automated processing following the automated enrichment protocol for the QIAsymphony SP (see example 7). Therefore, the two portions of the original sample were processed in parallel by acidifying the sample portions and adding an aliquot beads to each sample portion. Type 11 beads were used in this and all subsequent examples if not stated otherwise. After binding, the beads with the bound nucleic acids were removed from the binding mixture created from the first sample portion and were transferred into the binding mixture resulting from the second sample portion which also comprised an aliquot beads. Thereby, the nucleic acids from the first and second sample portion were combined. Thus, for the remaining binding incubation of the binding mixture of the second sample portion, the double amount of beads is present. This sample splitting and reunification allows to process a sample volume which is twice as large as the processing volume of the automatic system. When processing even larger samples, more portions can be created. All beads with bound nucleic acids were collected and washed twice with 100 mM Tris+154 mM NaCl (pH 7.2)+0.1% TritonX-100, and nucleic acids were eluted in 150 µl 100 mM Tris+154 mM NaCl (pH 9). Nucleic acids isolated with the QIAamp Circulating Nucleic Acid kit served as reference to determine the recovery rate. Furthermore, nucleic acids were isolated from the supernatant obtained after the beads with the bound nucleic acids were removed, using the QIAamp Circulating Nucleic acid Kit. Thereby, unbound ccf DNA remaining in the supernatant can be detected and quantified. 10% template volume of eluate was used in the triplex qPCR assay for detection of 18S rDNA (see FIG. 12a, DYS14 (see FIG. 12b), and RhD (see FIG. 12c). Shown is the % recovery compared to the QIAamp circulating nucleic acid kit.

Figure 12A:
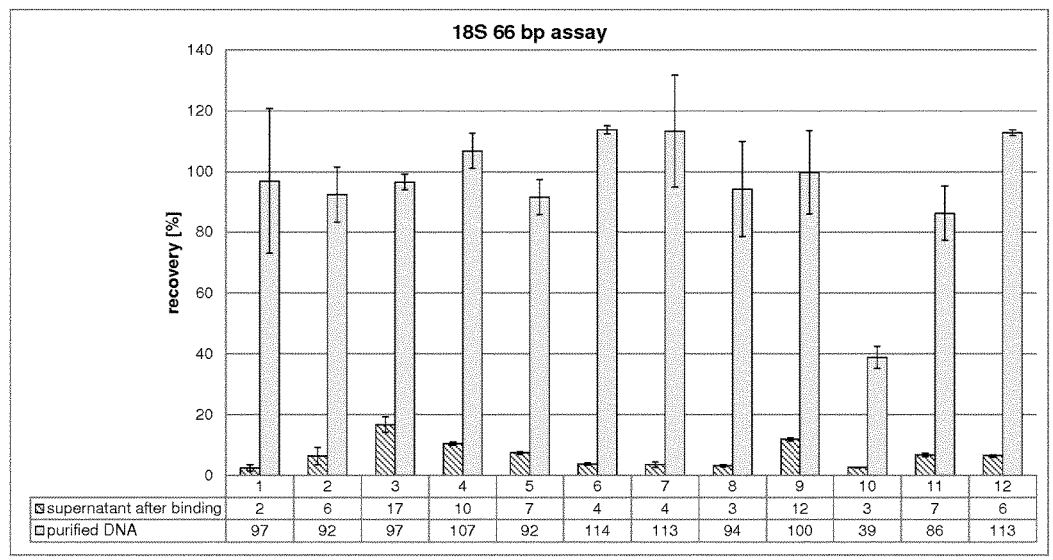
FIG. 12: Enrichment of fetal DNA, measured using an 18S detection assay, Dys14 assay and RhD assay.
Figure 12B:
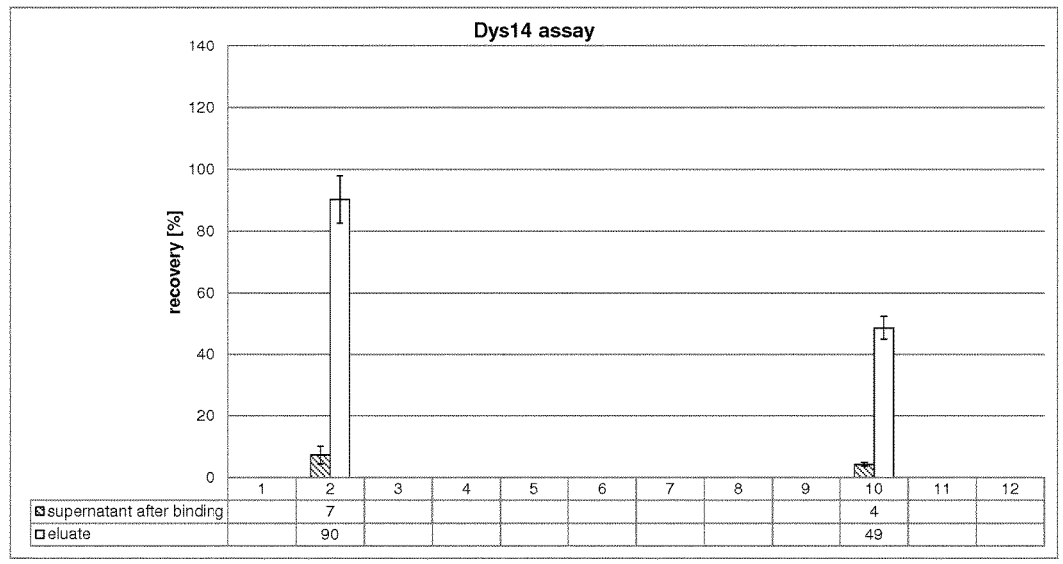

FIG. 12a shows that ccf DNA is almost completely bound to magnetic particles and eluted at the end (exception: donor 10). Only residual amounts of ccf DNA can be detected in the supernatant fraction. FIG. 12b shows the result of the Dys14 assay. Dys14 is a testis specific protein. Thus, detection of DYS14 ccf DNA in plasma derived from the fetus can be used for sex determination and is predictive of a male fetus. Of 12 samples tested, only 2 male donors are detected. ccf DNA recovery was comparable to the 18S rDNA results.

Figure 12C:
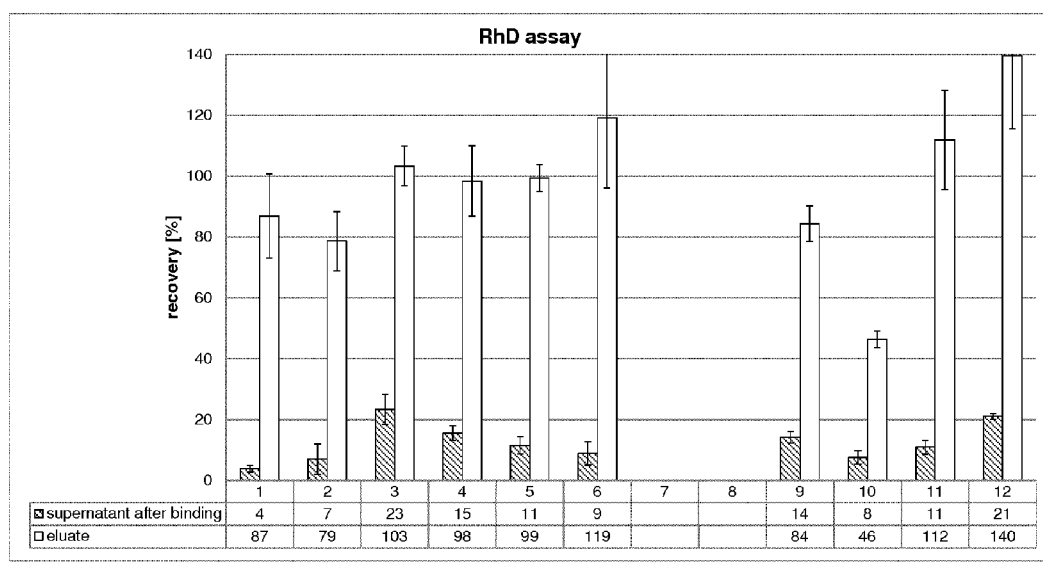

FIG. 12c shows the result of the RhD assay as part of the triplex DNA qPCR assay. Here, the Rhesus factor blood group is determined by testing for the D antigen. Donors 7 and 8 are RhD negative. ccf DNA recovery of all RhD positive donors was comparable to the 18S rDNA and DYS14 assay results.

The experiment shows that the method of the invention can be used for the specific detection of ccf DNA in maternal blood plasma. The method of the invention may readily applied in prenatal diagnostics, e.g. for prenatal sex determination and rhesus factor determination.

Example 12: Efficient Recovery and Enrichment of Short Extracellular DNA Fragments from Blood Plasma Ccf DNA was detected using different amplicon sizes for amyloid beta precursor protein (APP). ccfDNA was isolated as described in Example 11. real-time PCR detection of ccf DNA fragments with the sizes 67, 180 and 476 bp was done as described in Pinzani et al. 2011, Clin. Chim. Acta. 412: 2141. The copy number ratios 67/476 and 180/476 were calculated. The same ratios were calculated for ccf DNA isolated with the QIAamp circulating nucleic acid Kit (QIAamp CNA Kit). An enrichment of shorter DNA fragments leads to an increased copy number ratio.

Figure 13A:
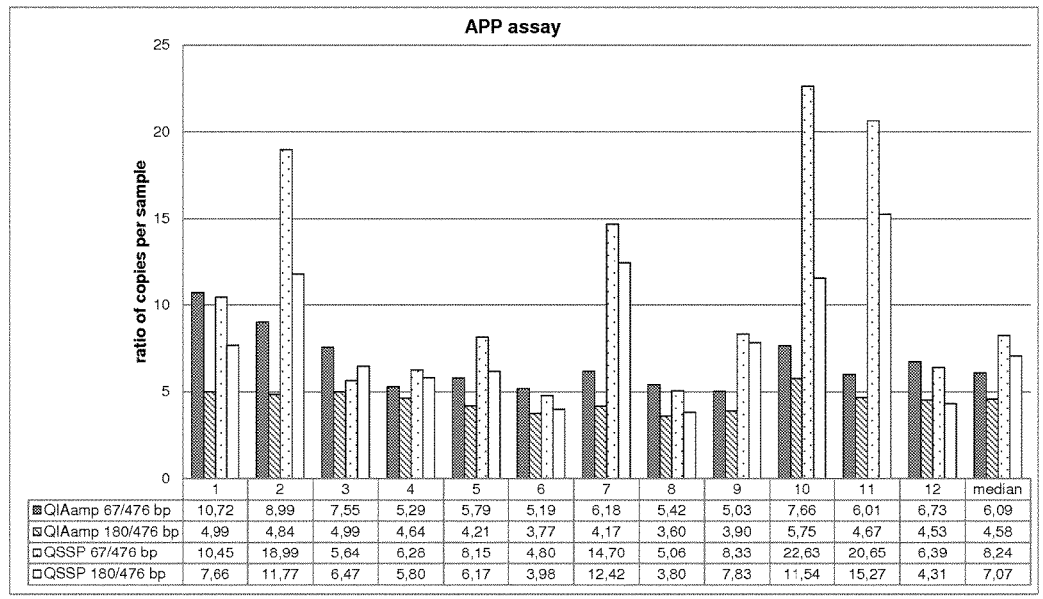
FIG. 13: Size-selective enrichment of short extracellular DNA fragments, measured by the APP assay.
Figure 13B:
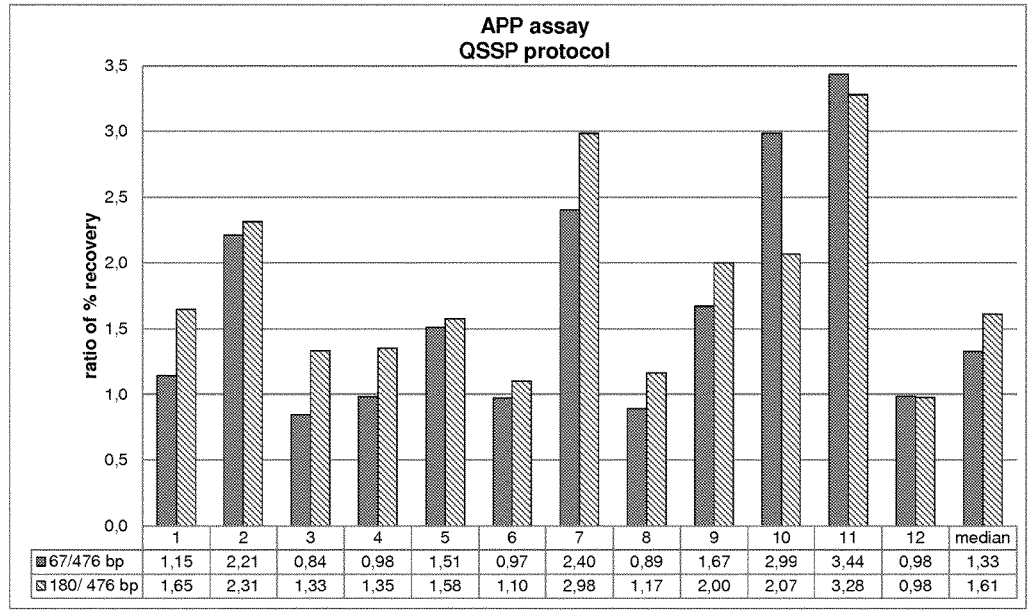

As can be seen in FIG. 13a, the automated enrichment protocol of the invention processed with the QIAsymphony SP (QSSP) shows similar or higher ratio values compared to the QIAamp CNA Kit reference protocol (QIAamp). Thus, the method of the invention can be used to efficiently isolate ccf DNA fragments of various sizes, in particular of short ccf DNA fragments which can even be enriched. FIG. 13b depicts the ratios of % DNA recovery obtained with the method of invention (QIAsymphony SP protocol) as compared to APP ccf DNA fragments isolated with the QIAamp CNA kit. An enrichment of shorter DNA fragments leads to ratios >1.0. The results show that shorter DNA fragments are completely extracted from plasma using the QIAsymphony SP protocol. For some donors, even an enrichment of shorter DNA fragments could be achieved using the method of the invention as compared to the reference protocol.

Example 13: PCR Compatibility of Elution Conditions

To determine whether a high pH value during elution might interfere with subsequent PCR-based detection, varying amounts of male human genomic DNA (31-8.000 copies) was spiked into different elution buffers (10-50 mM Tris buffer at pH 9 and ~pH 10.2). ccf DNA was detected using the 18S duplex assay. RNAse free water served as reference. Ct-values for 40% template volume in real-time PCR reaction were compared.

Figure 14A:
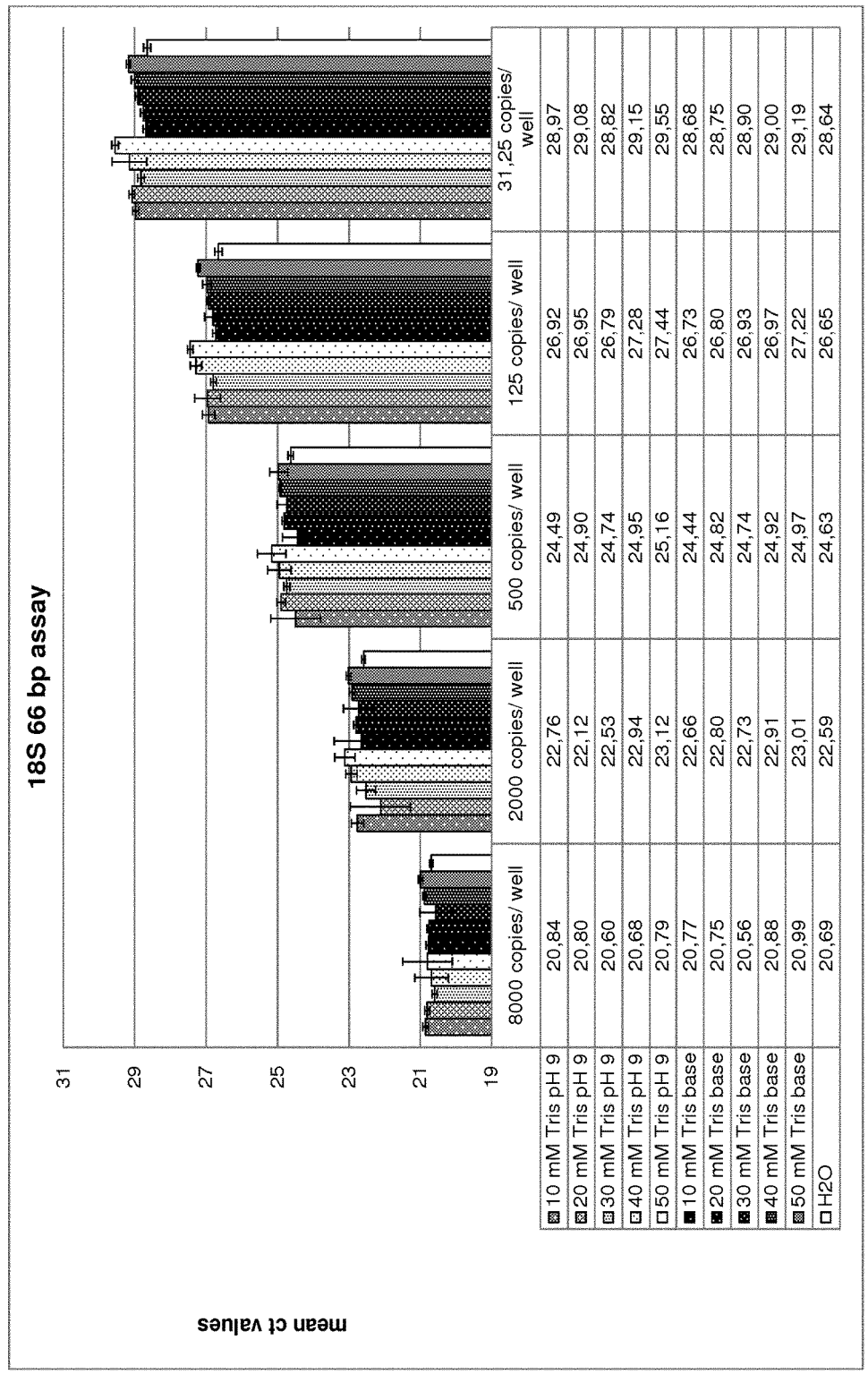
FIG. 14: Detection of target DNA in buffers with basic pH value, measured by the duplex 18S DNA assay.
Figure 14B:
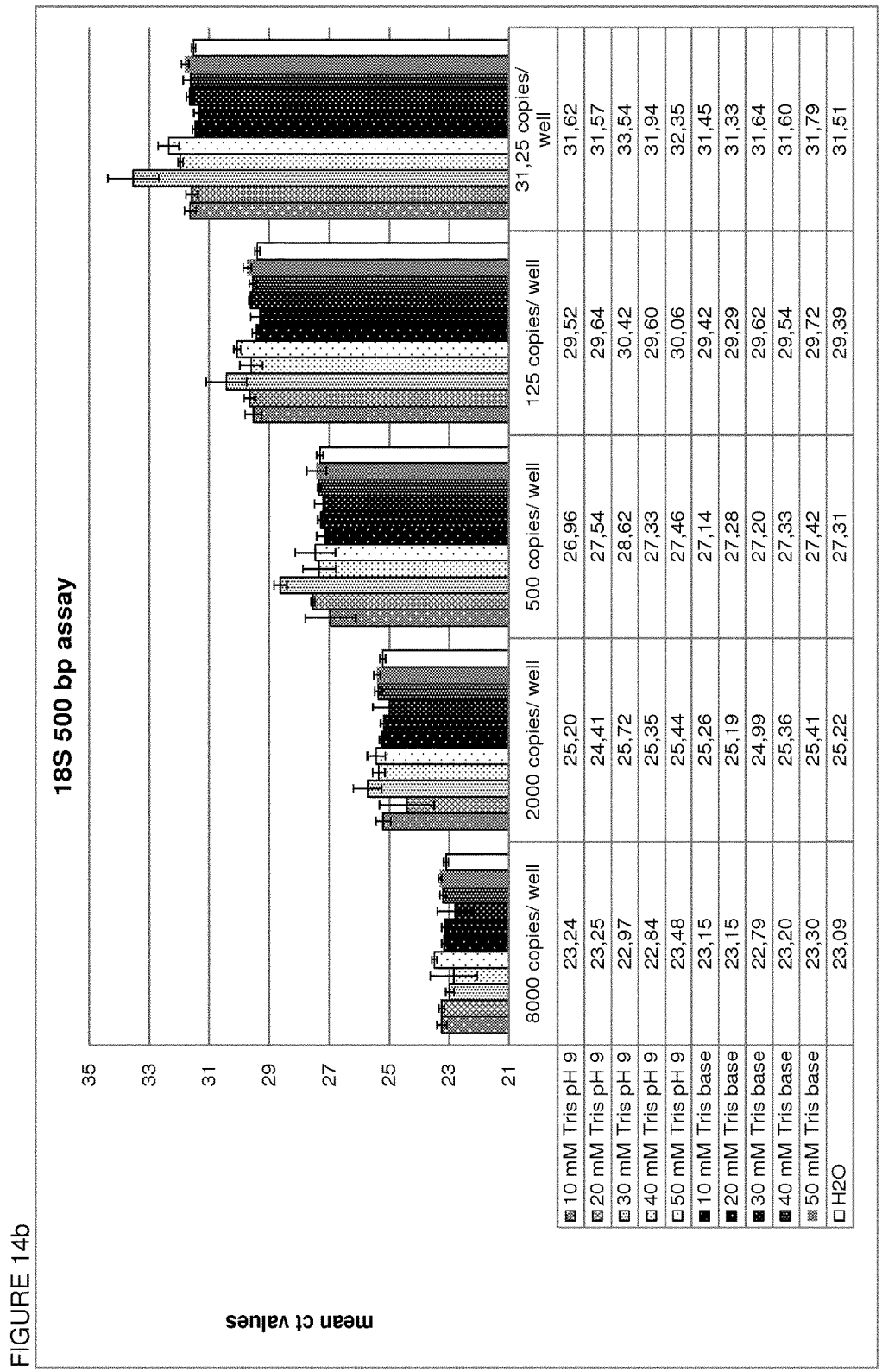

The results for the short 66 bp amplicon are shown in FIG. 14a, the results for the 500 bp amplicon are shown in FIG. 14b. Comparable Ct-values between tested elution buffers and pure water indicate that there is no significant PCR inhibition, neither for different DNA concentrations nor for the tested elution buffers. As can be seen, all tested buffers can readily be used for DNA elution and do not inhibit the downstream PCR reaction.

Figure 15A:
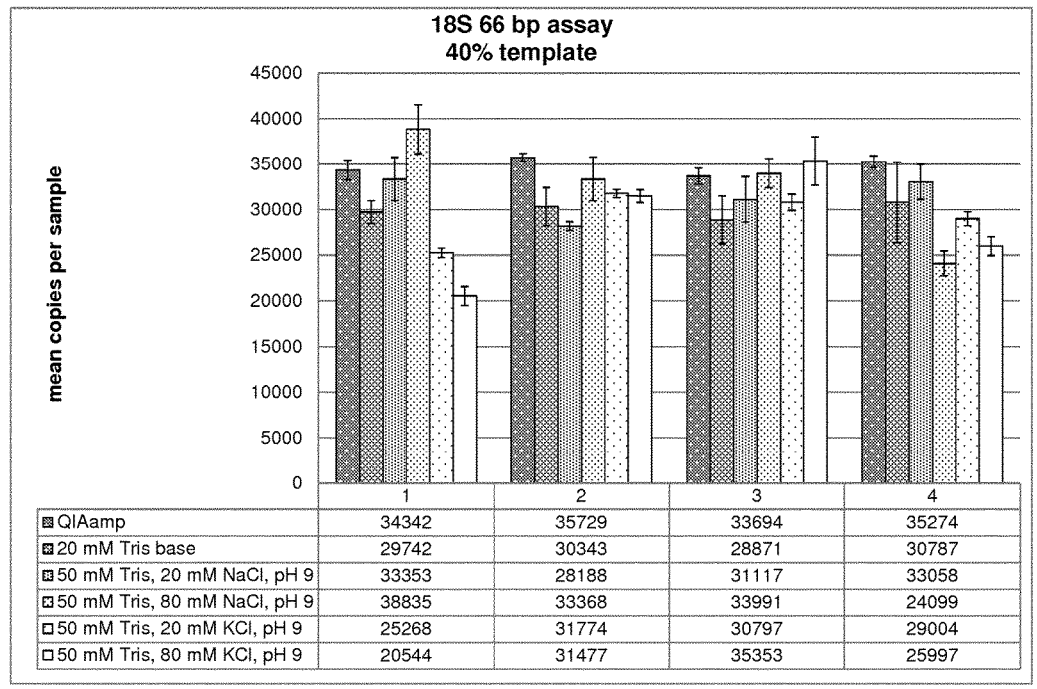
FIG. 15: Low yield recovery of longer DNA fragments in low salt elution buffers.

Example 14: Selective Elution of Short DNA Fragments at Highly Basic pH Values Different elution buffers were tested for elution of DNA with various sizes. 4 replicates of 5.8 ml pooled plasma were processed as described in example 11 for the QIAsymphony SP protocol. Following DNA binding to the beads, two wash steps with RNAse free water+0.1% TritonX-100 were performed, followed by elution with 150 µl using 5 different Tris buffers as shown in FIG. 15a. Eluted DNA was analysed using the 18S rDNA duplex assay for the 66 bp amplicon. For the 500 bp amplicon only data for 20 mM Tris (free base, ~pH 10.2) and the QIAamp CNA Kit as reference is shown.

Figure 15B:
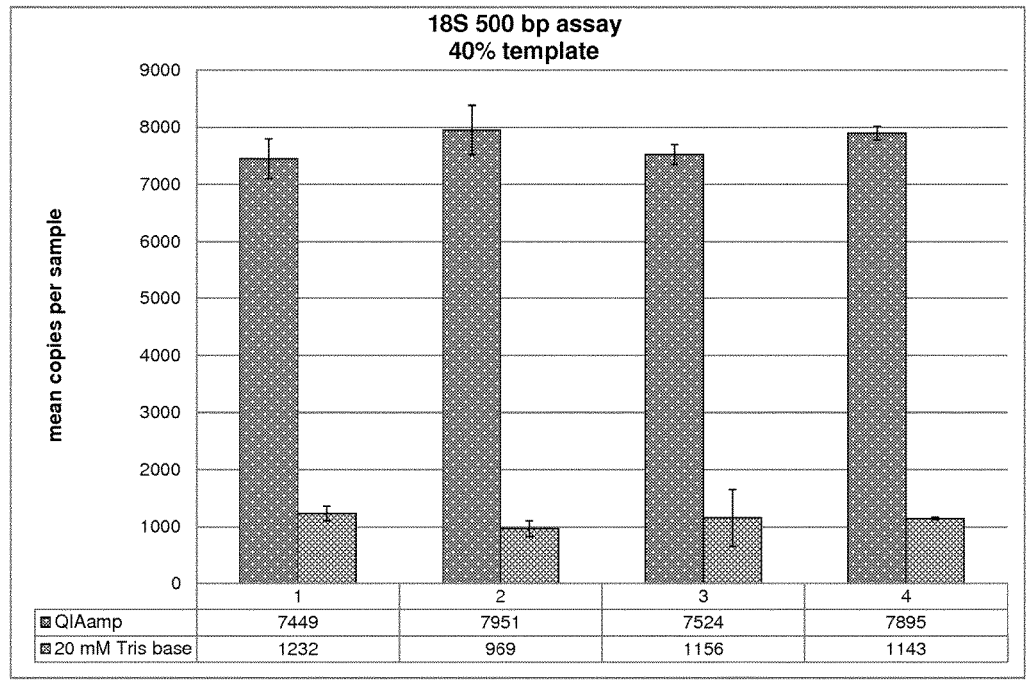

FIG. 15a depicts the result for the 66 bp amplicon obtained from pooled plasma samples, the result for the 500 bp amplicon is shown in FIG. 15b. For the 66 bp amplicon, the results are comparable between all replicates and also the DNA yields obtained with different elution buffers are comparable to the QIAamp CNA Kit reference. For the 500 bp amplicon, however, DNA yield was very low as compared to the reference. Thus, when using the method of the invention, selective elution of shorter DNA fragments (66 bp versus 500 bp) is possible using 20 mM Tris (free base ~pH 10.2) for elution.

Figure 16:
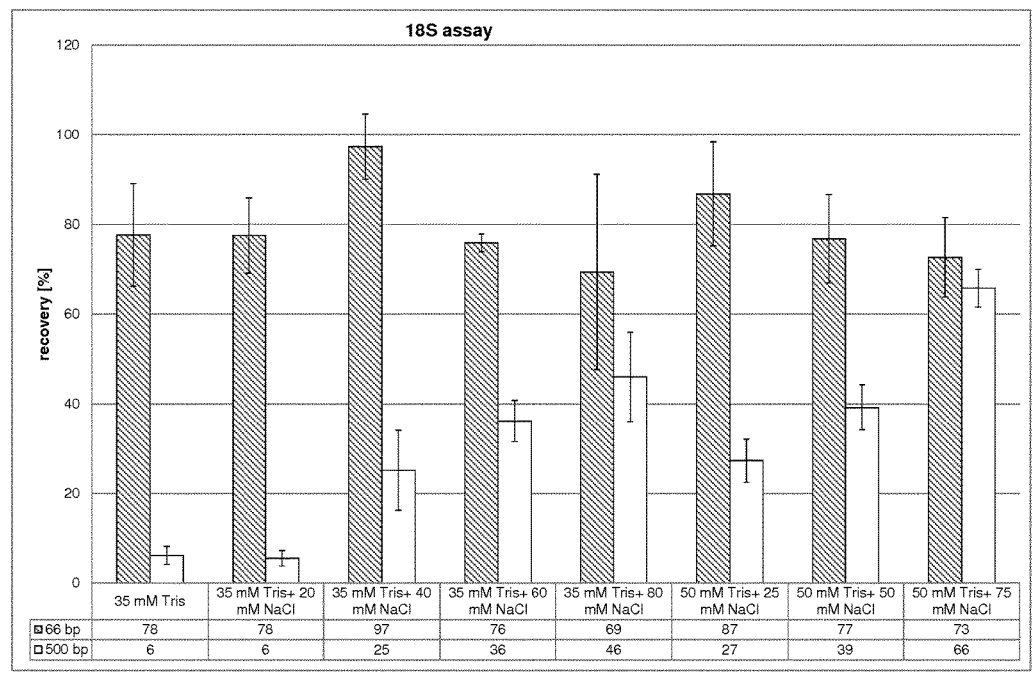
FIG. 16: Salt dependency and size selection, recovery of longer DNA fragments in high-salt elution buffers, measured by the dual 18S detection assay.

Example 15: Salt Dependent Elution of Longer DNA Versus Shorter DNA Fragments ccfDNA was detected using the 18S duplex assay. 5.8 ml plasma samples were processed as described in example 11. Following DNA binding to the beads, two wash steps with RNAse free water+0.1% TritonX-100 were performed, followed by elution with 150 µl using 5 different Tris buffers. ccf DNA isolated with the QIAamp CNA Kit served as a reference. % recovery using the QIAsymphony SP protocol (compared to the QIAamp CNA Kit) is shown in FIG. 16. Tris molarity and salt concentration seem to have no influence on the recovery of small DNA fragments (18S rDNA 66 bp amplicon). However, for longer DNA fragments (18S rDNA 500 bp amplicon), DNA recovery increases by using higher salt concentrations. Thus, by varying the salt concentration in the elution buffer, it is possible to influence and adjust the size of the eluted nucleic acids.

Figure 17:
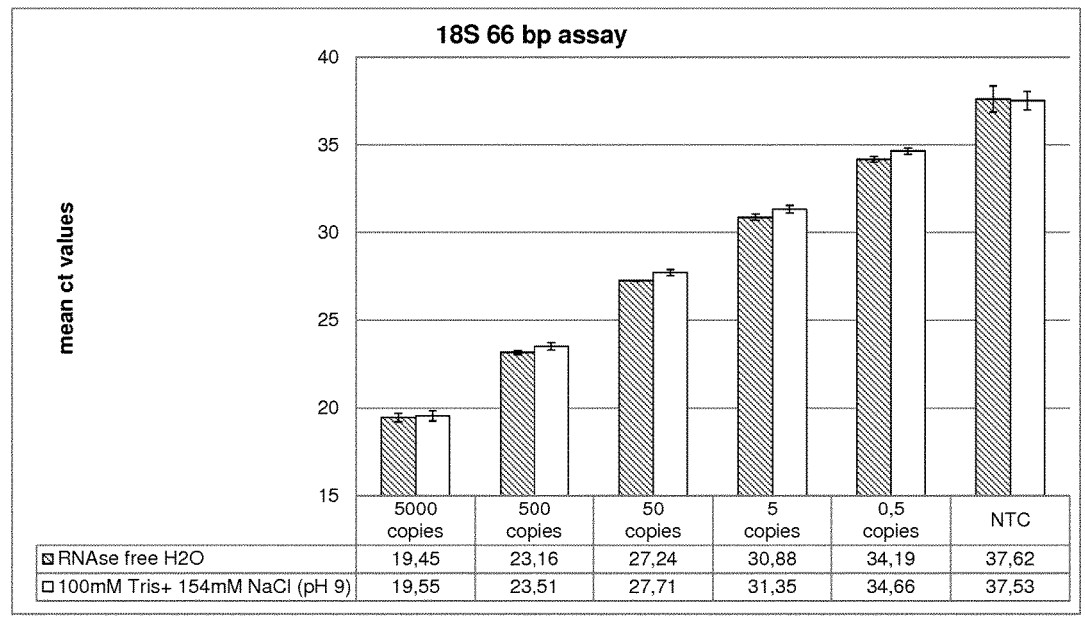
FIG. 17: PCR compatibility, no PCR inhibition of elution buffer spiked with different amounts of target DNA.

Example 16: PCR Compatibility of Different Elution Buffers ccfDNA was detected using the 18S duplex assay. Varying amounts of male human genomic DNA (0 to 5.000 copies) was spiked in RNAse free water (reference) and 100 mM Tris+154 mM NaCl, pH 9.20% of template volume ccf DNA was used in the real-time PCR reaction. The results for the 66 bp amplicon are shown in FIG. 17. Comparable Ct-values between the tested elution buffer and pure water indicate that there is no PCR inhibition for different DNA concentrations, at least not in the range of up to 5.000 copies.

Figure 18A:
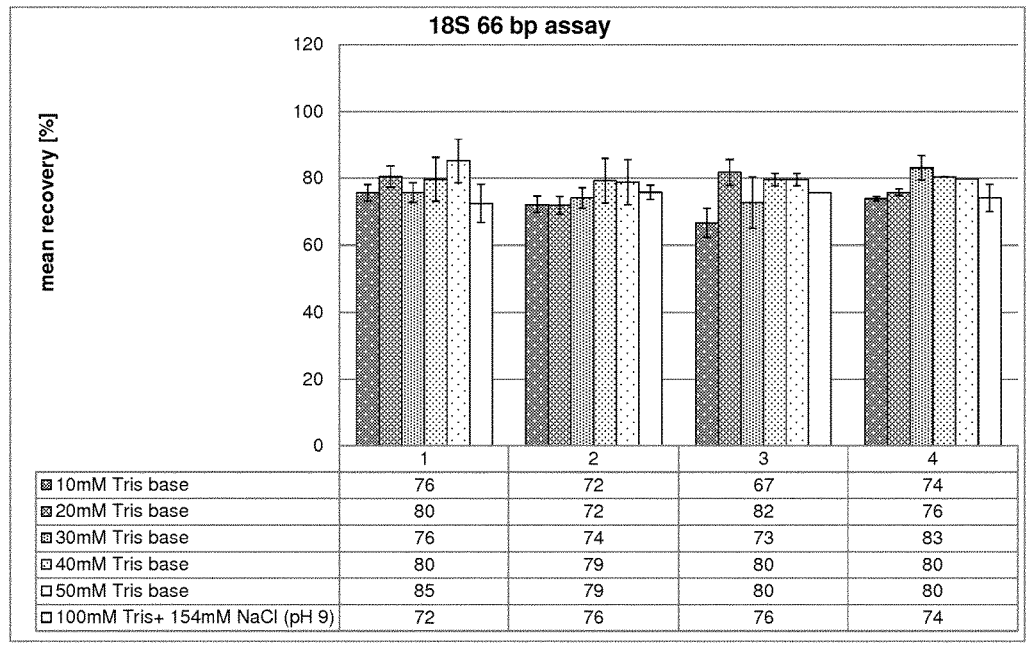
FIG. 18: Size-selective elution of shorter DNA fragments at basic pH without additional salt, measured by dual 18S DNA detection.
Figure 18B:
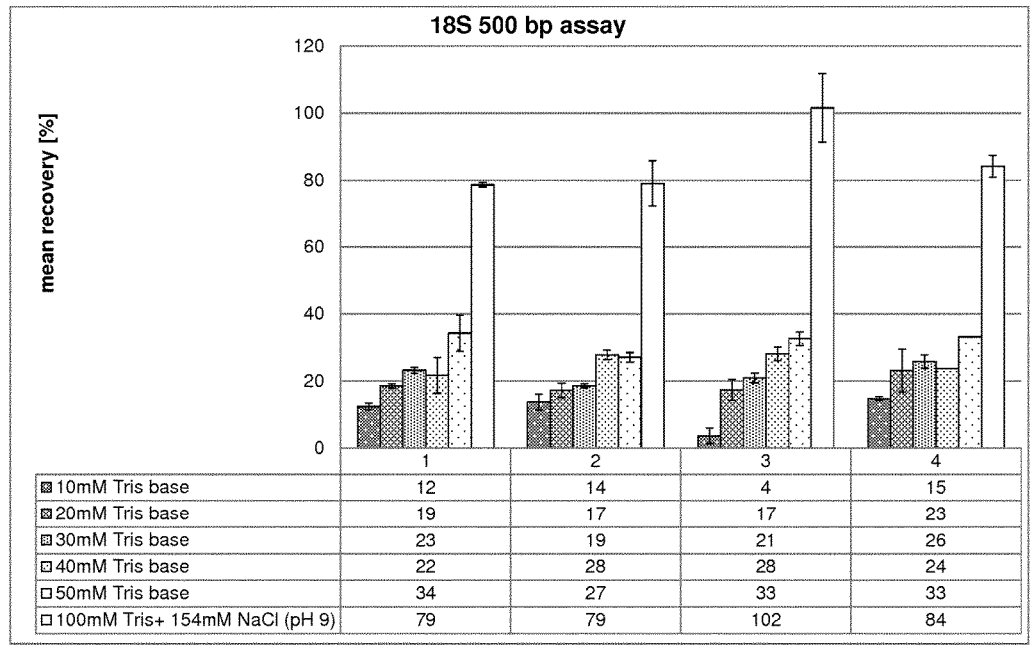

Example 17: Preferred Elution of Shorter DNA Fragments with Elution Buffers of Varying Molarity, in the Absence of Salt and at Highly Basic pH ccfDNA was detected using the 18S duplex assay. 4 replicates of 5.8 ml pooled plasma samples were processed as described in example 11. Following DNA binding to the beads, two wash steps with RNAse free water+0.1% TritonX-100 were performed, followed by elution with 150 µl using 5 different Tris buffers (10-50 mM Tris base and 100 mM Tris+154 mM NaCl, pH 9). ccf DNA isolated with the QIAamp CNA Kit served as reference. 10% template volume was used in the real-time PCR reaction. The results are shown in FIGS. 18a and 18b. All results are comparable between the tested replicates 1-4. For the shorter DNA fragments (66 bp amplicon) the DNA yields obtained after using elution buffers with different molarities are comparable to the DNA yields obtained with a salt-containing buffer and to the reference. However, the DNA yield of longer DNA fragments (500 bp amplicon) is very low for the tested buffers without NaCl, compared to the salt-containing buffer and the reference. Thus, a preferred elution of shorter DNA fragments (66 bp amplicon) is possible using for example a Tris buffer at varying molarities without additional salt at ~pH 10.2.

Example 18: Size Selection by Adjusting Elution Conditions, in Particular pH Value and Salt Content of the Elution Buffer ccfDNA was detected using the 18S duplex assay. 5.8 ml plasma samples were processed as described in example 11.

Figure 19:
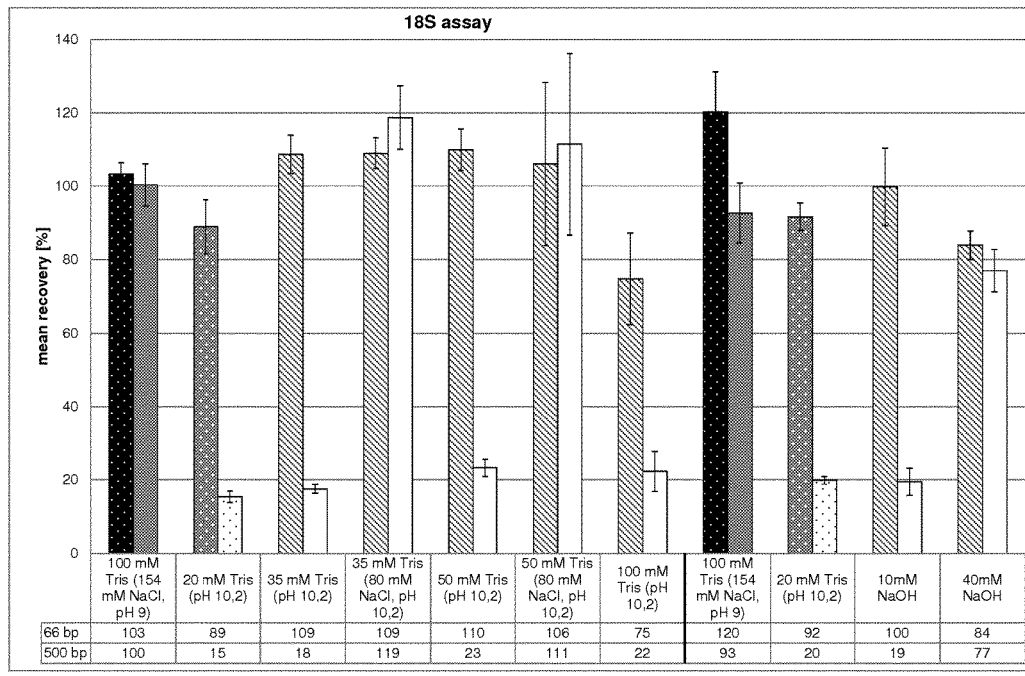
FIG. 19: Size-selective enrichment of ccf DNA using elution buffers with varying pH and salt concentration.

Following DNA binding to the beads, two wash steps with RNAse free water+0.1% TritonX-100 were performed, followed by elution with 150 µl using different Tris buffers or NaOH. 10% of the eluted DNA was used as template in the real-time PCR reaction. % recovery compared to ccf DNA isolated with the QIAamp CNA Kit was analysed. The results are depicted in FIG. 19. Salt addition or using NaOH for elution increases recovery of longer DNA fragments (see 500 bp amplicon). Thus, size selection is possible by adjusting specific elution conditions concerning salt concentration and pH value.

Example 19: Size Selection by Adjusting Elution Conditions, in Particular pH Value and Salt Content of the Elution Buffer In this experiment different elution buffers were tested for eluting DNA fragments with different lengths. ccf DNA was isolated from blood plasma and detected using the APP assay for four different amplicon length. Isolation and detection was essentially done as described in example 18. The APP assay was performed for the APP amplicon lengths of 67 bb, 180 bp, 306 bp and 476 bp, and all DNA fragments were amplified the same way. DNA recovery was compared to ccf DNA isolated with the QIAamp CNA Kit.

Figure 20:
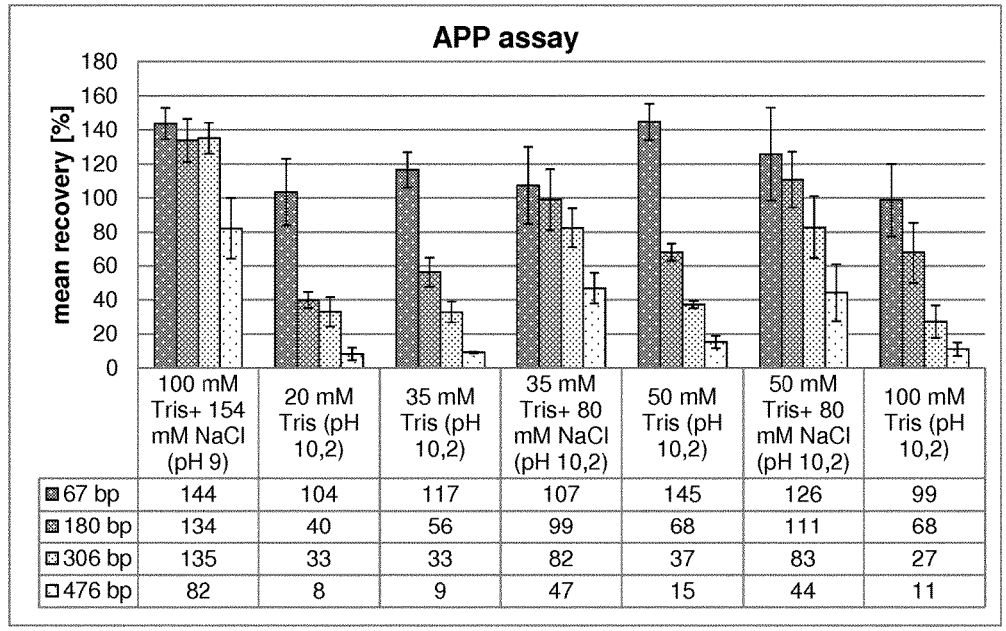
FIG. 20: Salt-dependent enrichment of DNA fragments with a defined size, measured by using the APP assay.

The results are shown in FIG. 20. Salt addition to elution buffer increases recovery of longer DNA fragments. Thus, a size selective elution can be achieved by adjusting the salt concentrations. This means in essence, that the more salt is used, the higher is the DNA recovery rate of longer DNA fragments.

Figure 21:
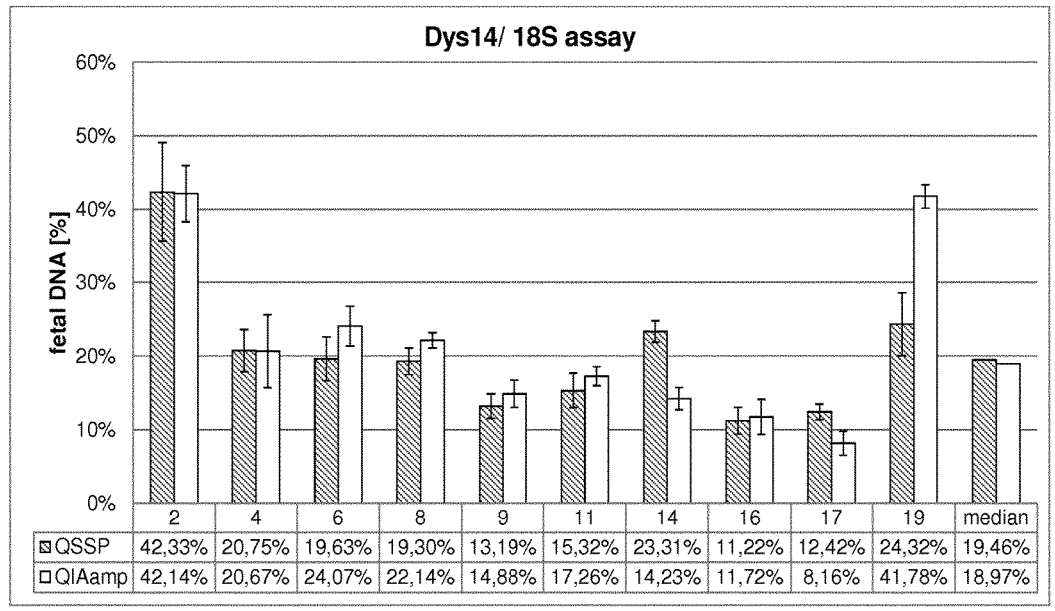
FIG. 21: Complete extraction of fetal DNA from maternal plasma, measured using a Dys14 assay.

Example 20: Recovery of Fetal DNA with the Automated Method of the Invention The automated ccf DNA isolation protocol of the invention was compared to the QIAamp CNA Kit reference method for the isolation of fetal DNA from maternal plasma. After isolation, fetal DNA was detected using the Dys14/18S assay. 4 ml maternal plasma was used as sample input volume for the QIAsymphony SP protocol, while 0.4-1 ml was used for the QIAamp CNA Kit. The QIAsymphony SP protocol was essentially done as described in example 11. Two wash steps were performed using 35 mM Tris at pH 7.2+0.1% TritonX-100. Bound DNA was eluted with 35 mM Tris+80 mM NaCl (pH 10.2) in 100 µl elution volume. Detection of fetal DNA was done using the Dys14/18S assay as described in example 11. 10% of the template volume was used in a real-time PCR reaction. Finally, the ratio between DNA copies of Dys14/18S assay was calculated to determine the fetal DNA fraction in %. The results are depicted in FIG. 21. The percentage of detected fetal DNA within the ccf DNA is comparable for the QIAsymphony SP protocol (QSSP) and the QIAamp CNA Kit (QIAamp). Fetal DNA can be completely extracted using the automated method of the invention.

Figure 22:
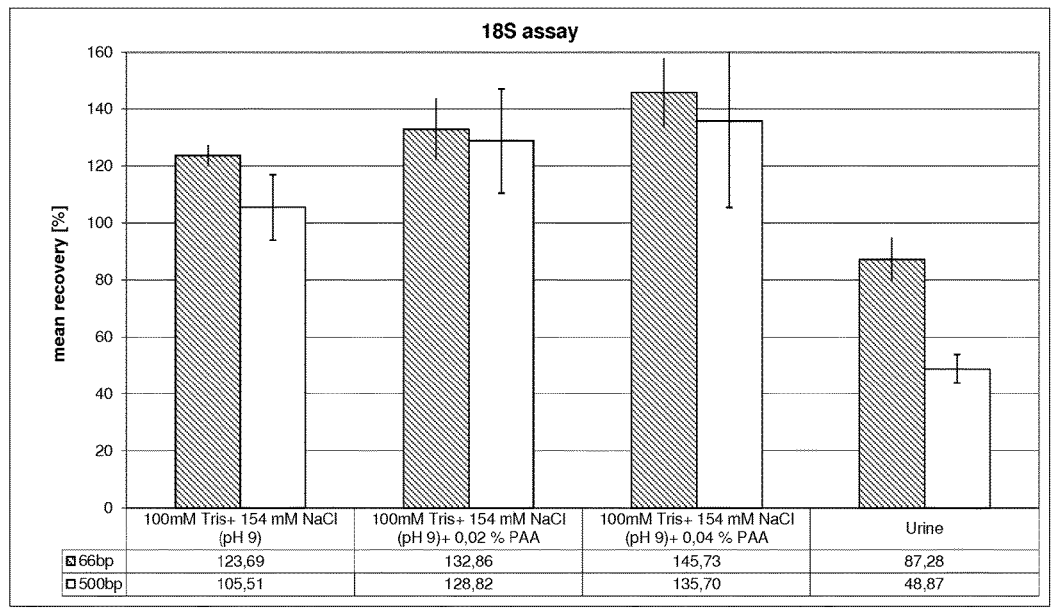
FIG. 22: PAA addition improves DNA recovery, as measured by the duplex 18S DNA assay.

Example 21: ccf DNA Enrichment from Urine Samples, and Polyacrylic Acid Increases Elution Efficiency ccfDNA was detected using the 18S duplex assay. 3 ml plasma samples were manually processed. Additionally, urine (3 ml) was processed. Two wash steps were performed using 100 mM Tris+154 mM NaCl (pH 7.2)+0.1% TritonX-100. Bound DNA was eluted with 100 mM Tris+154 mM NaCl (pH 9.0) (was also used for urine), 100 mM Tris+154 mM NaCl (pH 9.0)+0.02% PAA, or with 100 mM Tris+154 mM NaCl (pH 9.0)+0.04% PAA. The elution volume was 150 µl. Eluted ccf DNA was quantified using in the dual 18S duplex assay. DNA recovery was compared to ccf DNA processed with the QIAamp CNA Kit. The results are shown in FIG. 22. Addition of PAA results in a higher DNA recovery of both the 66 bp and the 500 bp fragment. Ccf DNA enrichment from urine is also possible.

Figure 23A:
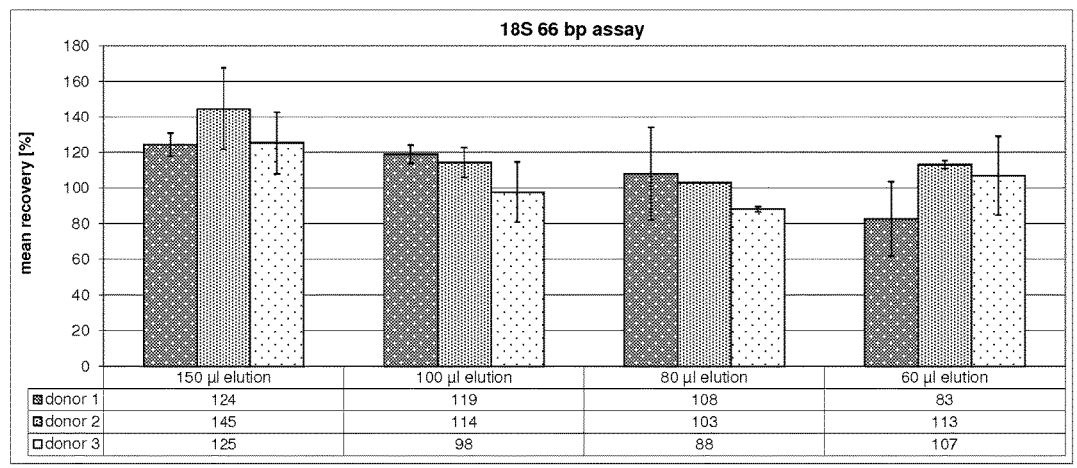
FIG. 23: DNA isolation efficiency using different elution volumes.
Figure 23B:
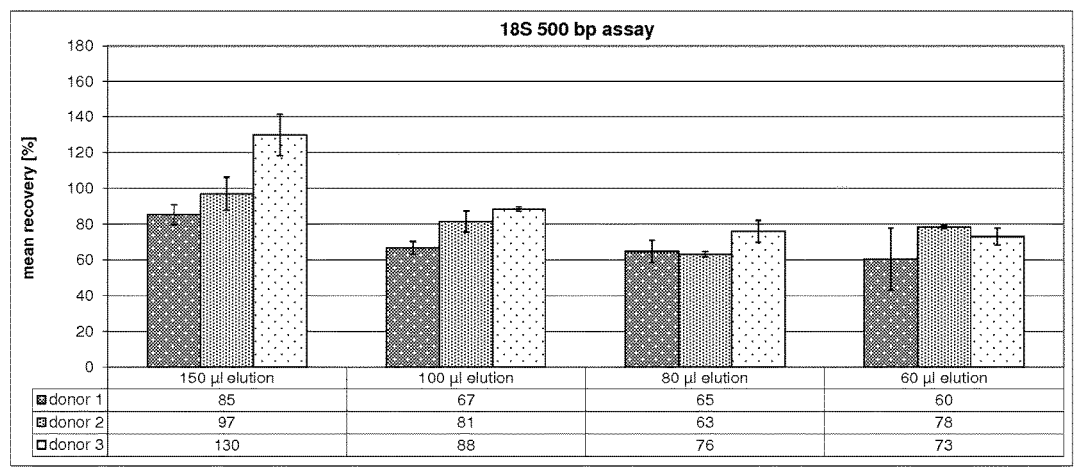

Example 22: ccf DNA is Readily Eluted from Beads Using Different Elution Volumes ccfDNA was detected using the 18S duplex assay (66 and 500 bp amplicon). 3 ml plasma samples derived from 3 different donors were manually processed as described above. Two wash steps were performed using 100 mM Tris+154 mM NaCl (pH 7.2)+0.1% TritonX-100. Bound DNA was eluted with 100 mM Tris+154 mM NaCl (pH 9), using 60, 80, 100 or 150 µl elution volume. Eluted ccf DNA was quantified with the dual 18S rDNA assay. The results for the detection of the 66 bp amplicon are shown in FIG. 23a, and those for the 500 bp amplicon in FIG. 23b. The reduction of the elution volume has no significant effect on DNA recovery. However, an elution volume as low as possible is advantageous in order to obtain a high enrichment factor. A high enrichment factor may be achieved by using a high sample input volume and a low elution volume.

Example 23: Highly Efficient Binding and Release of Ccf DNA from Plasma 3 ml plasma samples derived from 3 different donors were manually processed as described above. After ccf DNA binding to the beads, the supernatant fraction was saved. Two wash steps were performed using 100 mM Tris+154 mM NaCl (pH 7.2)+0.1% TritonX-100. Bound DNA was eluted with a 2-step protocol: First, elution was done with 100 mM Tris+154 mM NaCl (pH 9) in 150 µl elution volume. Then, residual DNA was released from beads with 150 µl 40 mM NaOH. Before qPCR detection, the NaOH fraction was neutralized. Detection of ccf DNA was performed using the dual 18S rDNA assay for the 66 bp and the 500 bp amplicon as described in example 2.

Figure 24:
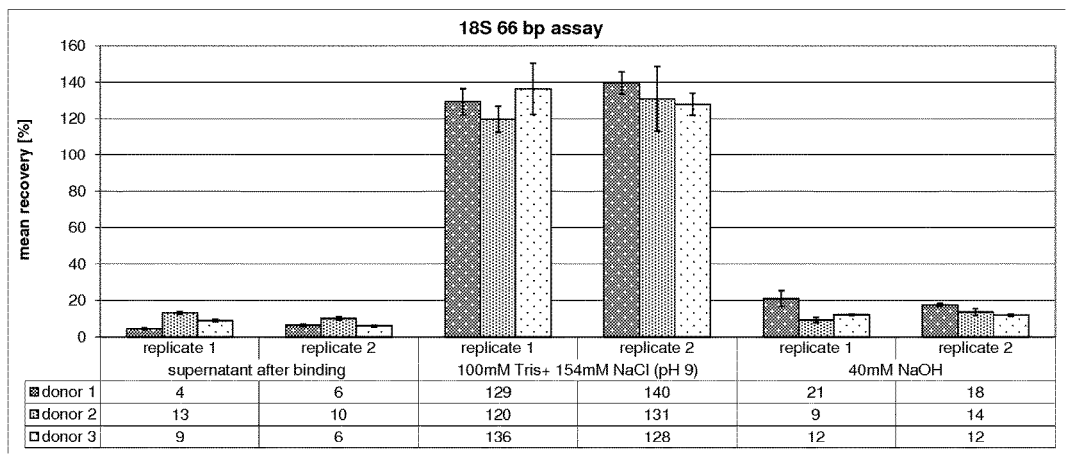
FIG. 24: Highly efficient DNA binding and release into elution buffer, measured by the dual 18S DNA detection assay.

The results are shown in FIG. 24. Basically no unbound ccf DNA can be detected in the supernatant. Also, no residual ccf DNA can be detected in the NaOH elution fractions. Thus, ccf DNA can be completely bound from plasma to magnetic beads and again released into an elution buffer. This results in good recovery rates.

Example 24: Cleaning of Eluates Prior to PCR Detection is Obsolete—No PCR-Inhibitory Effect in Eluates In this experiment it was tested whether the eluates may comprise PCR-inhibitors. For that purpose, 3 ml plasma samples derived from 2 different donors were manually processed as described above. Two wash steps were performed using RNase free water+0.1% TritonX-100. Bound DNA was eluted with a 2-step protocol: The first elution was done with 100 mM Tris+154 mM NaCl (pH 7.2) in 150 µl elution volume. The second elution was done with 100 mM Tris+154 mM NaCl (pH 9.0), again in 150 µl elution volume. 100 µl of the first and second eluate was used as sample input for a cleanup using the QIAamp CNA Kit. 5% template volume of the remaining 50 µl fraction and of the cleaned-up 100 µl fraction were then used for real time PCR detection according to the dual 18S rDNA assay (66 bp and 500 bp amplicon). ccf DNA isolated with the QIAamp CNA Kit served as reference.

Figure 25A:
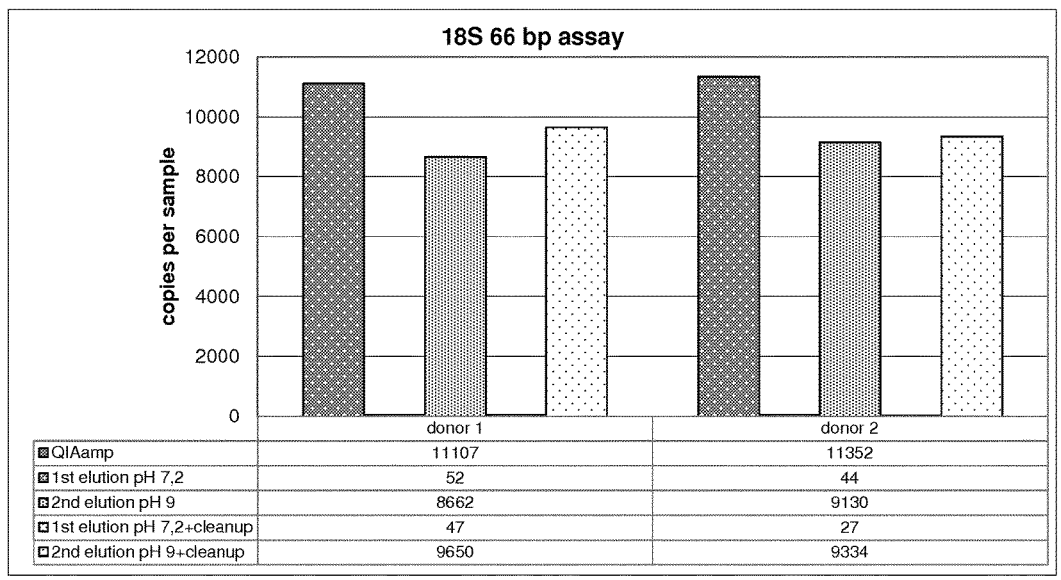
FIG. 25: PCR-detection of isolated DNA is unaffected by elution buffer components.
Figure 25B:
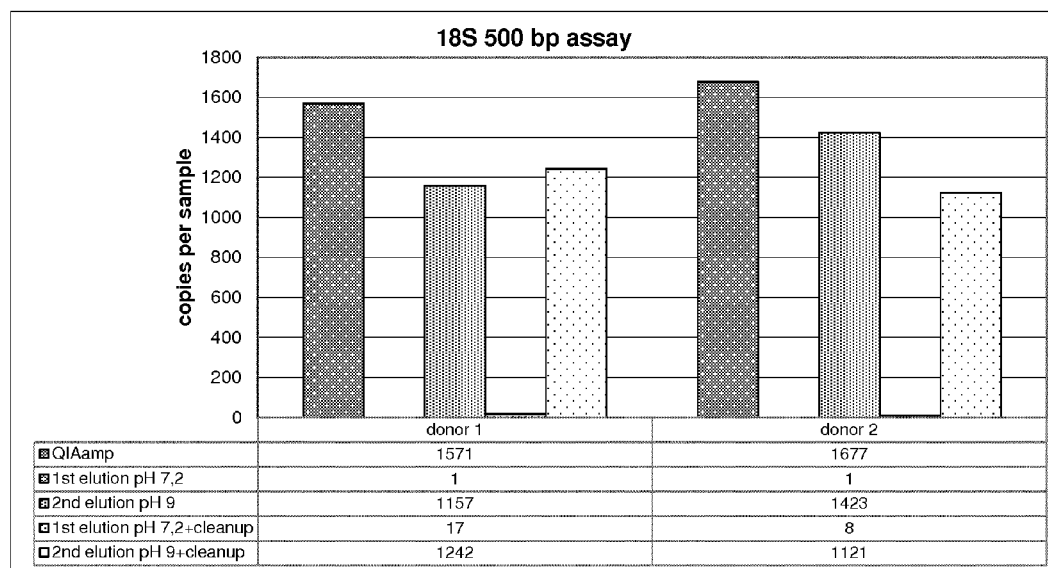

The results for the 66 bp amplicon are shown in FIG. 25*a*, the results for the 500 bp amplicon in FIG. 25*b*. The 66 bp and the 500 bp amplicons of the 18S rDNA can only be detected in pH 9.0 eluates, but not in pH 7.2 eluates. This means that elution is highly pH-dependent and thus, can be controlled by the pH value. Detection of the 66 bp and the 500 bp fragments is equally efficient in direct and in cleaned-up eluates. Thus, no PCR-inhibitory effect can be observed in eluates.

Figure 26:
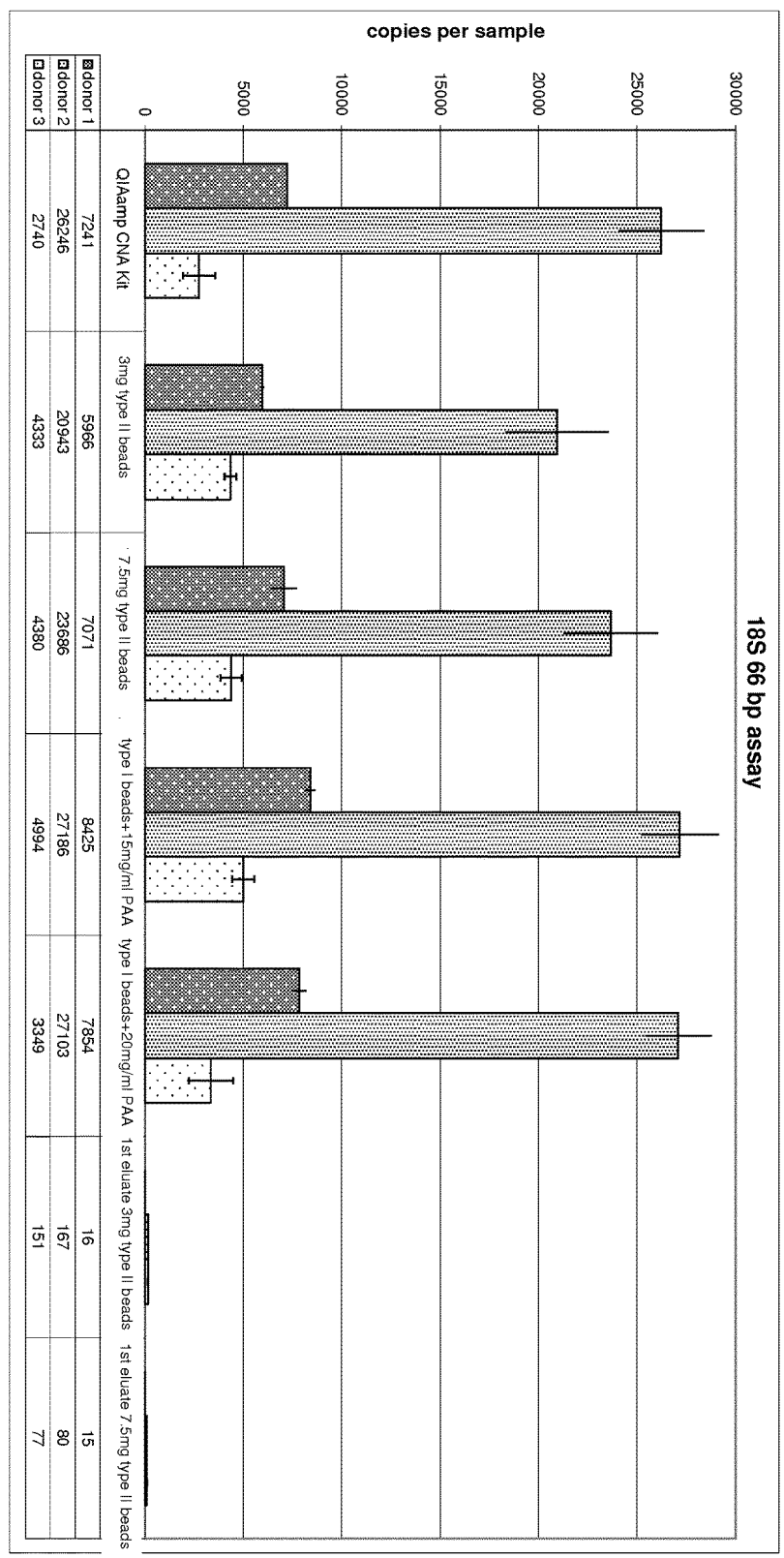
FIG. 26: pH-value and bead-volume dependent enrichment of DNA.
Figure 27A:
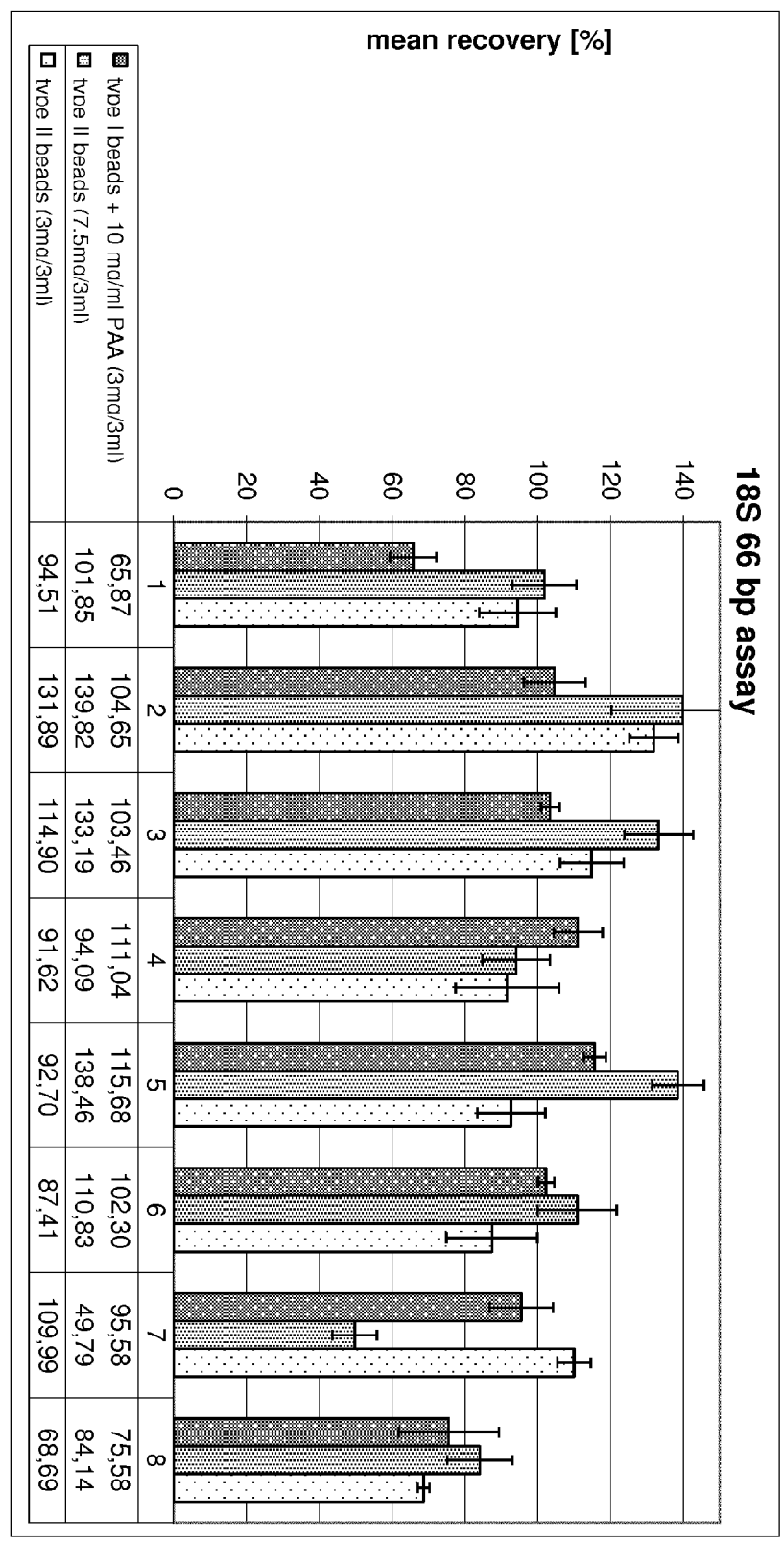
FIG. 27: Comparable DNA enrichment using type I or type II beads, measured using the 18S detection assay.
Figure 27B:
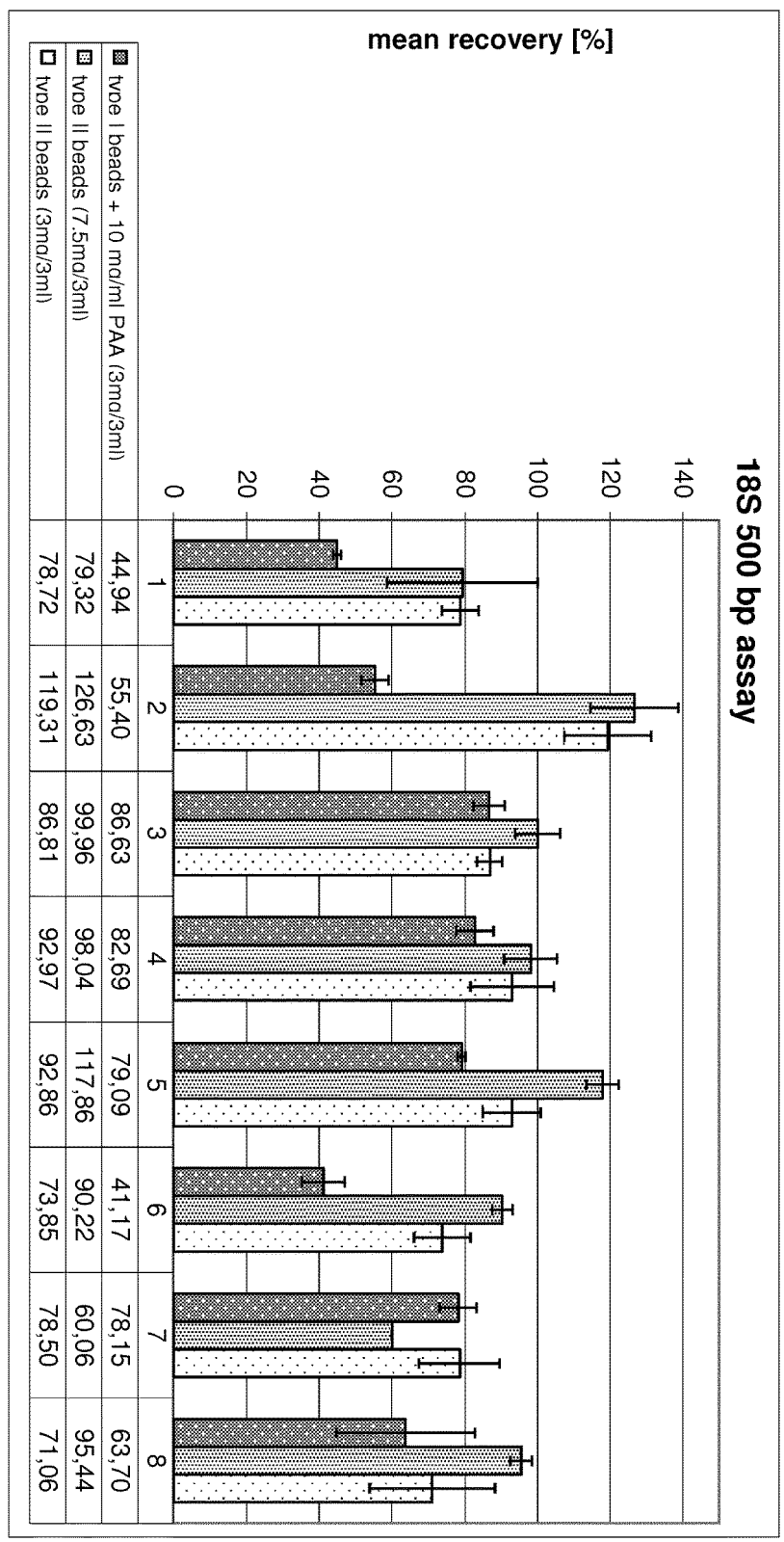

Example 25: Comparison Between Bead Volume, Type and Influence of PAA 3 ml plasma samples derived from 3 different donors were manually processed as described above. 3 mg or 7.5 mg Type II beads were used. Additionally, Type I beads were tested, treated with PAA. The beads were incubated overnight in an aqueous PAA solution, the supernatant was discarded. After binding two wash steps were performed using RNase free water+0.1% TritonX-100. Bound DNA was eluted from type II beads using a 2-step elution protocol as described in additional example 24. Bound DNA was eluted from Type I beads either with 150 µl of 100 mM Tris+154 mM NaCl (pH 9.0)+15 mg/ml PAA or with 150 µL of 100 mM Tris+154 mM NaCl (pH 9.0)+20 mg/ml PAA. ccf DNA isolated with the QIAamp CNA Kit served as reference. 5% of the eluted volume was used in the real-time PCR. As shown in FIG. 26, an increase of the bead volume leads to a better DNA recovery. Type I and Type II beads lead to comparable results, if PAA is added to the Type I beads. Furthermore one can observe, that no DNA is eluted from the type II beads during the 1$^{st}$ elution step.

Example 26: Comparison Between Different Bead Types and Volumes 3 ml plasma samples derived from 8 different donors were manually processed as described in example 25. However, for binding, 3 mg PAA treated Type I beads and 3 mg or 7.5 mg Type II beads was added for binding ccf DNA. After the two washing steps, bound DNA was eluted from Type I beads with 150 µl of 100 mM Tris+154 mM NaCl (pH 9.0), while bound DNA was eluted from Type II beads using a 2-step elution protocol as described in example 24. 5% of the eluted volume was used for real time PCR detection according to the dual 18S rDNA assay (66 bp and 500 bp amplicon). ccf DNA isolated with the QIAamp CNA Kit served as control.

Example 27: Enrichment of ccfDNA from Serum

In this experiment ccf DNA recovery after binding from serum and from plasma samples was compared. 4 ml plasma or serum samples were manually processed as described above. Following binding, no wash steps were performed. The supernatant obtained from plasma was saved for further analysis. DNA bound to the beads was eluted using 100 mM Tris+154 mM NaCl (pH 8.5) in 1 ml elution volume. The eluates and supernatant were processed using the QIAamp CNA Kit, and DNA was eluted in 60 µl elution volume. 10% of the eluted volume was used in the dual 18S DNA assay. ccf DNA isolated with the QIAamp CNA Kit served as reference.

Figure 28:
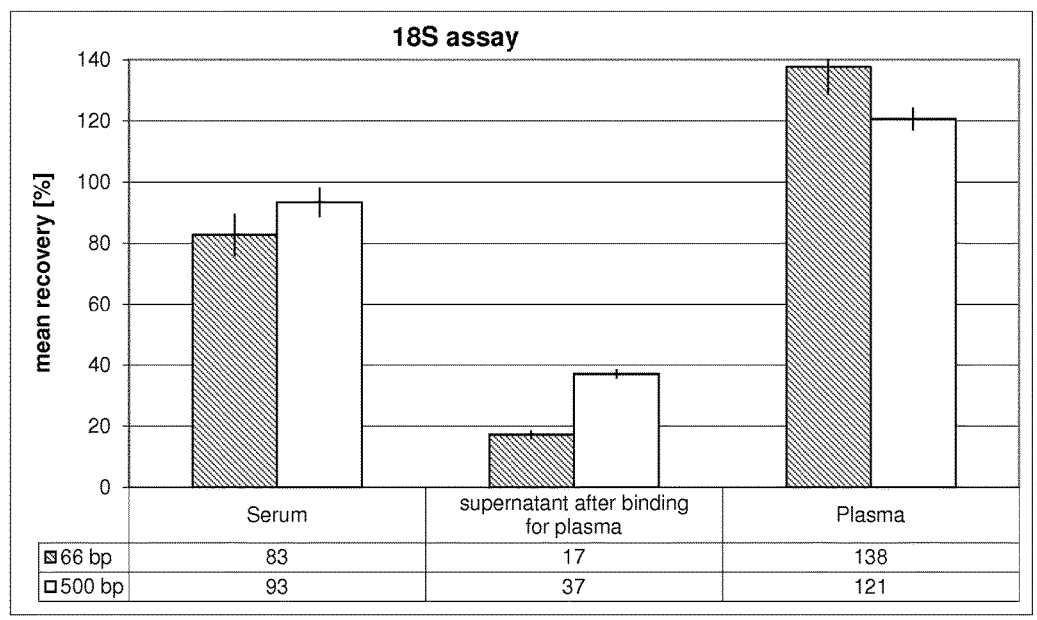
FIG. 28: DNA enrichment from serum.

FIG. 28 shows that ccf DNA can be completely bound from plasma and can also be eluted and thus recovered from the beads. Furthermore, ccf DNA can also be recovered from serum samples.

The invention claimed is:

1. A method for isolating extracellular nucleic acids from a sample by binding the extracellular nucleic acids to a solid phase which carries anion exchange groups, comprising:
    a. acidifying the sample to establish the binding conditions and binding the extracellular nucleic acids to the solid phase in a binding mixture having a first pH of ≤6.5 which allows binding the extracellular nucleic acids to the anion exchange groups of the solid phase, wherein the solid phase is provided by magnetic particles;
    b. separating the solid phase with the bound extracellular nucleic acids from the remaining sample;
    c. optionally washing the extracellular nucleic acids; and
    d. eluting extracellular nucleic acids from the solid phase, wherein elution occurs at a second pH lying in the range of ≥8 to ≤14;

wherein the sample is a cell-free or cell-depleted sample which was obtained from a cell-containing sample by removing cells, and wherein the extracellular nucleic acids are extracellular DNA.

2. The method according to claim 1, wherein in step a., the sample makes up at least 85% of the volume of the binding mixture.

3. The method according to claim 2, wherein the solid phase in step a. comprises magnetic particles that carry tertiary amino groups; and
    wherein in step d., the length of the nucleic acids that are eluted and the length of the nucleic acids that remain bound to the anion exchange matrix is controlled by adjusting the elution conditions, and wherein nucleic acids having a length of about 1000 nt or more, 700 nt or more, or 500 nt or more predominantly remain bound to the solid phase in said elution step.

4. The method according to claim 3, wherein a selective elution of short nucleic acids is achieved in step d. by adjusting the concentration of positive charges on the surface of the solid phase so that only the longer nucleic acid molecules remain bound to the solid phase during step d. while the smaller nucleic acids are eluted, wherein the cut-off value is controlled by the choice of the pH value that is used during elution.

5. The method according to claim 1, wherein in step d. the nucleic acids are selectively eluted according to their sizes, wherein the cut-off value is controlled by the pH value and/or the salt concentration used during the elution.

6. The method according to claim 1, wherein in step d., extracellular nucleic acids are selectively eluted according to their sizes, said size fractionating elution step comprises eluting a portion of the extracellular nucleic acids bound to the solid phase at the second pH, and the average length of the nucleic acids eluted from the solid phase in this step is shorter than the average length of the nucleic acids which remain bound to the solid phase.

7. The method according to claim 2, wherein the first pH in
    step a. is ≤6;
    and
    wherein in step d., extracellular nucleic acids are selectively eluted according to their sizes, said size fractionating elution step comprises eluting a portion of the extracellular nucleic acids bound to the solid phase at the second pH, wherein the average length of the nucleic acids eluted from the solid phase in this step is shorter than the average length of the nucleic acids which remain bound to the solid phase, and nucleic acids having a length of about 1000 nt or more, 700 nt or more, or 500 nt or more predominantly remain bound to the solid phase in said elution step.

8. The method according to claim 1, wherein step a. comprises adjusting the pH of the sample to the first pH.

9. The method according to claim 1, wherein step a. has one or more of the following characteristics:
   i) the first pH is below the pKa value of a protonatable group of the anion exchange groups of the solid phase;
   ii) at least one acidifying reagent and/or compound is added to the sample to adjust the first pH;
   iii) the first pH is ≤6;
   iv) the first pH lies in a range selected from 4 to 6.5, 4.5 to 6.5, 5 to 6.5 and 5 to 6;
   v) the sample makes up at least 90%, at least 95% or at least 97% of the volume of the binding mixture; and/or
   vi) at least one acidic solution is added to the sample to adjust the first pH.

10. The method according to claim 1, wherein the sample has one or more of the following characteristics:
   a) the cell-containing sample from which the cell-free or cell-depleted sample was obtained is selected from the group consisting of whole blood, plasma, serum, lymphatic fluid, urine, liquor, cerebrospinal fluid, ascites, milk, bronchial lavage, saliva, amniotic fluid, semen/seminal fluid, body fluids, body secretions, nasal secretions, vaginal secretions, wound secretions and excretions;
   b) it is plasma or serum;
   d) it is plasma;
   e) it is a stabilized sample; and/or
   f) it is a stabilized plasma sample.

11. The method according to claim 1, wherein the isolated extracellular nucleic acids have one or more of the following characteristics:
   a) they are isolated as a portion of total nucleic acid isolated from the sample;
   b) they comprise circulating extracellular nucleic acids;
   c) they comprise disease related nucleic acids;
   d) they comprise tumor-associated or tumor-derived nucleic acids;
   e) they comprise inflammation related nucleic acids;
   f) they comprise fetal nucleic acids;
   g) they comprise viral nucleic acids;
   h) they comprise pathogenic nucleic acids; and/or
   i) they comprise mammalian extracellular nucleic acids.

12. The method according to claim 1, having one or more of the following characteristics:
   i) an elution solution is used in step d; and/or
   ii) in step d, extracellular nucleic acids are selectively eluted according to their sizes and wherein said size fractionating elution step comprises the following steps:
      aa) a portion of the extracellular nucleic acids bound to the solid phase is eluted therefrom at the second pH, wherein the average length of the nucleic acids eluted from the solid phase in this step is shorter than the average length of the nucleic acids which remain bound to the solid phase; and
      bb) optionally eluting extracellular nucleic acids which remain bound to the solid phase in step aa) from the solid phase at a third pH which is higher than the second pH.

13. The method according to claim 1, wherein the solid phase that is used for binding the extracellular nucleic acids has one or more of the following characteristics:
   (i) the solid phase carries a type of anion exchange group that is positively charged at the first pH;
   (ii) the solid phase carries a type of anion exchange group which comprises a protonatable group and the pKa value of the protonatable group is in the range of from 8 to 12 or 9 to 11;
   (iii) the solid phase carries a type of anion exchange group which is an amino group;
   (iv) the solid phase carries inert ligands which do not strongly bind to nucleic acids at the first pH wherein the inert ligand is an uncharged ligand comprising at least one hydroxyl group;
   (v) the solid phase carries the anion exchange groups and inert ligands in a ratio in the range of from about 1:1 to about 1:10, from about 1:2 to about 1:5 or about 1:3; and/or
   (vi) the surface of the solid phase is derivatized with a silane compound comprising the anion exchange group.

14. The method according to claim 13, wherein the amino group of the solid phase as defined in (iii) is a dialkylamino group.

15. The method according to claim 1, wherein the sample is a stabilized body fluid.

16. The method according to claim 1, further comprising one or more of the following steps:
   (i) purifying the isolated extracellular nucleic acids;
   (ii) processing and/or analyzing the isolated extracellular nucleic acids, wherein processing and/or analyzing the isolated extracellular nucleic acids comprises:
      aa) modifying the isolated extracellular nucleic acids;
      bb) contacting the isolated extracellular nucleic acids with at least one enzyme;
      cc) amplifying the isolated extracellular nucleic acids;
      dd) reverse transcribing the isolated extracellular nucleic acids;
      ee) cloning the isolated extracellular nucleic acids;
      ff) sequencing the isolated extracellular nucleic acids;
      gg) contacting the isolated extracellular nucleic acids with a probe;
      hh) detecting the isolated extracellular nucleic acids;
      (ii) identifying the isolated extracellular nucleic acids; and/or
      (jj) quantifying the isolated extracellular nucleic acids; and/or
   (iii) analyzing the isolated extracellular nucleic acids to identify, detect, screen for, monitor or exclude a disease, an infection and/or at least one fetal characteristic.

17. The method of claim 1, wherein
   the first pH in step a. is ≤6; and
   the method further comprises
   e. isolating the extracellular nucleic acids from the eluate.

18. The method according to claim 17, wherein the sample is plasma or serum.

19. The method according to claim 17, having one or more of the following characteristics:
   a) the sample is a stabilized sample;
   b) the method further comprises removing cells from the sample prior to step a.;
   c) (i) the method further comprises purifying the isolated extracellular nucleic acids;
      (ii) the method further comprises processing and/or analyzing the isolated extracellular nucleic acids, wherein processing and/or analysing the isolated extracellular nucleic acids comprises:
aa) modifying the isolated extracellular nucleic acids;
bb) contacting the isolated extracellular nucleic acids with at least one enzyme;
cc) amplifying the isolated extracellular nucleic acids;
dd) reverse transcribing the isolated extracellular nucleic acids;
ee) cloning the isolated extracellular nucleic acids;
ff) sequencing the isolated extracellular nucleic acids;
gg) contacting the isolated extracellular nucleic acids with a probe;
hh) detecting the isolated extracellular nucleic acids;
(ii) identifying the isolated extracellular nucleic acids; and/or
(jj) quantifying the isolated extracellular nucleic acids; and/or
(iii) analyzing the isolated extracellular nucleic acids to identify, detect, screen for, monitor or exclude a disease, an infection and/or at least one fetal characteristic;
d) i) an elution solution is used in step d;
ii) in step d, extracellular nucleic acids are selectively eluted according to their sizes and wherein said size fractionating elution step comprises the following steps:
aa) a portion of the extracellular nucleic acids bound to the solid phase is eluted therefrom at the second pH, wherein the average length of the nucleic acids eluted from the solid phase in this step is shorter than the average length of the nucleic acids which remain bound to the solid phase; and
bb) optionally eluting extracellular nucleic acids which remain bound to the solid phase in step aa) from the solid phase at a third pH which is higher than the second pH;
e) the solid phase that is used for binding the extracellular nucleic acids has one or more of the following characteristics:

(i) the solid phase carries a type of anion exchange group that is positively charged at the first pH;
(ii) the solid phase carries a type of anion exchange group which comprises a protonatable group and the pKa value of the protonatable group is in the range of from 8 to 12 or 9 to 11;
(iii) the solid phase carries a type of anion exchange group which is an amino group;
(iv) the solid phase carries inert ligands which do not strongly bind to nucleic acids at the first pH wherein the inert ligand is an uncharged ligand comprising at least one hydroxyl group;
(v) the solid phase carries the anion exchange groups and inert ligands in a ratio in the range of from about 1:1 to about 1:10, from about 1:2 to about 1:5 or about 1:3; and/or
(vi) the surface of the solid phase is derivatized with a silane compound comprising the anion exchange group; and/or
f) the sample makes up at least 85% of the volume of the binding mixture.

20. The method according to claim 1, wherein the solid phase is provided by magnetic particles which carry diethylaminopropyl groups.

21. The method according to claim 17, wherein the solid phase is provided by magnetic particles which carry diethylaminopropyl groups.

22. The method of claim 1, wherein the sample is split, and the resulting sample portions are processed in parallel, and wherein the method further comprises reunifying either the eluates or the anion exchange material prior to elution.

23. The method of claim 1, wherein the sample is a stabilized sample and wherein stabilization prevents the degradation of extracellular nucleic acids and/or prevents the contamination of the extracellular nucleic acids by intracellular nucleic acids.

24. The method of claim 17, wherein the sample is a cell-free of cell-depleted body fluid which was obtained from a cell-containing body fluid by removing cells.

* * * * *

UNITED STATES PATENT AND TRADEMARK OFFICE
CERTIFICATE OF CORRECTION

PATENT NO. : 10,184,145 B2
APPLICATION NO. : 14/347452
DATED : January 22, 2019
INVENTOR(S) : Martin Horlitz Page 1 of 1

It is certified that error appears in the above-identified patent and that said Letters Patent is hereby corrected as shown below:

On the Title Page

<u>Item (56) References Cited, FOREIGN PATENT DOCUMENTS:</u>
After WO 2010/072821 A1 7/2010, please insert therefor --WO 2009/102632 A2 8/2009--.

Signed and Sealed this
Seventeenth Day of September, 2019

Andrei Iancu
*Director of the United States Patent and Trademark Office*